US007504384B2

(12) United States Patent
Yedgar et al.

(10) Patent No.: US 7,504,384 B2
(45) Date of Patent: Mar. 17, 2009

(54) USE OF LIPID CONJUGATES IN THE TREATMENT OF INFECTION

(75) Inventors: Saul Yedgar, Jerusalem (IL); David Ojcius, Mariposa, CA (US)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 285 days.

(21) Appl. No.: 11/220,965

(22) Filed: Sep. 8, 2005

(65) Prior Publication Data

US 2006/0079485 A1 Apr. 13, 2006

Related U.S. Application Data

(63) Continuation-in-part of application No. 10/952,496, filed on Sep. 29, 2004, now Pat. No. 7,393,938, which is a continuation-in-part of application No. 10/627,981, filed on Jul. 28, 2003, now Pat. No. 7,101,859, which is a continuation-in-part of application No. 09/756,765, filed on Jan. 10, 2001, now Pat. No. 7,034,006.

(60) Provisional application No. 60/174,905, filed on Jan. 10, 2000, provisional application No. 60/174,907, filed on Jan. 10, 2000.

(51) Int. Cl.
*A61K 31/70* (2006.01)
(52) U.S. Cl. .............................. 514/42; 514/53; 514/54
(58) Field of Classification Search .................... 514/42, 514/53, 54
See application file for complete search history.

(56) References Cited

U.S. PATENT DOCUMENTS

| | | | |
|---|---|---|---|
| 4,604,376 A | 8/1986 | Teng | |
| 4,624,919 A | 11/1986 | Kokusho | |
| 4,654,327 A | 3/1987 | Teng | |
| 5,064,817 A | 11/1991 | Yedgar et al. | |
| 5,169,636 A | 12/1992 | Nanba et al. | |
| 5,354,853 A | 10/1994 | Staveski | |
| 5,401,511 A | 3/1995 | Margalit | |
| 5,464,942 A | 11/1995 | Sakurai et al. | |
| 5,470,578 A | 11/1995 | Aoki et al. | |
| 5,512,671 A | 4/1996 | Piantadose | |
| 5,587,363 A * | 12/1996 | Henderson | .................... 514/54 |
| 5,733,892 A | 3/1998 | Sakurai | |
| 6,022,866 A | 2/2000 | Falk et al. | |
| 6,043,231 A | 3/2000 | Pruzanski et al. | |
| 6,071,532 A | 6/2000 | Chaikof et al. | |
| 6,162,787 A | 12/2000 | Sorgente et al. | |
| 6,171,614 B1 | 1/2001 | Chaikof et al. | |
| 6,180,596 B1 | 1/2001 | Tsao | |
| 6,325,385 B1 | 12/2001 | Iwashita | |

| | | |
|---|---|---|
| 6,749,813 B1 | 6/2004 | David |

FOREIGN PATENT DOCUMENTS

| | | |
|---|---|---|
| EP | 0581282 B | 2/1994 |
| JP | 04082893 | 3/1992 |
| JP | 09030970 | 2/1997 |
| JP | 09030979 | 2/1997 |
| WO | WO 87/02777 | 5/1987 |
| WO | WO 9628544 | 9/1996 |
| WO | WO 9701330 | 1/1997 |
| WO | WO 9816198 | 4/1998 |

OTHER PUBLICATIONS

Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" *Cancer Res* 47(12):3239-45.
Balsinde, J, Balboa, MA, Yedgar, S and Dennis, EA (2000) "Group V phospholipase A(2)-mediated oleic acid mobilization in lipopolysaccharide-stimulated P388D(1) macrophages" *J Biol Chem* 275(7):4783-6.
Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" *Br J Pharmcol* 135(7):1665-74.
Brenner, T, Arnon, R, Sela, M. Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" *J Neuroimmunol* 115(1-2):152-60.
Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" *J Neurosci* 6(7):1925-33.
Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.
Cabanas, C and Hogg, N (1993) "Ligand intercellular adhesion molecule 1 has a necessary role in activation of integrin lymphocyte function-associated molecule 1" *Proc Natl Acad Sci U S A* 90 (12):5838-42.
Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.
Dan, P, Dagan, A, Krimsky, M, Pruzanski, W, Vadas, P and Yedgar, S (1998) "Inhibition of type I and type II phospholipase A2 by phosphatidyl-ethanolamine linked to polymeric carriers" *Biochemistry* 37(17):6199-204.

(Continued)

*Primary Examiner*—Rei-tsang Shiao
(74) *Attorney, Agent, or Firm*—Mark S. Cohen; Pearl Cohen Zedek Latzer LLP

(57) ABSTRACT

This invention provides compounds and methods of use thereof in suppressing, inhibiting, preventing, or treating a pathogenic effect on a cell, including, inter alia, infection with intracellular pathogens. Also provided are compounds and methods of use thereof in suppressing, inhibiting, preventing, or treating an infection in a subject.

12 Claims, 39 Drawing Sheets

OTHER PUBLICATIONS

Darville, T, Yedgar, S, Krimsky, M, Andrews, CW, Jr., Jungas, T and Ojcius, DM (2004) "Protection against *Chlamydia trachomatis* infection in vitro and modulation of inflammatory response in vivo by membrane-bound glycosaminoglycans" *Microbes Infect* 6(4):369-76.

Davidson, FF, Dennis, EA, Powell, M and Glenney, Jr, Jr. (1987) "Inhibition of phospholipase A2 by "lipocortins" and calpactins. An effect of binding to substrate phospholipids" *J Biol Chem* 262(4):1698-705.

Greaves MW and Camp RD (1988) "Prostaglandins, leukotrienes, phospholipase, platelet activating factor, and cytokines: an integrated approach to inflammation of human skin." *Arch Dermatol Res* 280:S33-41.

Krimsky, M, Dagan, A, Aptekar, L, Ligumsky, M and Yedgar, S (2000) "Assessment of intestinal permability in rats by permeation of inulin-flueorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficieny virus in red cell concentrates" *Transfusion* 36(8):743-50.

Murthy, SN, Cooper, HS, Shim, H, Shah, RS, Ibrahim, Sa and Sedergran, DJ (1993) "Treatment of dextran sulfate sodium-induced murine colitis by intracolonic cyclosporin" *Dig Dis Sci* 38(9):1722-34.

Okayasu, I, Hatekeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lightenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

Yard, BA, Yedgar, S, Scheele, M, Van Der Woude, D, Beck, G, Heinrich, B, Krimsky, M, Van Der Woude, FJ and Post, S (2002) "Modulation of IFN-gamma-induced immunogenicity by phosphatidylethanolamine-linked hyaluronic acid" *Transplantation* 73(6):984-92.

Yedgar, S, Lightenberg, D and Schnitzer, E (2000) "Inhibition of phospholipase A(2) as a therapeutic target" *Biochim Biophys Acta* 1488(1-2):182-7.

Soeda et al (Biochemistry 29:5188-5144) Tissue Plasminogen Activator Catalyzed Lys-Plasminogen Activation on Heparin-Inserted Phospholipid Liposomes.

Parish et al (Int. J. Cancer 40: 511-518, "Evidence that sulphated polysaccharides inhibit tumour metastatis by blocking tumour-cell-derived heparanases."

Wang D.P, Matthias Schuster, Yi Fong Wang, Chi Huey Wong "Synthesis of phospholipid-inhibitor conjugates by enzymic transphosphatidylation with phospholipase", J. Am. Chem. Soc.; 1993; 115(23); 10487-10491.

Carey et al, "Contrasting effects of cycloxygenase-1 (cox-1) and cox-2 deficiency in the host response to influenze, a viral infection", Journ. Of Immunology 2005, vol. 15: 175 (10):6878-84.

Okayasu, I, Hatakeyama S, Yamada, M. Ohkusa. T, Inagaki, Y and Nakaya. R (1990) "A novel method in the induction of reliable experimental acute and chronic ulcerative colitis in mice" *Gastroenterology* 98(3):694-702.

Schnitzer, E. Dagan. A, Krimsky, M. Lichtenberg. D, Pinchuk, I. Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer. E, Yedgar. S. Danino, D, Talmon. Y and Lichtenberg. D (1999) "The Interaction of hyaluronic-phosphatidylethanolamine with low density lipoprotein (LDL) and its effect on copper induced LDL oxidation" *Biophysical Journal* 76(1): Part 2.

Schnitzer. E. Pinchuk, I. Fainaru. M, Lichtenberg. D and Yedgar. S (1998) "LDL-associated phospholipase A does not protect LDL against lipid peroxidation in vitro" *Free Radic Biol Med* 24(7-8):1294-303.

Yard, BA. Yedgar, S. Schelle, M. Van Der Woude. D. Beck. G, Heidrich. B. Krimsky, M. Van Der Woude. FJ and Post. S (2002) "Modulation of IFN-Gamma-induced immunogenicity by phosphatidylethanolamine-linked hyaluronic acid" *Transplantation* 73(6):984-92.

Yedgar, S, Lichtenberg. D and Schnitzer. E (2000) "Inhibition of phospholipase A(2) as a therapeutic target" *Biochim Biophys Acta* 1488(1-2):182-7.

Carey. et al (2005 Contrasting Effects of Cycloxygenase-1 (COX-1) and COX-2 Deficiency on the Host Response to Influenza A Viral Infection Journal of Immunol 15; 175 (10): 5878-84.

Albini, A, Iwamoto. Y. Kleinman, HK, Martin. GR, Aaronson. SA. Kozlowski, JM and McEwan. RN (1987) "A rapid in vitro assay for quantitating the invasive potential of tumor cells" *Cancer Res* 47(12):3239-45.

Balsinde. J. Balboa, MA, Yedgar. S and Dennis, EA (2000) "Group V phospholipase A(2)-mediated oleic acid mobilization in lipopolysaccharide-stimulated P388D(1) macrophages" *J Biol Chem* 275(7):4783-6.

Beck. G. Yard, BA, Schulte. J: Oberacker, R, Van Ackern, K, Van Der Woude, FJ. Krimsky, M, Kaszkin. M and Yedgar, S (2002) "Inhibition of LPS-induced chemokine production in human lung endothelial cells by lipid conjugates anchored to the membrane" *Br J Pharmacol* 135(7):1665-74.

Chen, WM, Soria. J, Soria, C, Krimsky. M and Yedgar, S (2002) "Control of capillary formation by membrane-anchored extracellular inhibitor of phospholipase A(2)" *FEBS Lett* 522(1-3):113-8.

Dan. P. Dagan, A, Krimsky, M, Pruzanski, W, Vadas, P and Yedgar. S (1998) "Inhibition of type I and type II phospholipase A2 by phosphatidyl-ethanolamine linked to polymeric carriers" *Biochemistry* 37(17):6199-204.

Darville, T, Yedgar, S, Krimsky. M. Andrews, CW, Jr. Jungas. T and Ojcius. DM (2004) "Protection against *Chlamydia trachomatis* infection in vitro and modulation of inflammatory response in vivo by membrane-bound glycosaminoglycans" *Microbes Infect* 6(4):369-76.

Krimsky. M. Dagan. A, Aptekar, L, Ligumsky, M and Yedgar. S (2000) "Assessment of intestinal permability in rats by permeation of inulin-fluorescein" *J Basic Clin Physiol Pharmacol* 11(2):143-53.

Krimsky. M. Yedgar. S. Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Okayasu, I. Hatakeyama. S, Yamada, M, Ohkusa, T. Inagaki, Y and Nakaya, R (1990) "A novel method in the induction of reliable experimental acute and chronic ulcerative colitis in mice" *Gastroenterology* 98(3):694-702.

Schmiel, DH and Miller. VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar. S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer. E, Yedgar. S, Danino. D. Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer. E, Pinchuk. I. Fainaru, M. Lichtenberg. D and Yedgar. S (1998) "LDL-associated phospholipase A does not protect LDL against lipid peroxidation in vitro" *Free Radic Biol Med* 24(7-8):1294-303.

Yard, BA, Yedgar, S, Scheele. M, Van Der Woude, D, Beck. G. Heidrich, B. Krimsky, M, Van Der Woude, FJ and Post, S (2002) "Modulation of IFN-gamam-induced immunogenicity by phosphatidylethanolamine-linked hyaluronic acid" *Transplantation* 73(6):984-92.

Yedgar, S. Lichtenberg. D and Schnitzer. E (2000) "Inhibition of phospholipase A(2) as a therapeutic target" *Biochim Biophys Acta* 1488(1-2):182-7.

\* cited by examiner

Fig. 1.1: Effect of Lipid-conjugates on HIV infectivity
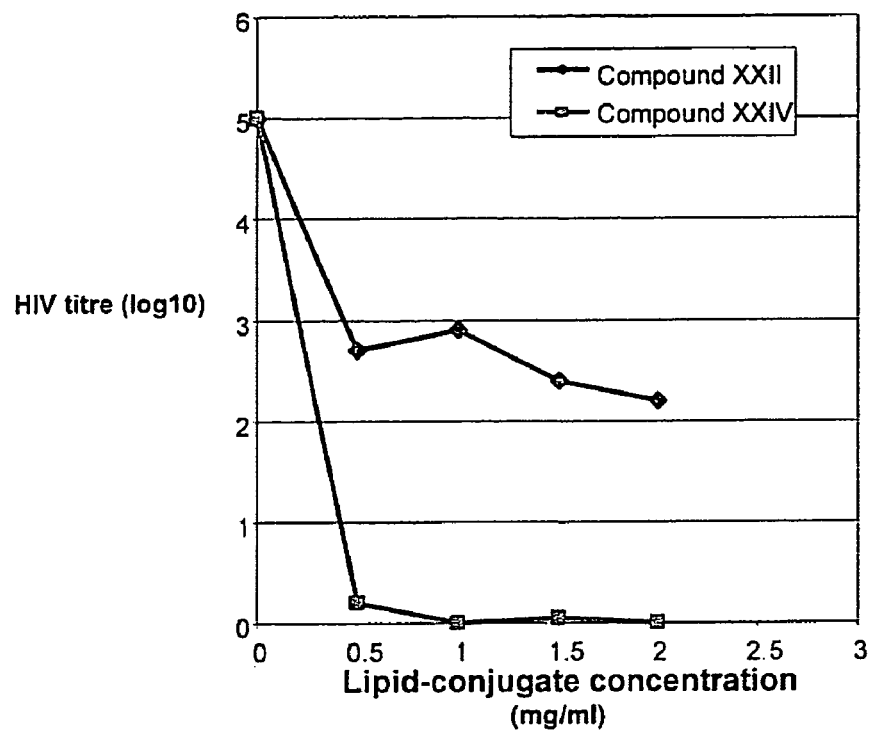
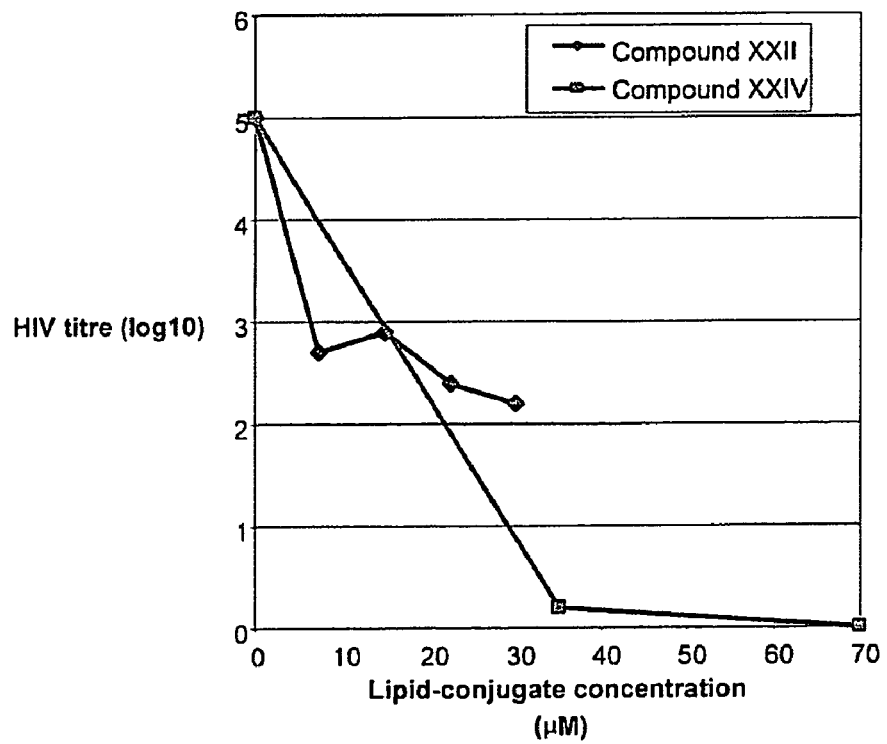

Fig. 2.1: Effect of Lipid-conjugates on infection of HeLa cells by *Chlamydia*.
A
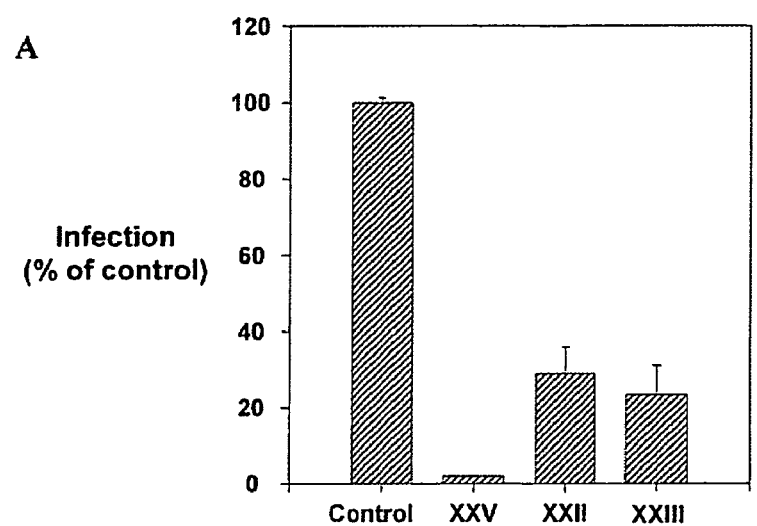
B
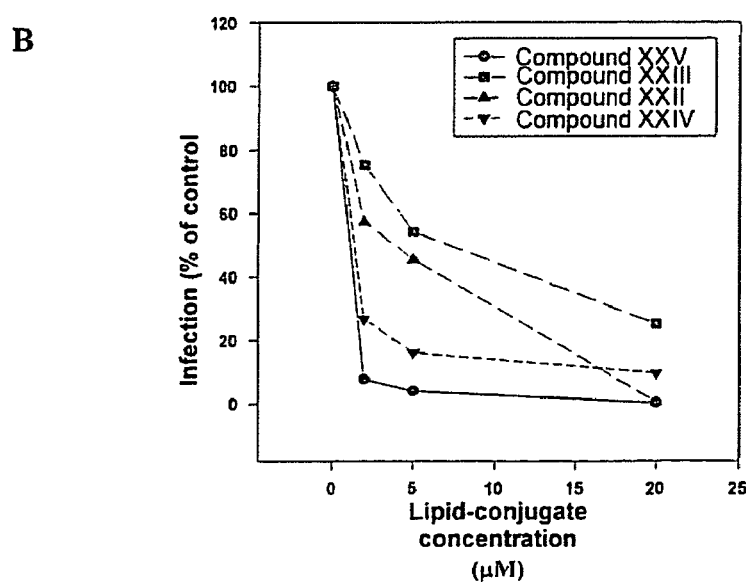

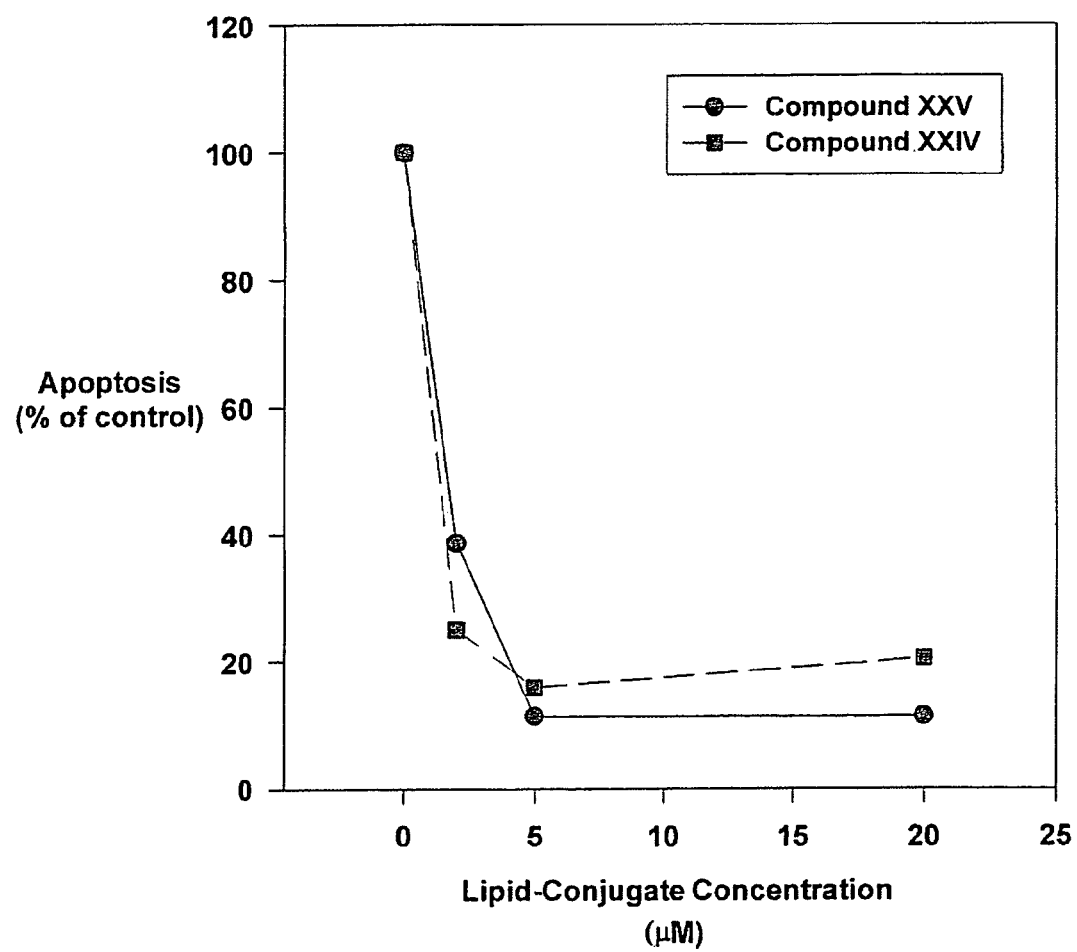
Fig. 2.2: Effect of Lipid-conjugates on *Chlamydia*-induced apoptosis of HeLa cells.

Fig. 3.1: Inhibition of endothelin-1 (ET)-induced contraction of rat tracheal rings by Lipid-conjugates.
A: Contraction of rat trachea by Endothelin-1.
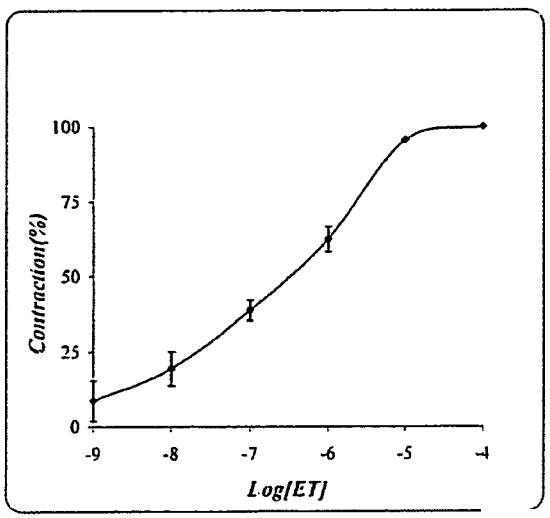
B: Effect of Compound XXII on ET- induced contraction of rat trachea.
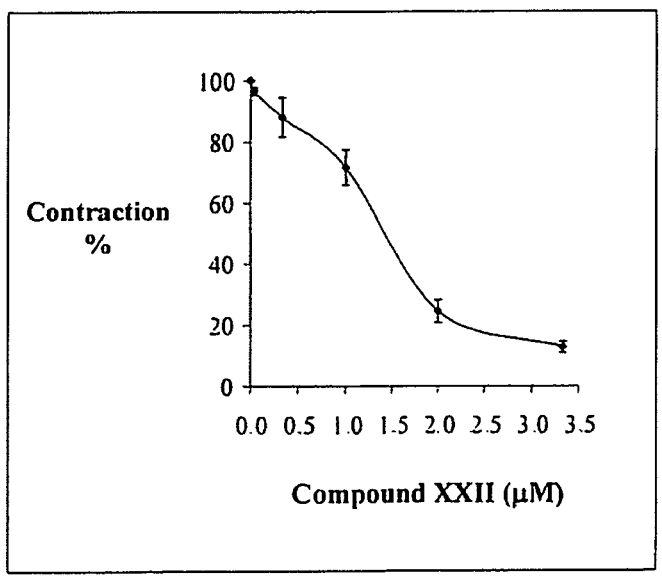

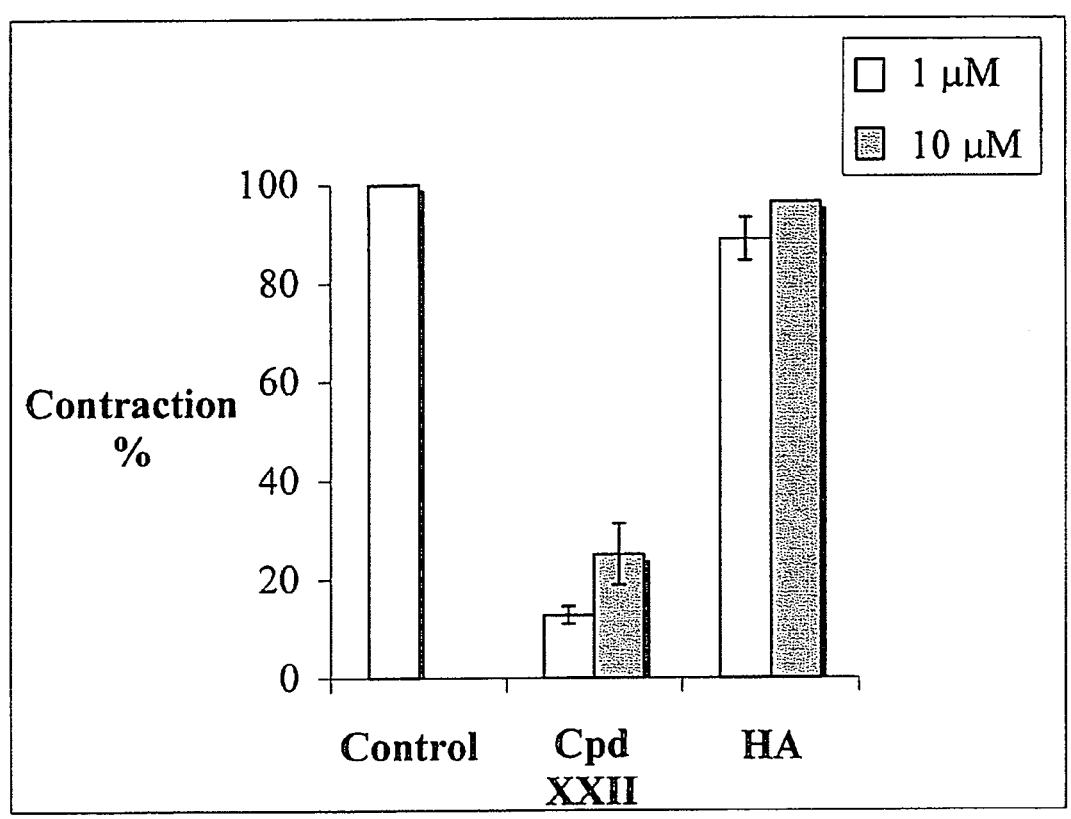
Fig. 3.2: Effect of Compound (Cpd) XXII and Hyaluronic acid (HA) on ET-1- induced contraction of rat trachea.

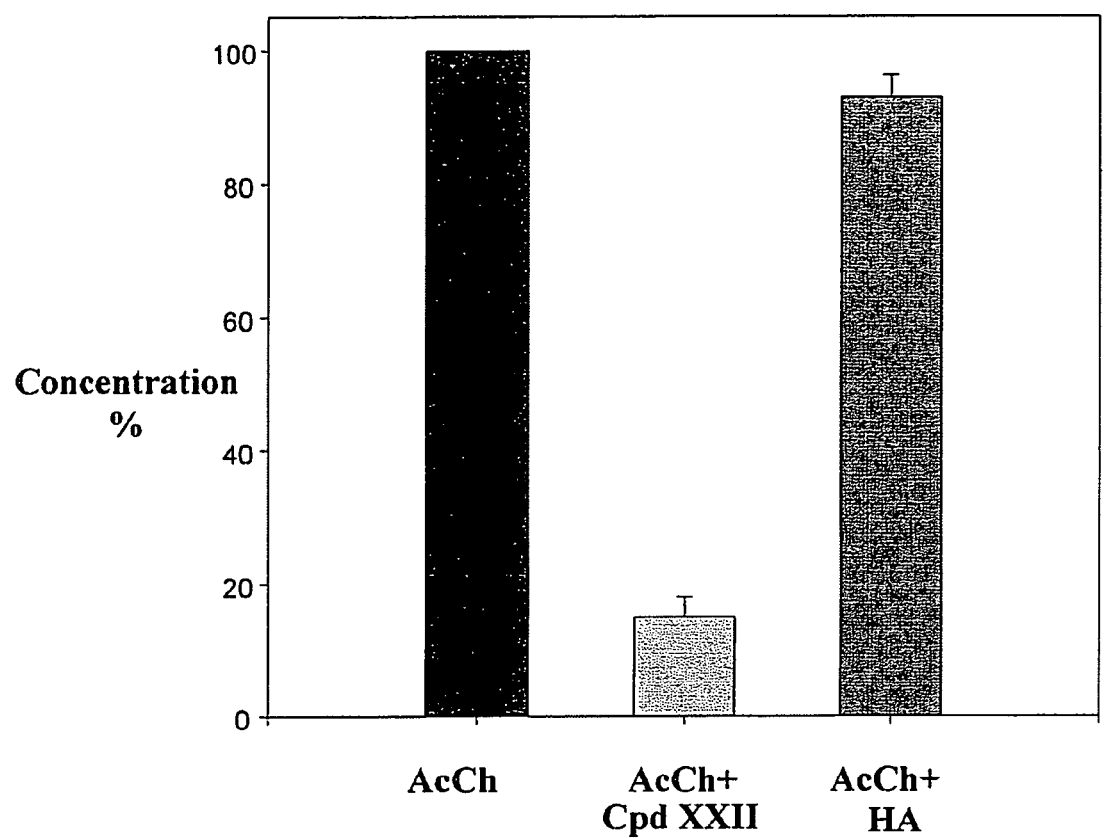
Fig 3.3: Effect of Compound (Cpd) XXII and Hyaluronic acid (HA) on Acetylcholine (AcCh) – induced contraction of isolated rat trachea rings.

Fig. 3.4: Effect of Compound XXII, administered subcutaneously, on early asthmatic reaction (EAR) induced by ovalbumin inhalation
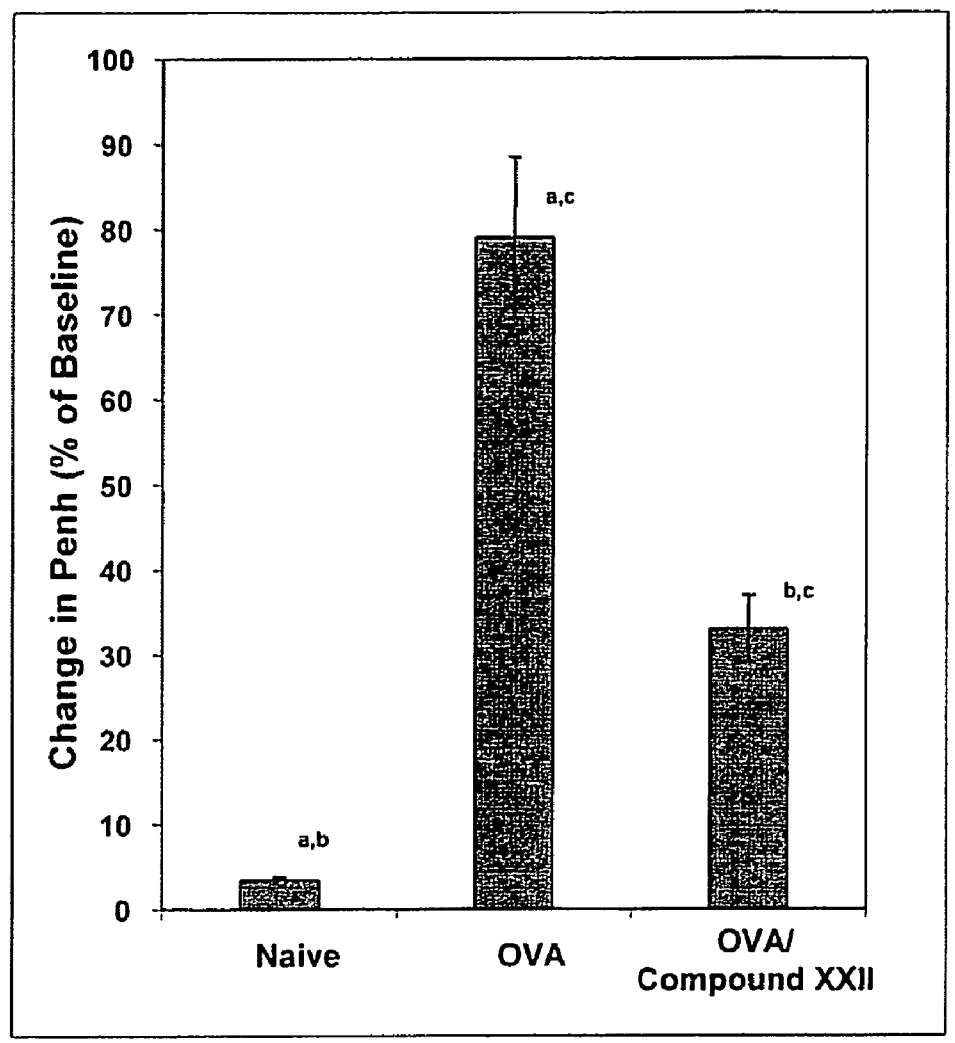

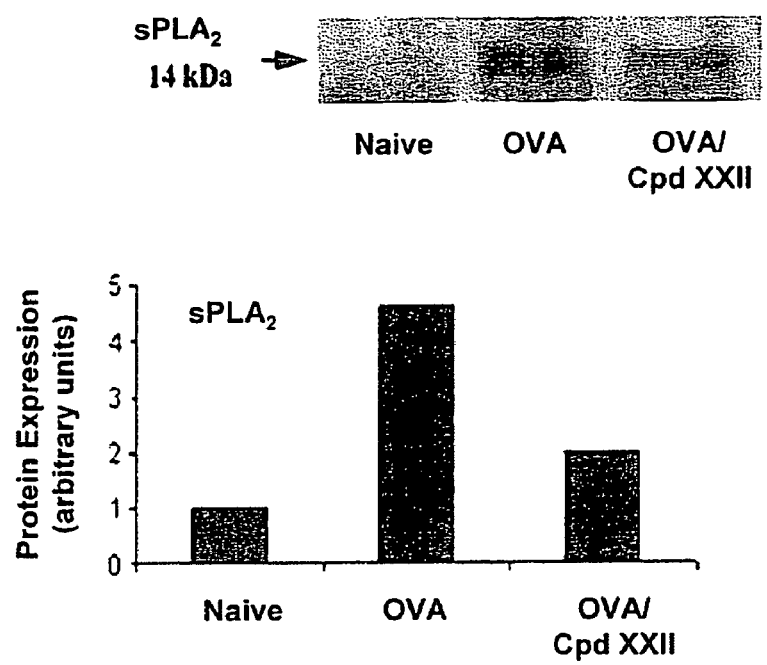
Fig. 3.5: Effect of Compound (Cpd) XXII on sPLA$_2$ expression in lung of rats with OVA-induced asthma Fig. 3.6: Effect of Compound XXII on cysteinyl leukotriens ($LTC_4$, $LTD_4$ and $LTE_4$) level in the BAL of OVA-induced asthmatic rats
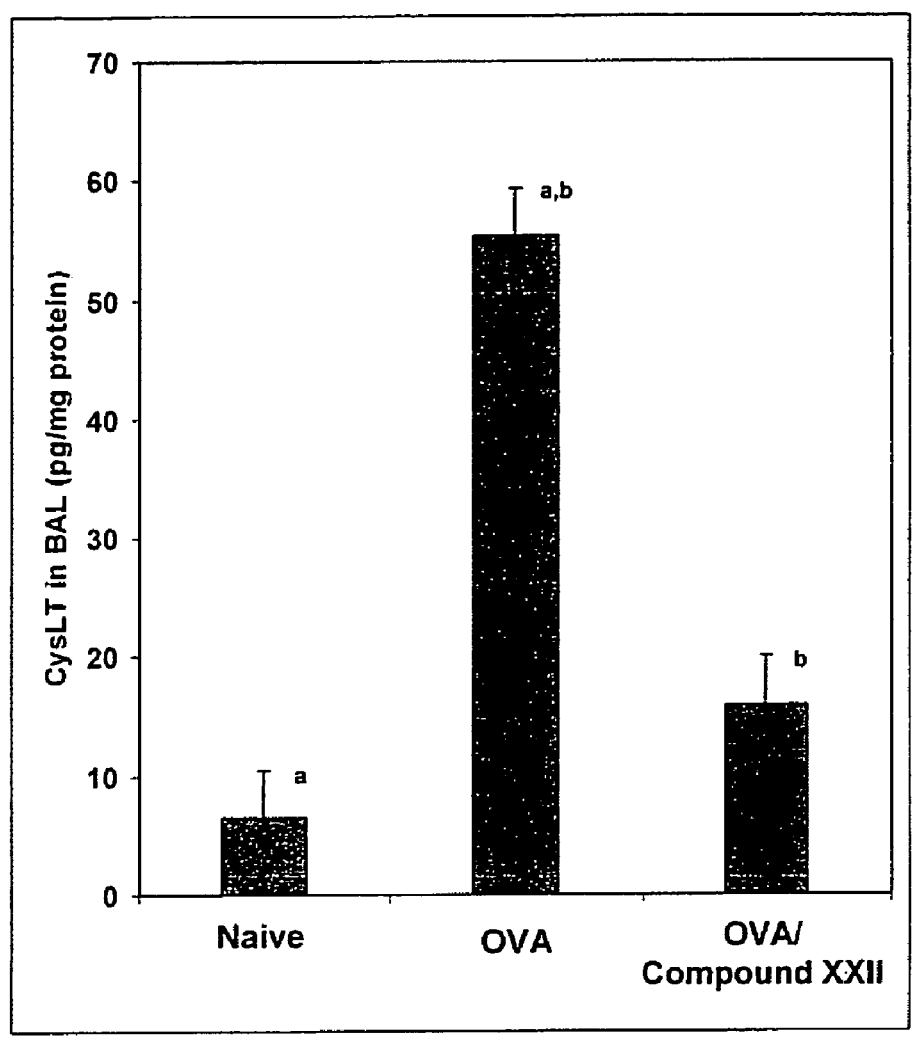

Fig. 3.7: Effect of Compound XXII inhalation on early and late asthmatic reaction (EAR and LAR, respectively) in OVA-sensitized asthmatic rats.
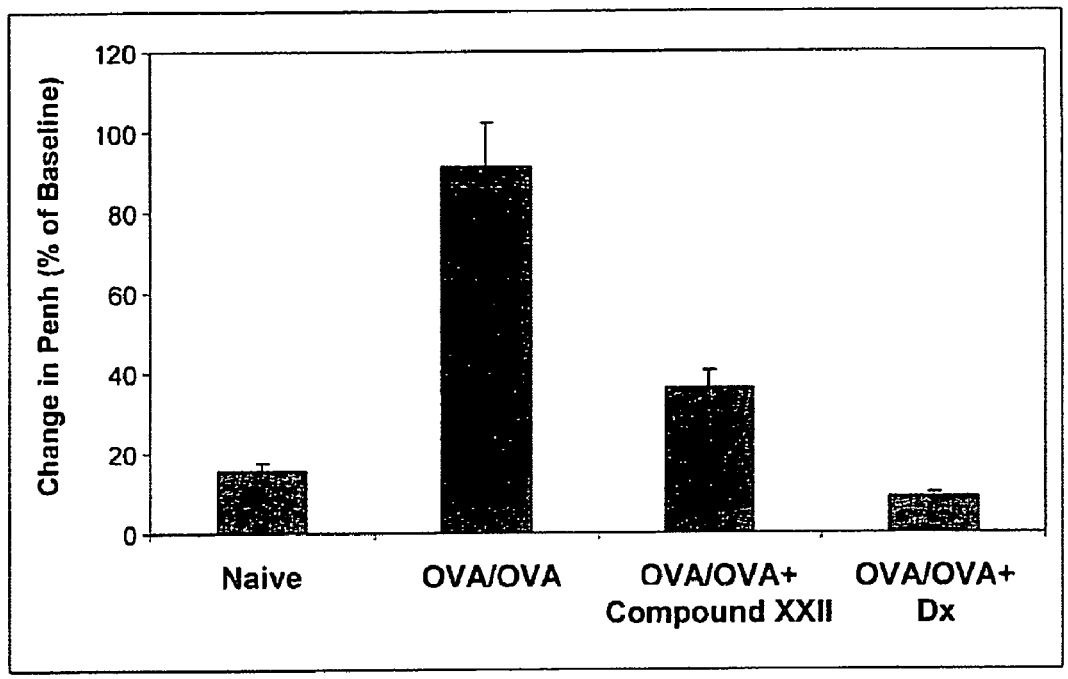
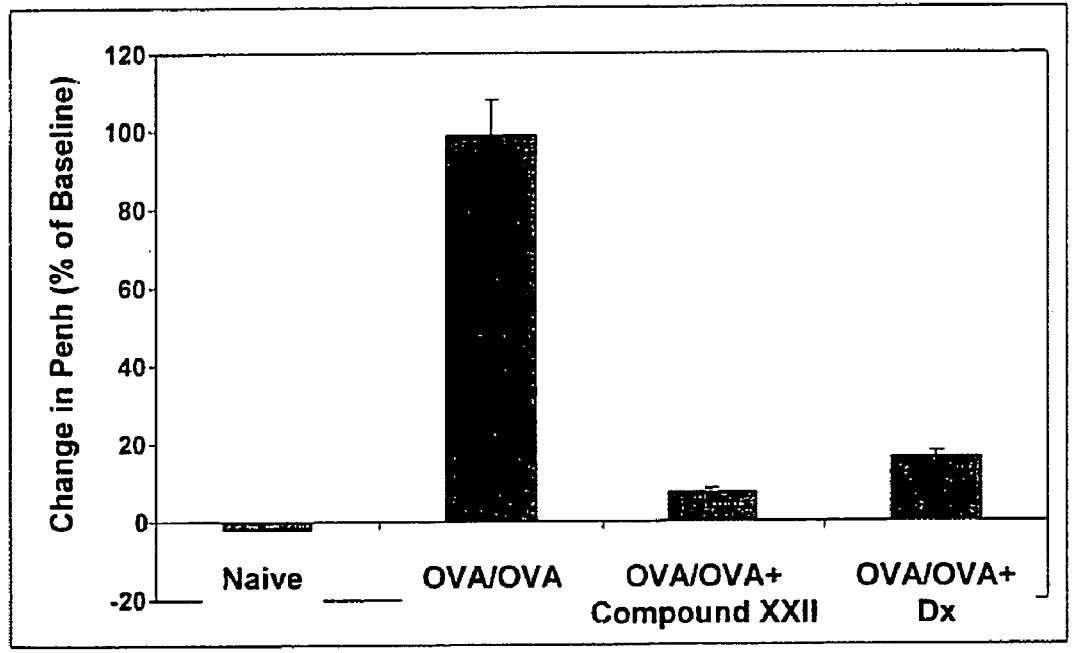

Fig. 3.8: Effect of Compound XXII inhalation on cysteinyl leukotriens (LTC4, LTD4 and LTE4) level in the BAL of OVA-sensitized asthmatic rats
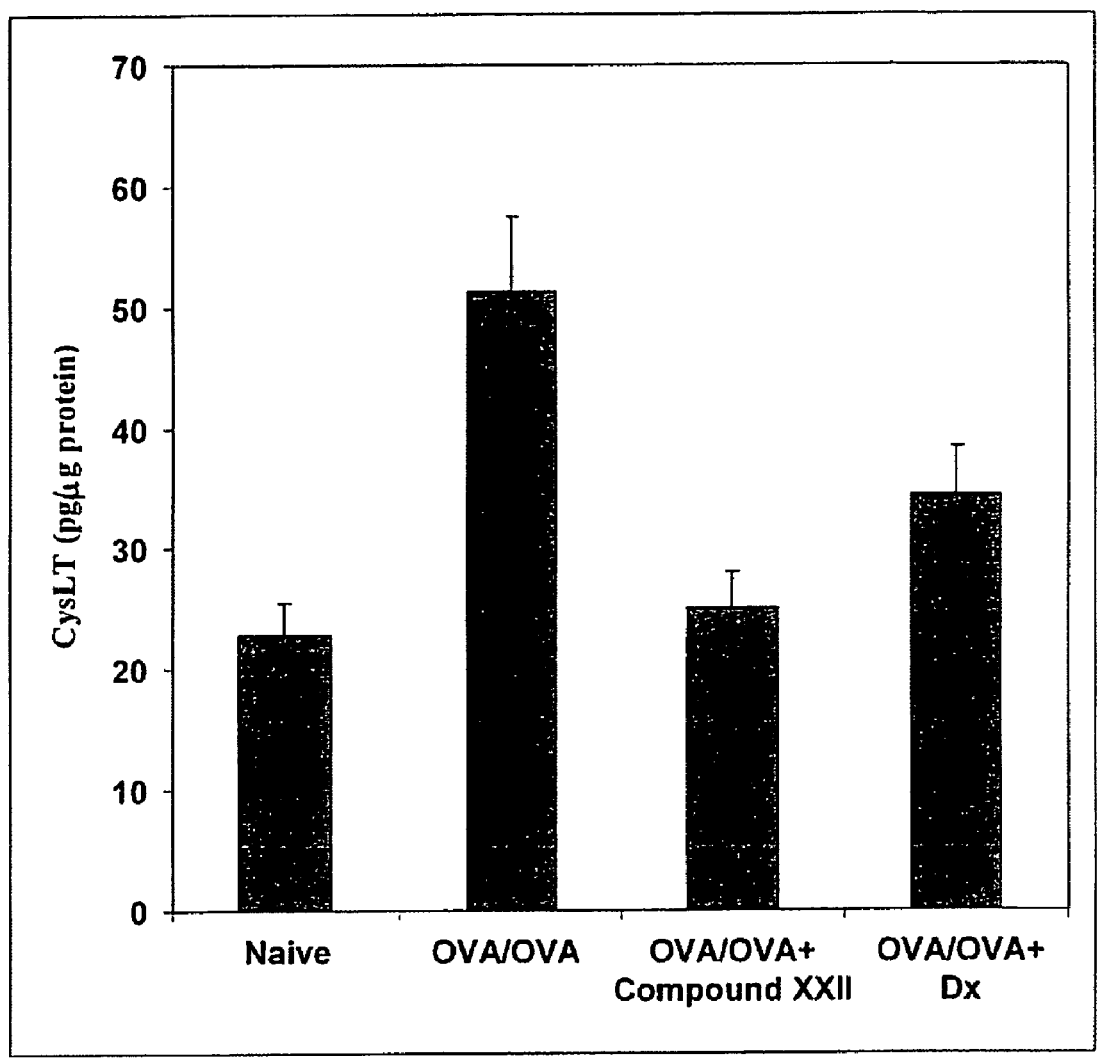

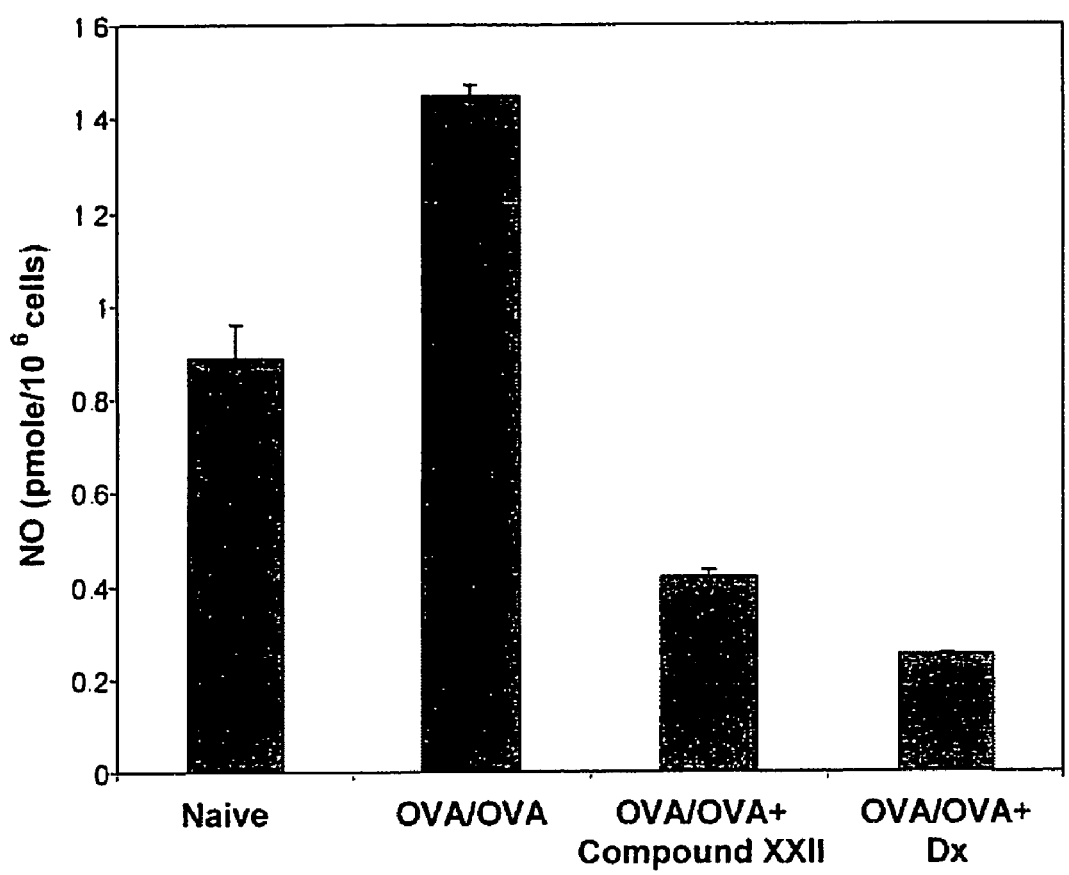
Fig. 3.9: Effect of Compound XXII inhalation on NO production by macrophages collected from the BAL of OVA-sensitized asthmatic rats.

Fig. 3.10: Effect of Compound XXII inhalation on structural change in airways (airway remodeling) of OVA sensitized asthmatic rats.
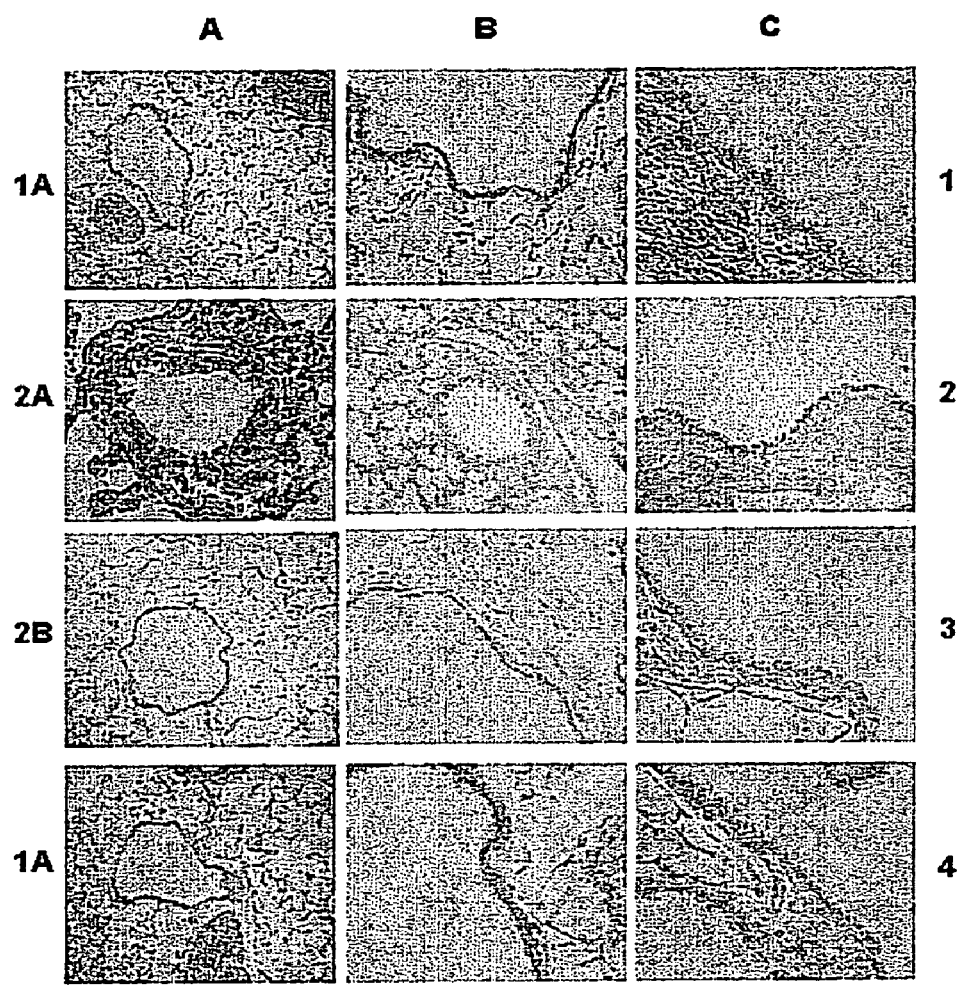

Fig. 3.11: Effect of Compound (Cpd) XXII on remodeling of asthmatic rat airway; histological morphometry.
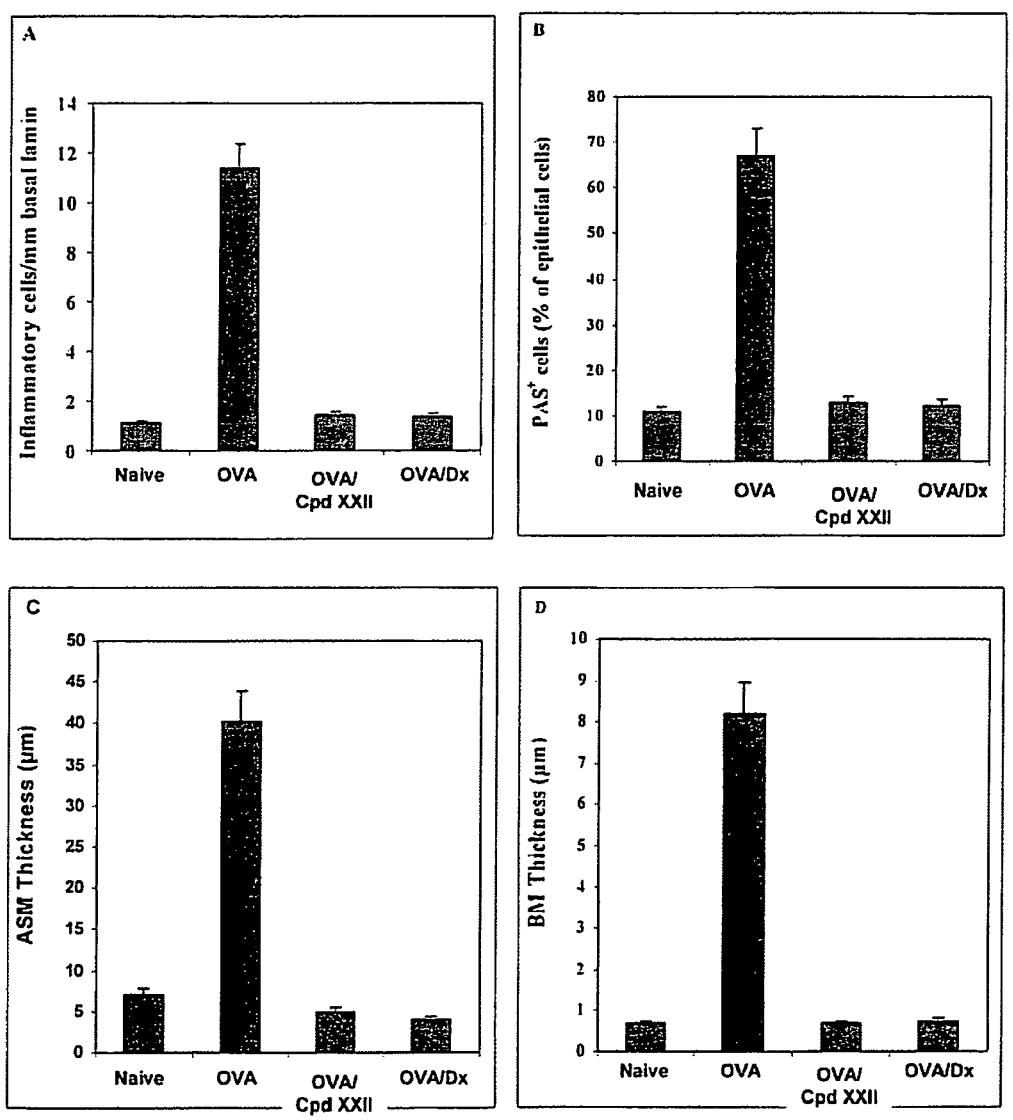

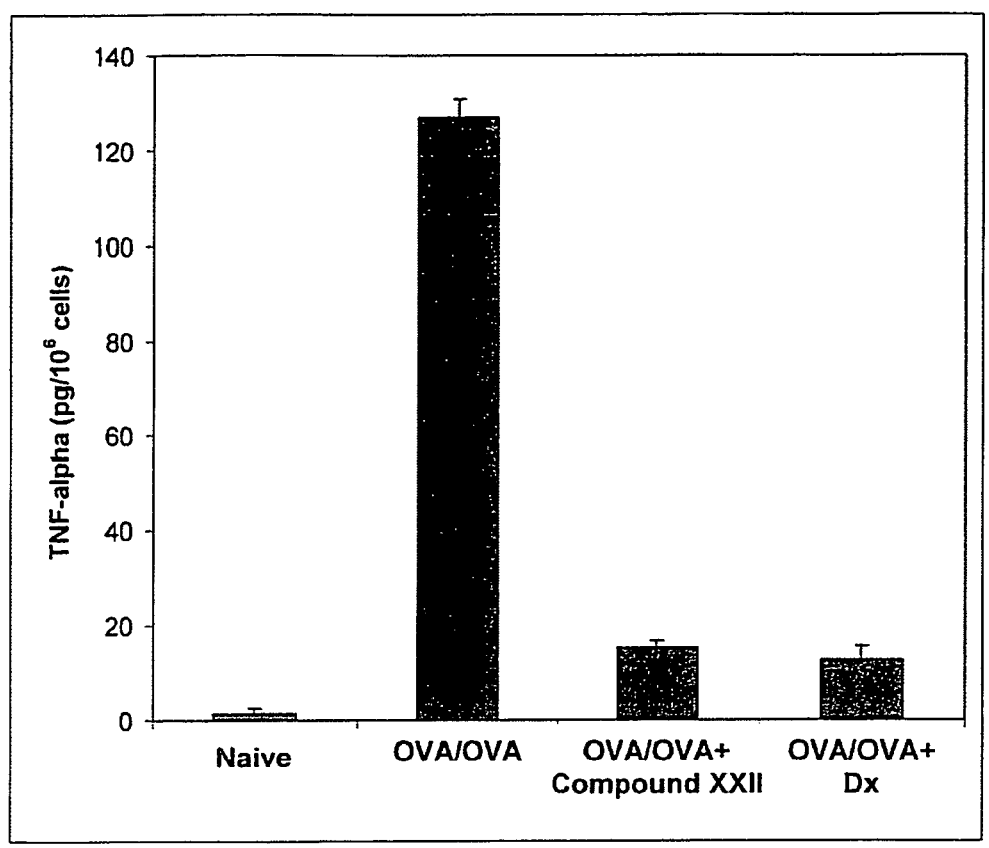
Fig. 3.12: Effect of Compound XXII inhalation on TNFα production by macrophages collected from the BAL of OVA-sensitized asthmatic rats.

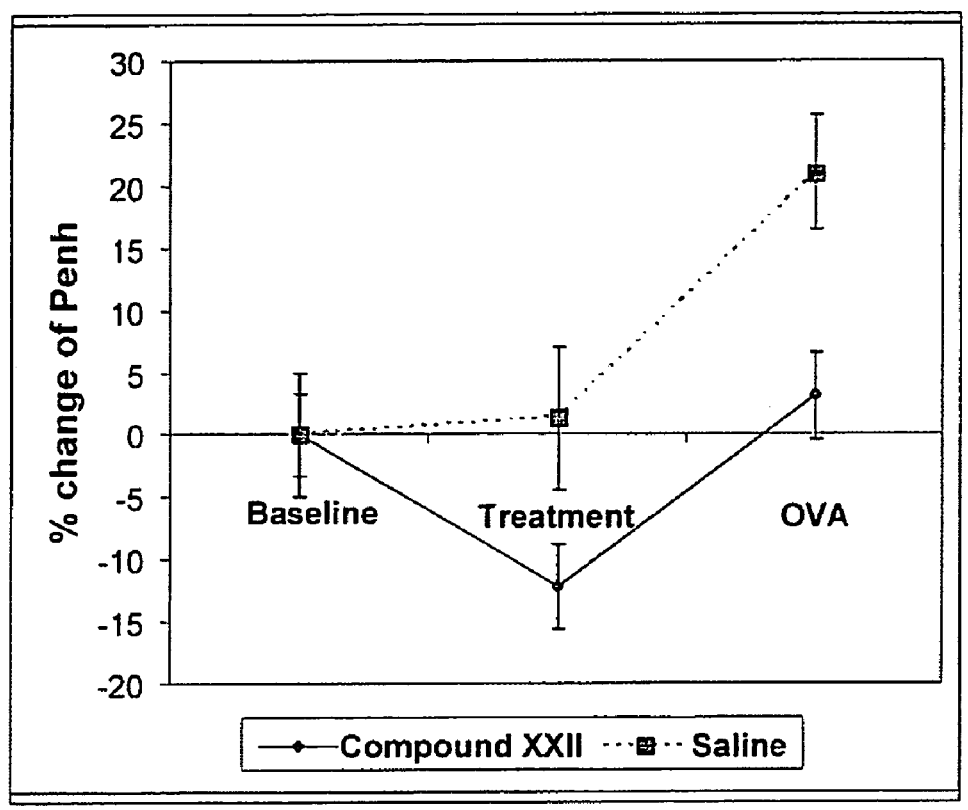
Fig. 3.13: Amelioration of OVA-induced broncho-constriction by Compound XXII inhalation before challenge.

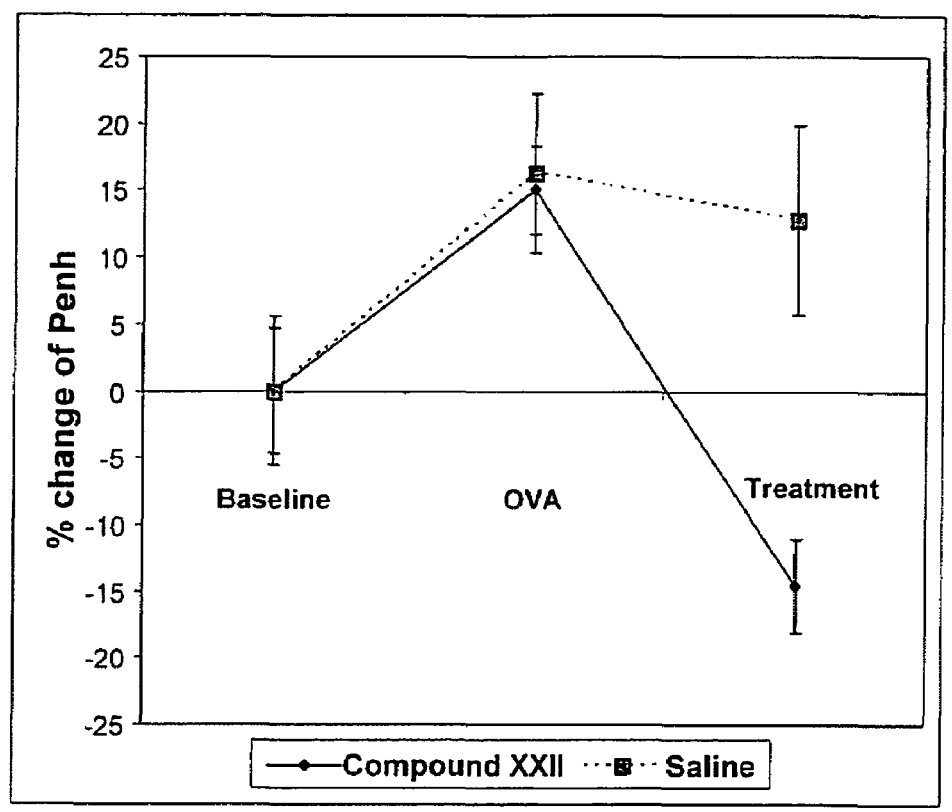
Fig. 3.14: Amelioration of OVA-induced broncho-constriction by Compound XXII inhalation after challenge.

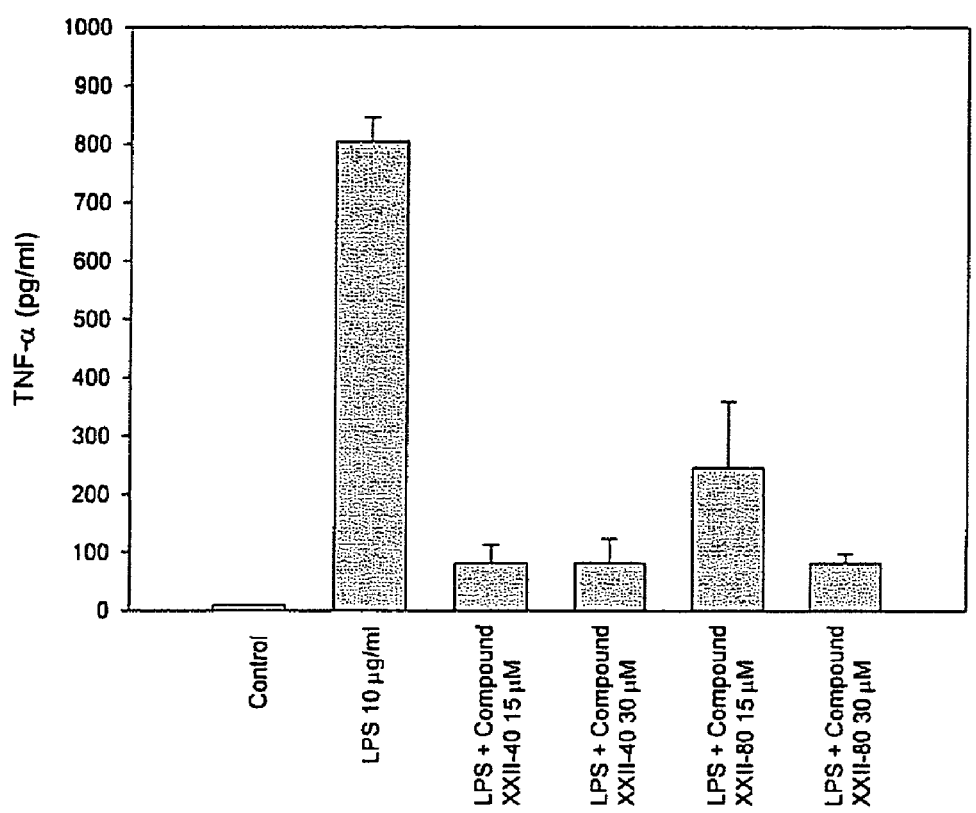
Fig. 4.1-I: Effect of lipid-conjugates on LPS-induced production of TNFα in human whole blood.

Fig. 4.1-II: Effect of Compound XXII on LPS-induced production of TNFα in human whole blood.
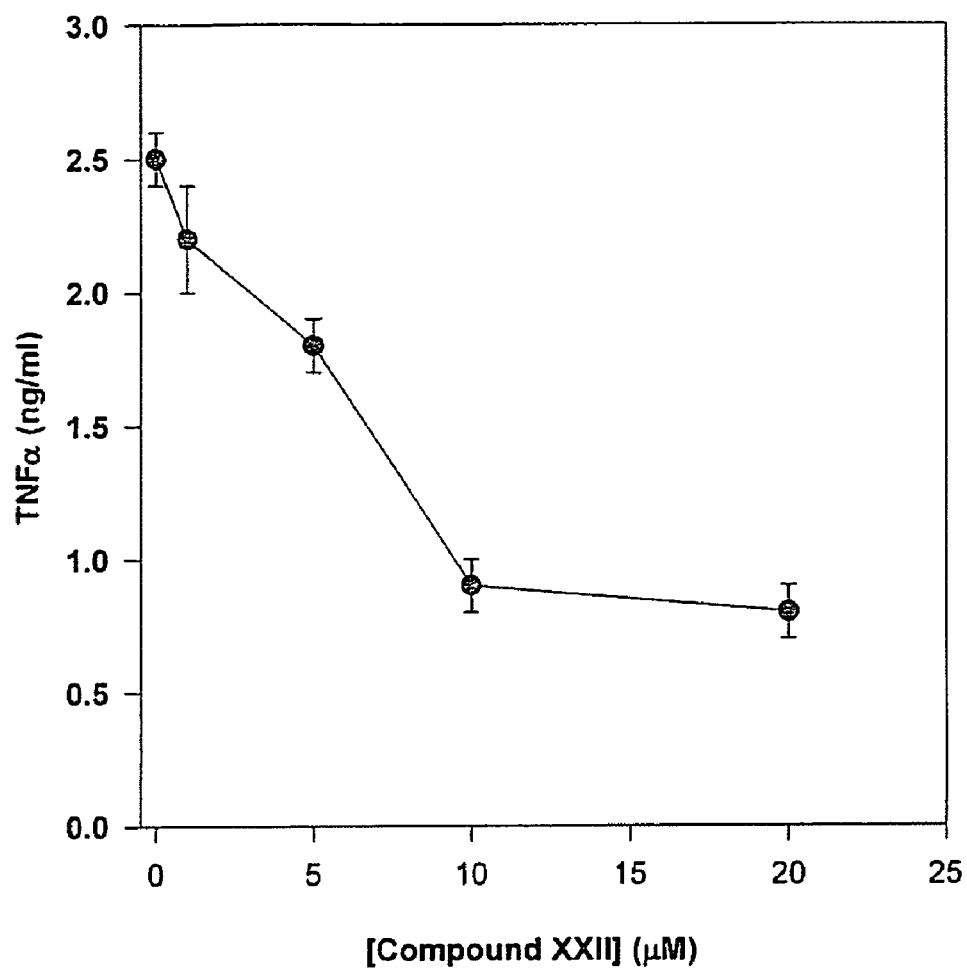

Fig. 4.2: Effect of Compound XXII on rat survival in LPS-induced endotoxinemia.
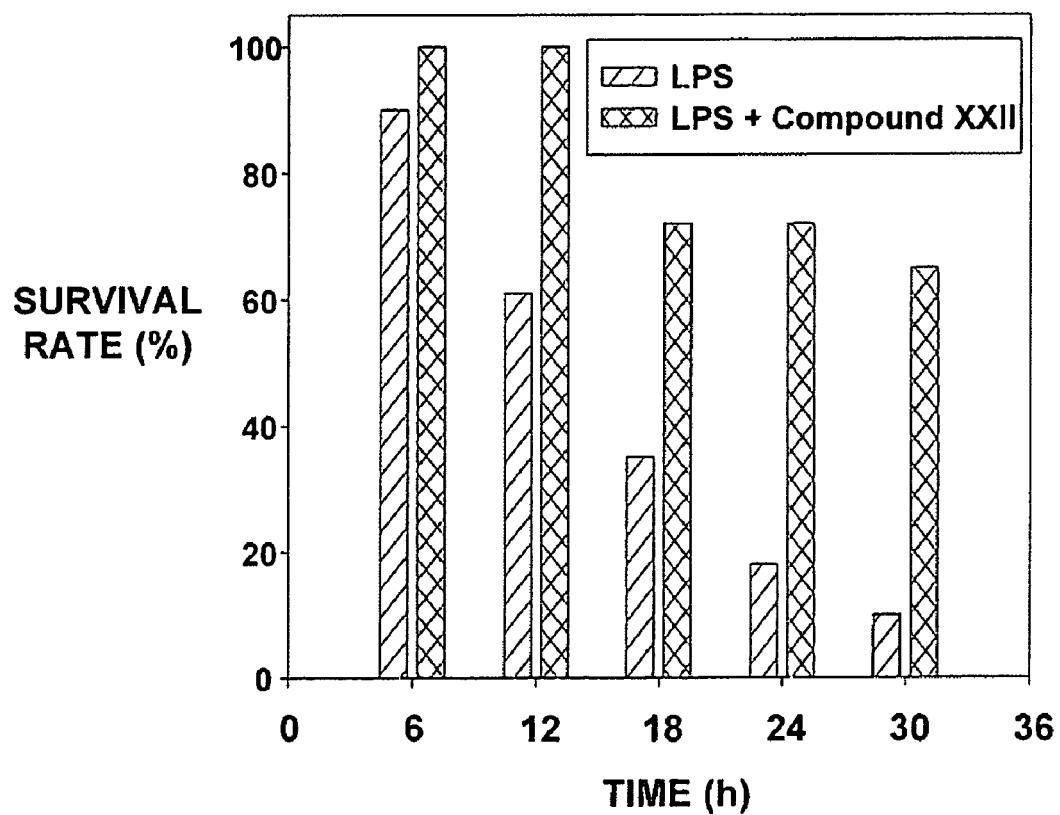

Fig. 4.3: Effect of Compound (Cpd) XXII on serum levels of TNF-α and IL-6 in septic rats.
A
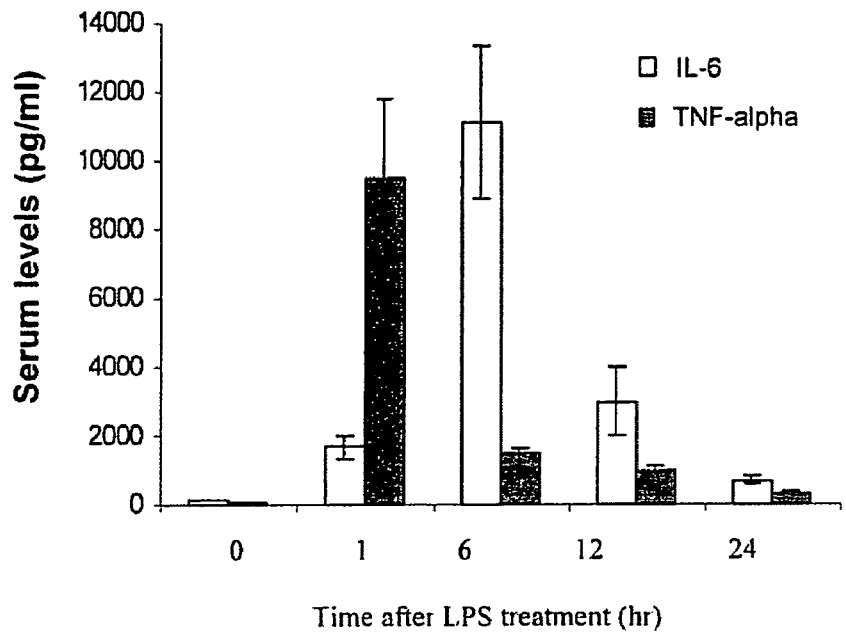
B
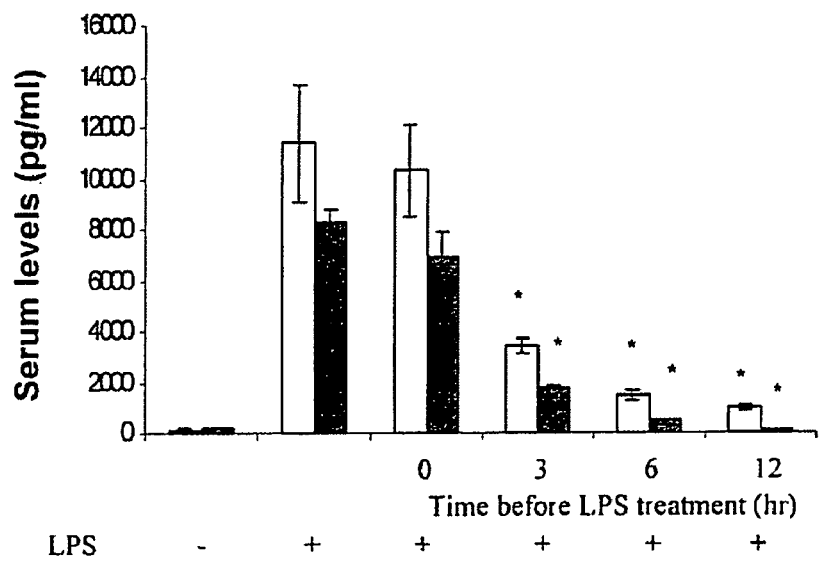

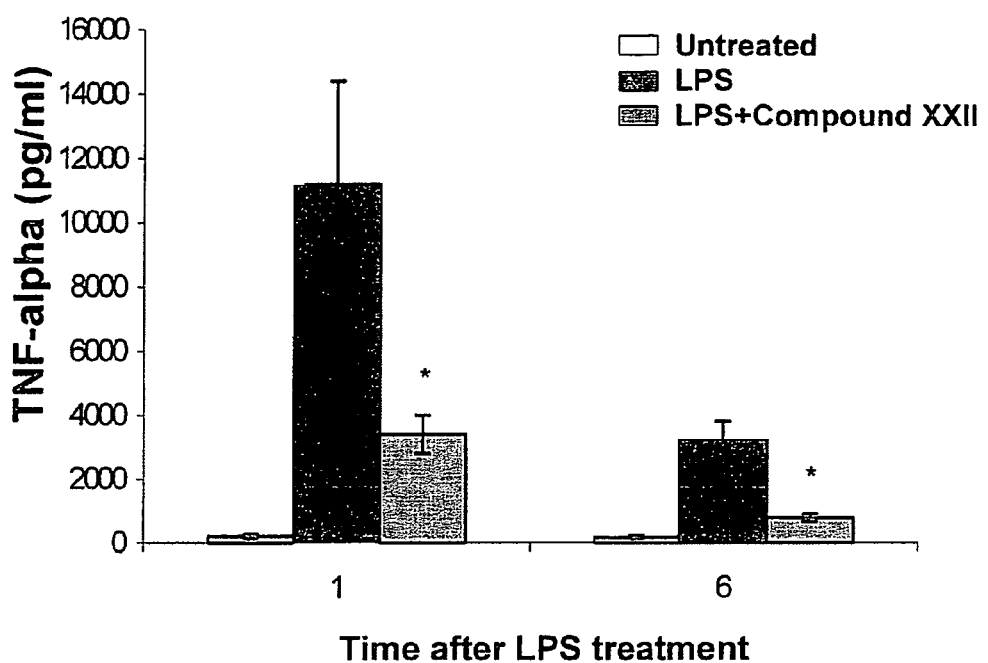
Fig. 4.4: Effect of Compound XXII on TNF-α production after i.p. administration of LPS and simultaneous i.v. administration of Compound XXII.

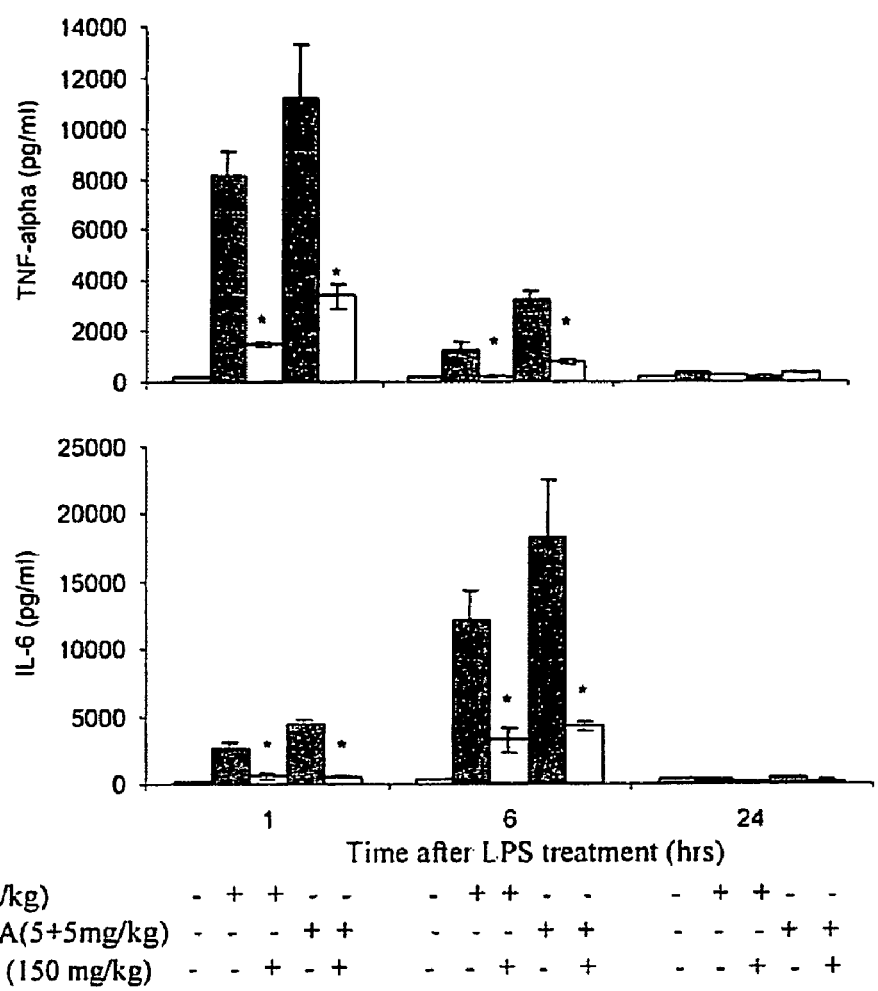
Fig. 4.5: Effect of Compound (Cpd) XXII on serum cytokine levels in rats injected with LPS or LPS + LTA.

Fig. 4.6: Effect of Compound XXII on mRNA expression of IL-1, TNF-α and IL-6 genes in lung and liver of rats with LPS-induced sepsis.
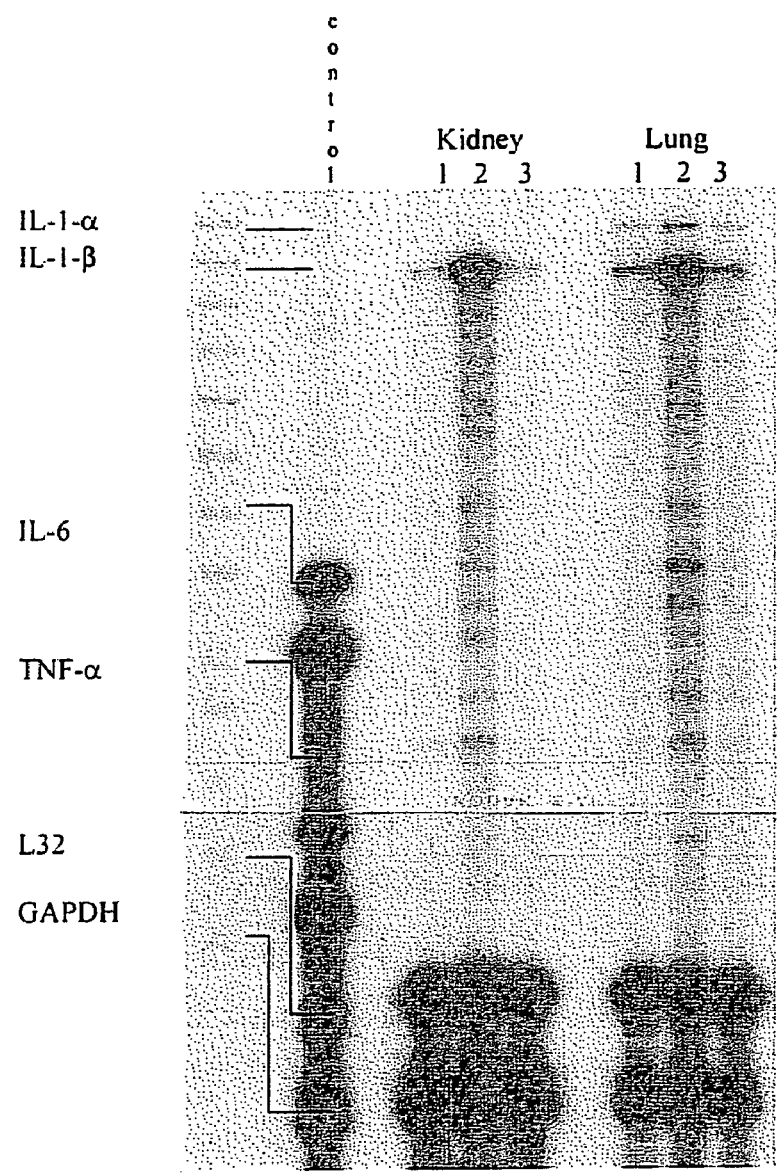

Fig. 4.7: Effect of Compound XXII on mRNA expression of sPLA$_2$-IIA and iNOS genes in kidney and lung of rats with LPS-induced sepsis
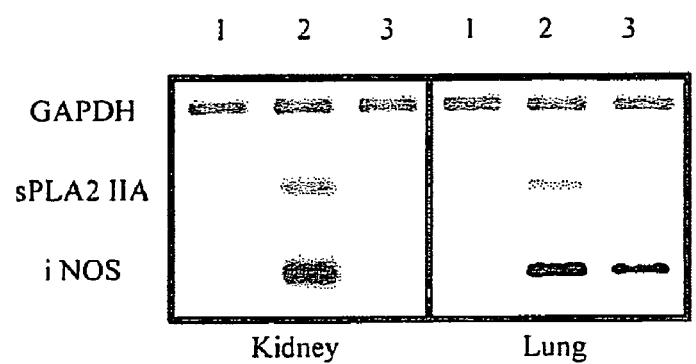

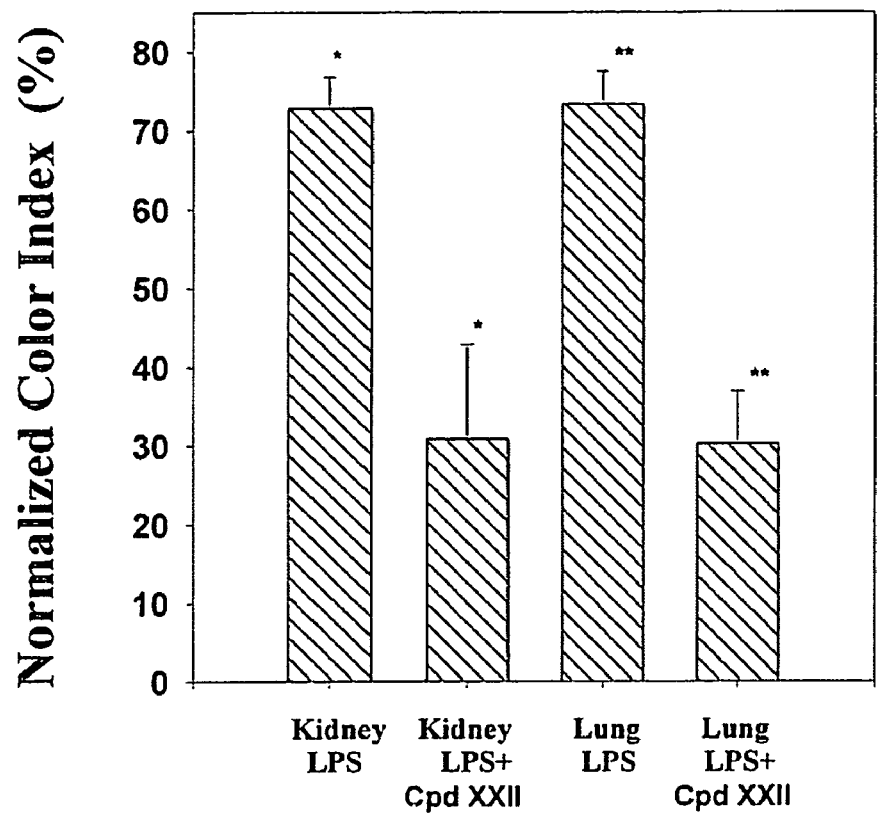
Fig. 4.8: Effect of Compound (Cpd) XXII on ICAM-1 expression in lung and kidney of rats with LPS-induced sepsis.

Fig. 6.1: Compound (Cpd) XXVI protects BGM cells from membrane lysis induced by combined action of hydrogen peroxide produced by glucose oxidase (GO) and exogenous phospholipase $A_2$ ($PLA_2$).
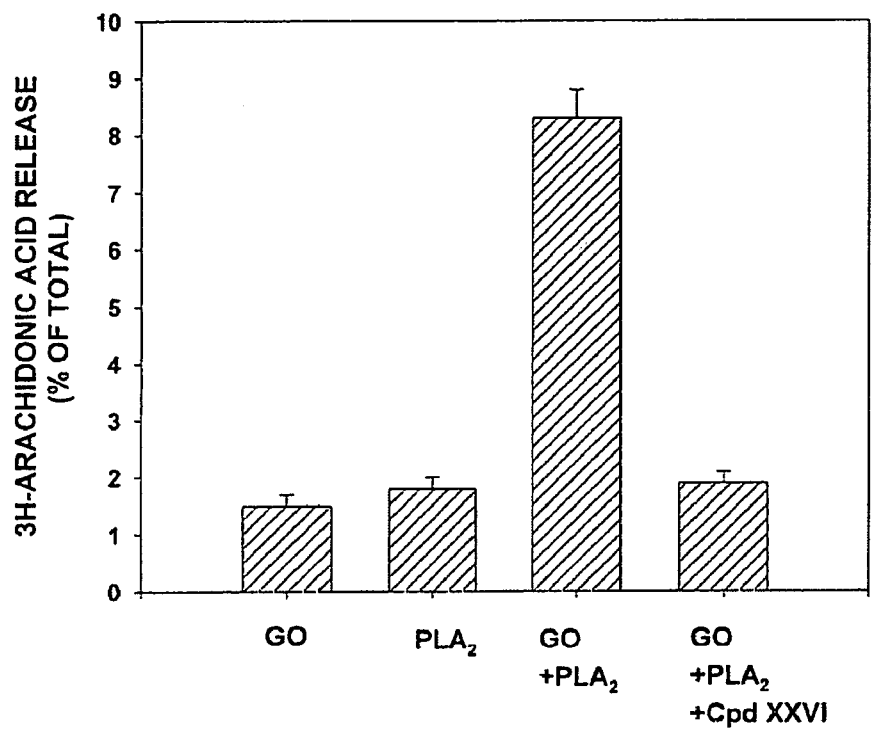

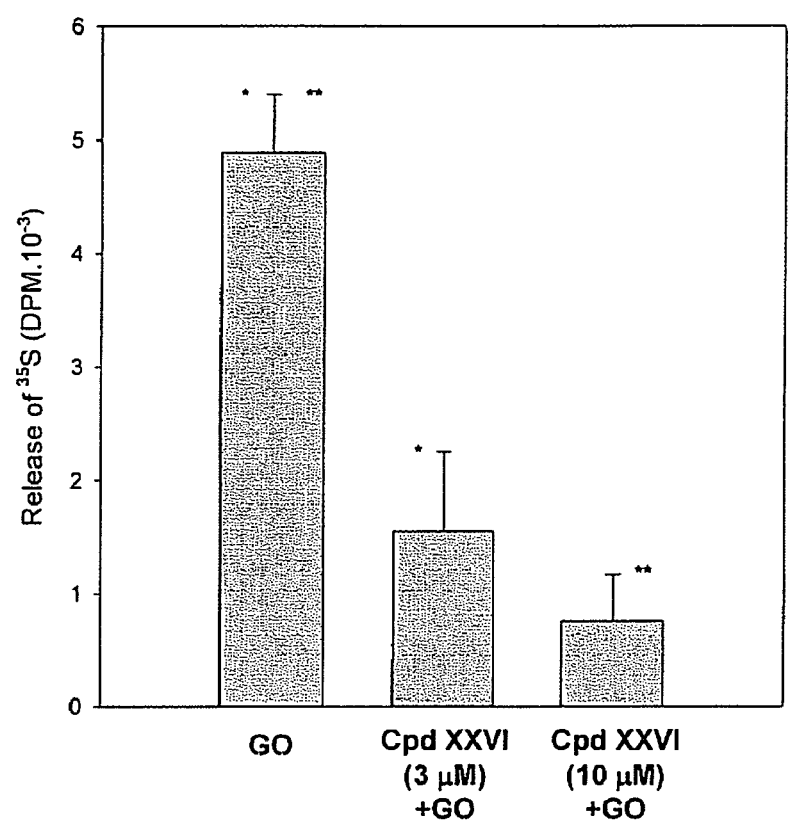
Fig. 6.2: Compound (Cpd) XXVI protects BGM cells from glycosaminoglycan degradation by hydrogen peroxide produced by glucose oxidase (GO).

Fig. 6.3: Compound XXII protects LDL from copper-induced oxidation.
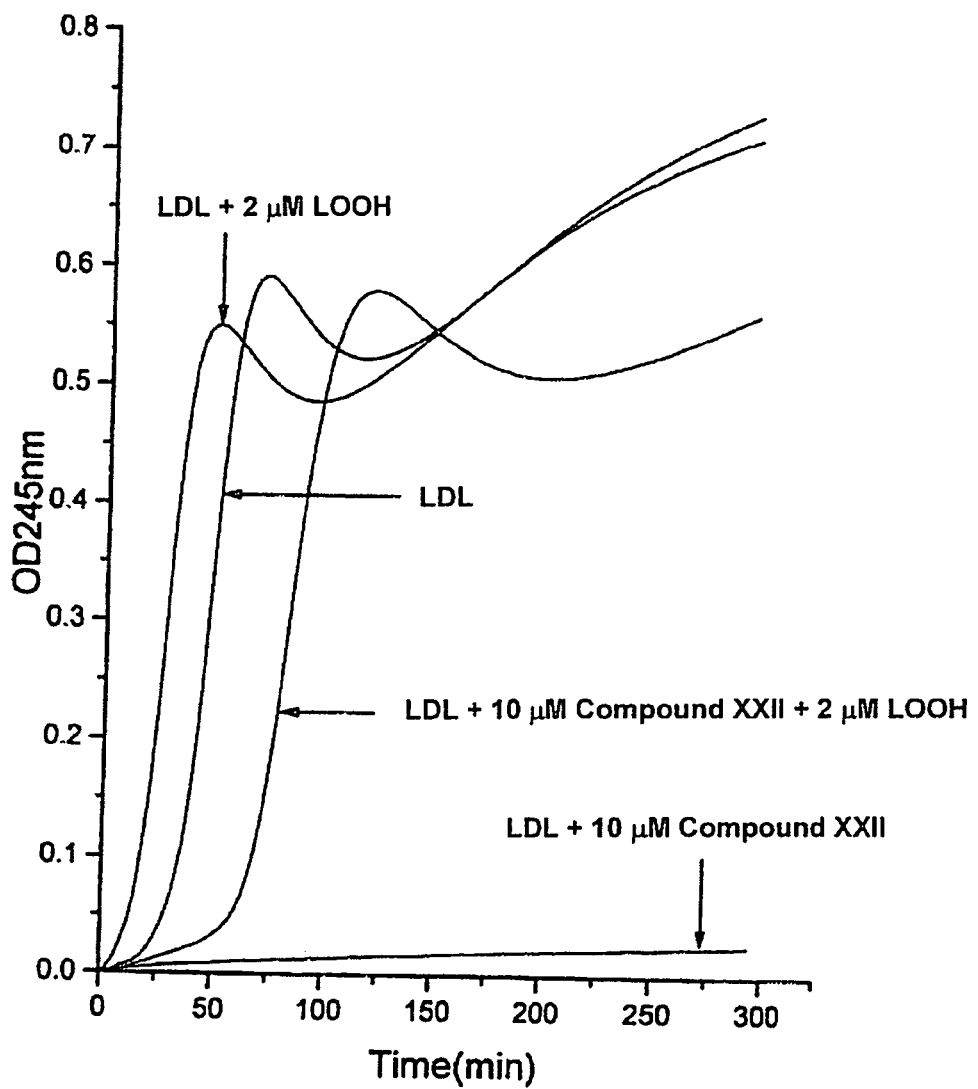

Fig. 7.1: Lipid-conjugates inhibit the secretion of PGE$_2$ from glial cells stimulated by LPS.
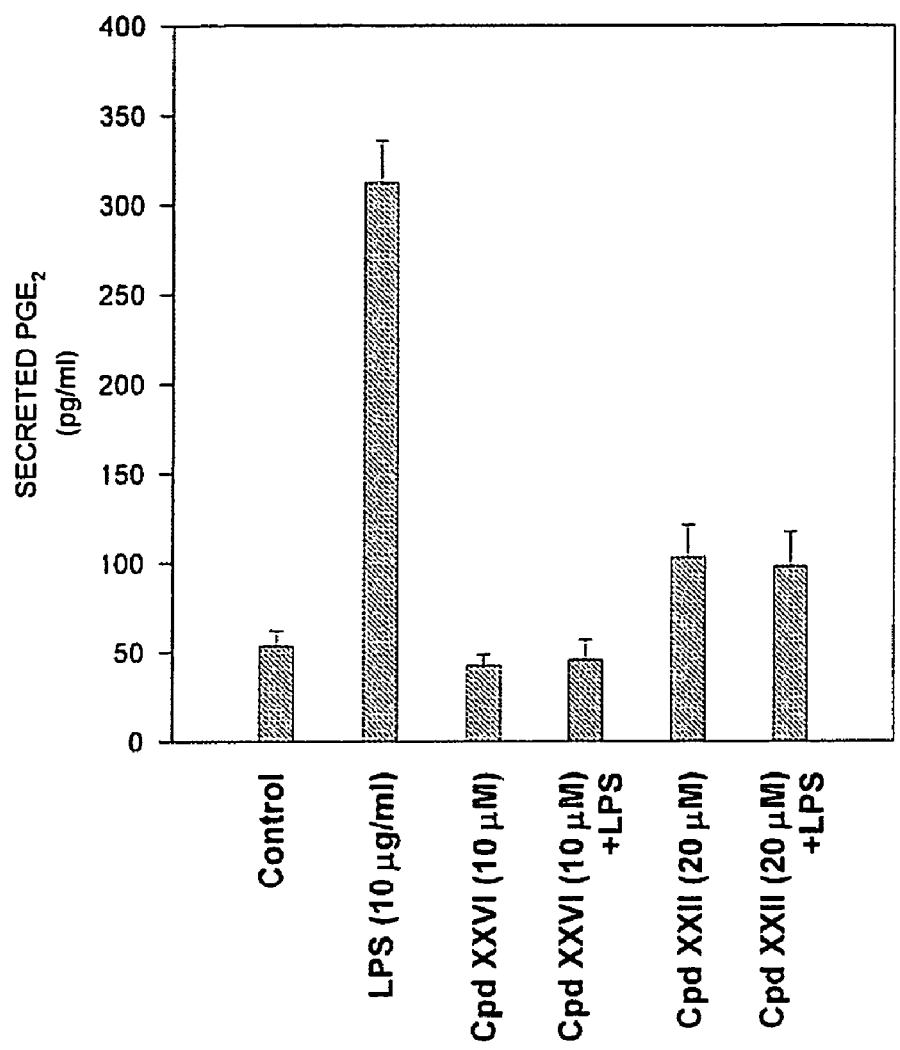

Fig. 7.2: Lipid-conjugates inhibit the secretion of $PGE_2$ from glial cells stimulated by pardaxin (PX).
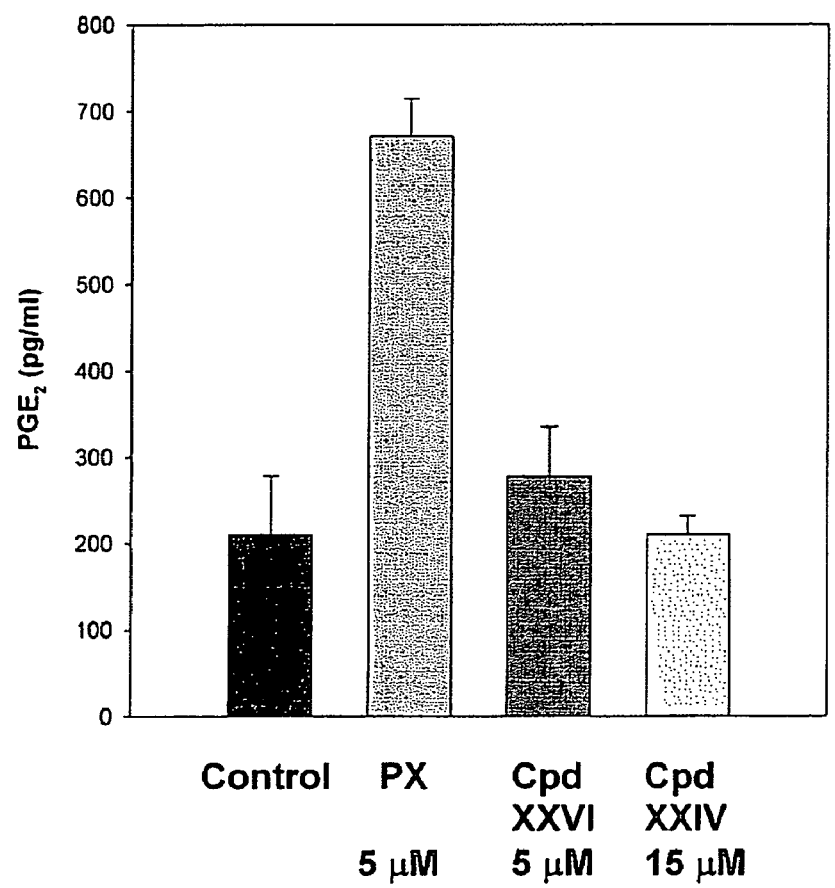

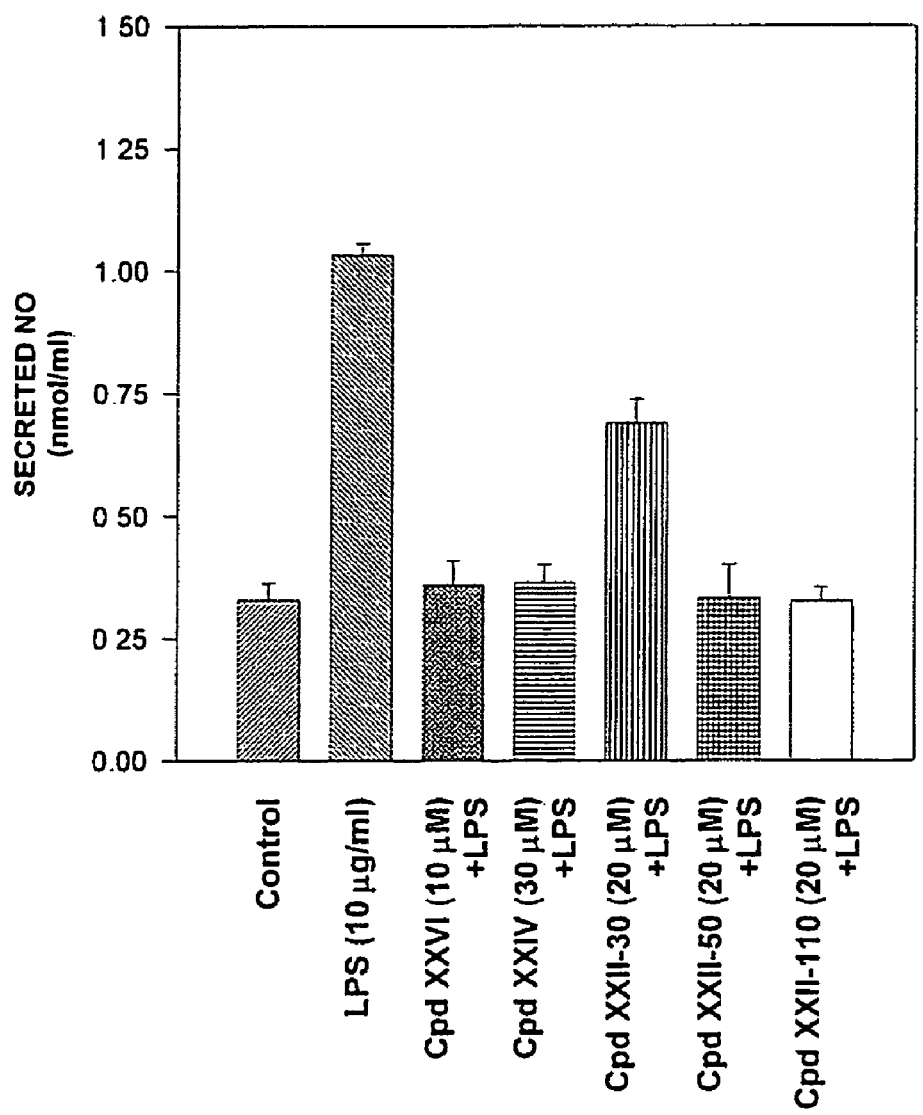
Fig. 7.3: Lipid-conjugates inhibit the production of nitric oxide by LPS-stimulated rat glial cells.

Fig. 7.4: Lipid-conjugates inhibit the production of nitric oxide by PX-stimulated PC12 cells.
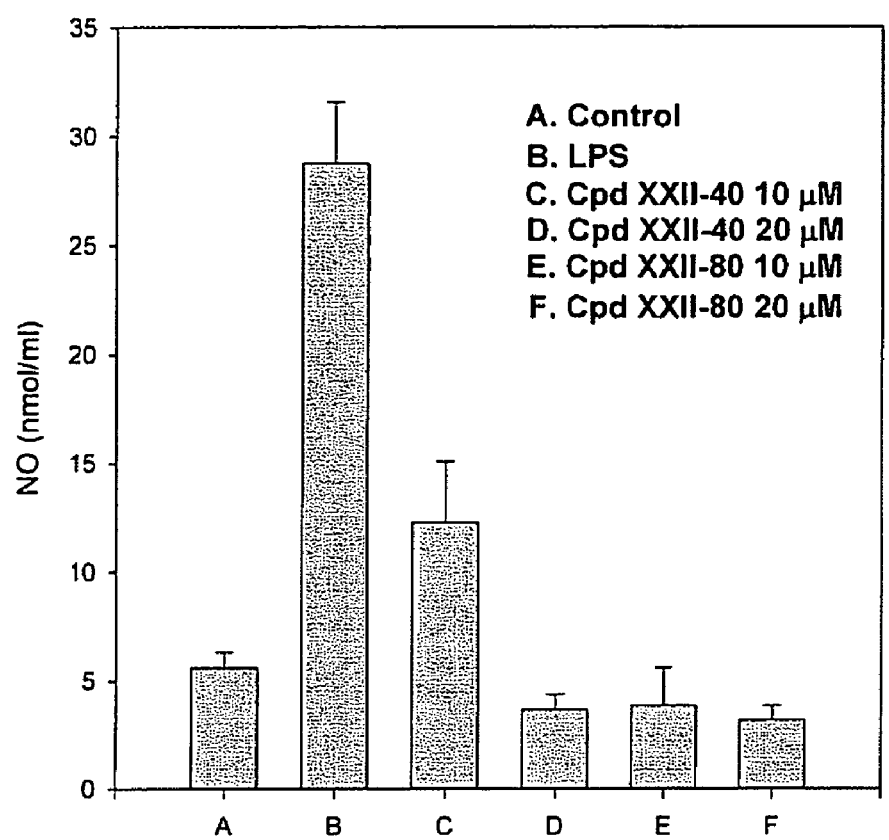

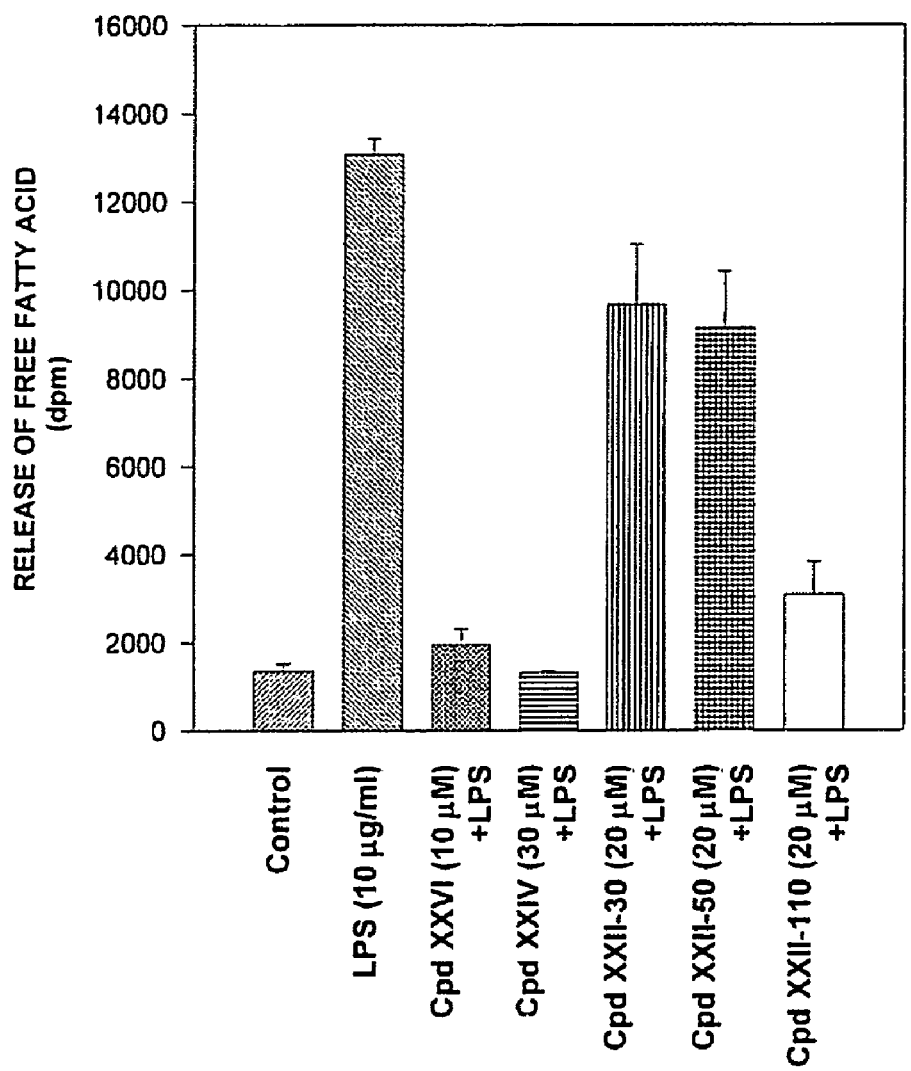
Fig. 7.5: Lipid-conjugates inhibit LPS-induced secretion of sPLA$_2$ (expressed as fatty acid release) from glial cells.

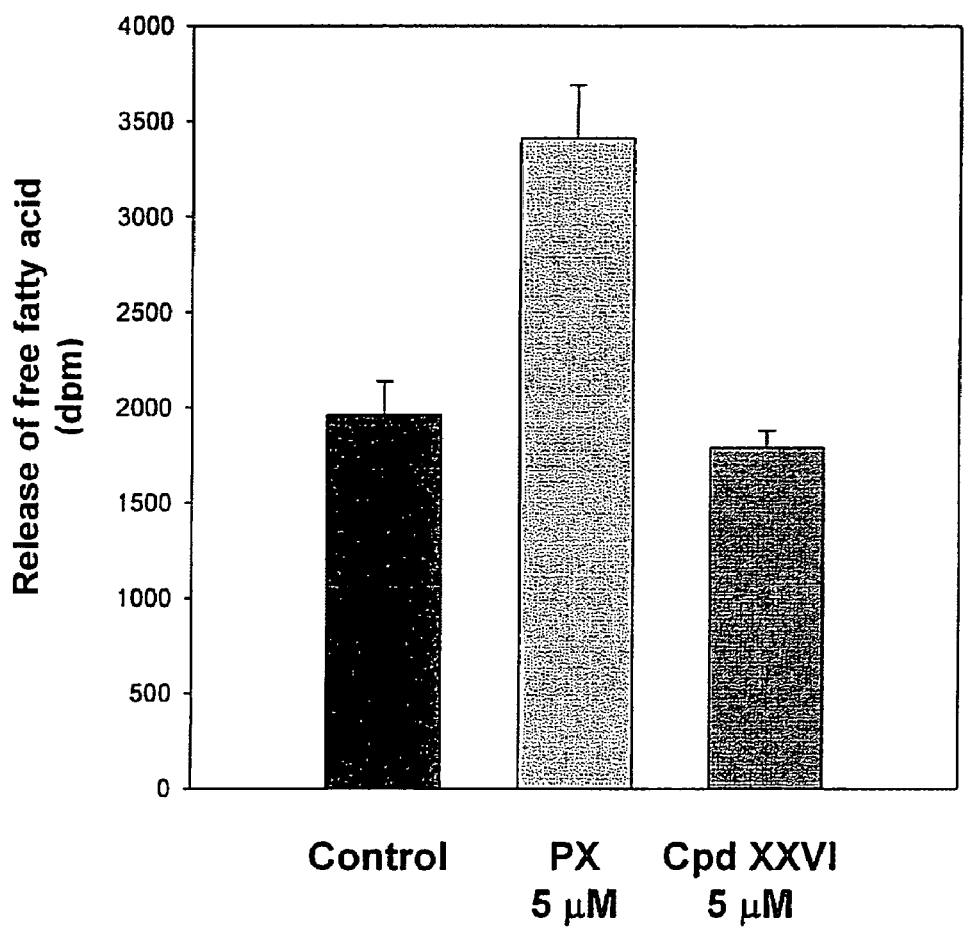
Fig. 7.6: Lipid-conjugates inhibit PX-induced activation of $PLA_2$ (expressed as fatty acid release) in PC12 cells.

Fig. 7.7: Effect of Compound XXVI on LPS-induced Oleic Acid (OA) release.
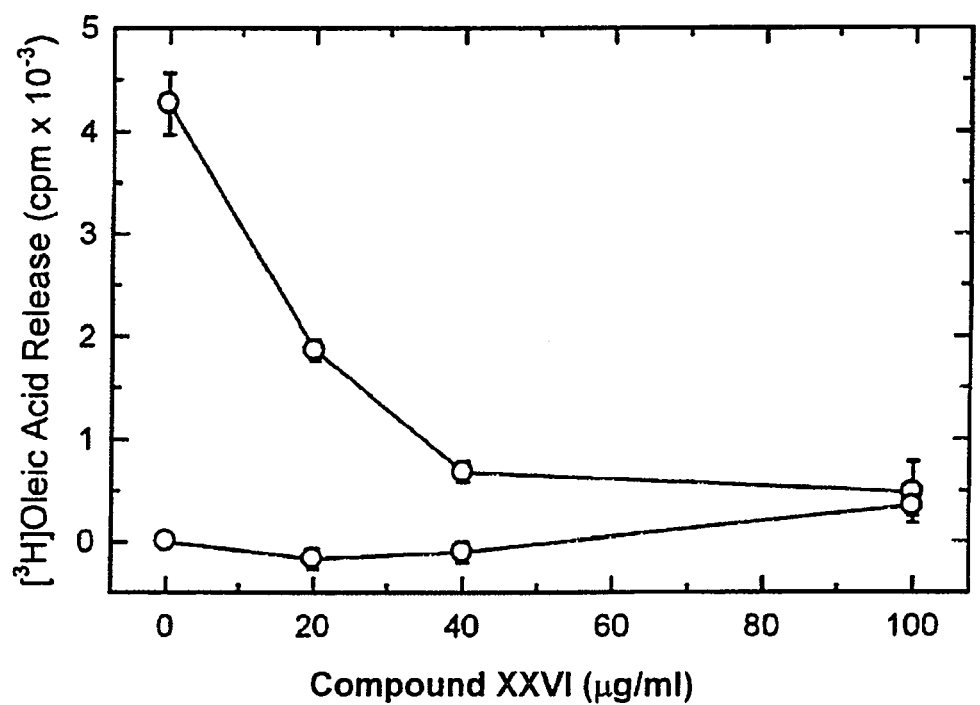

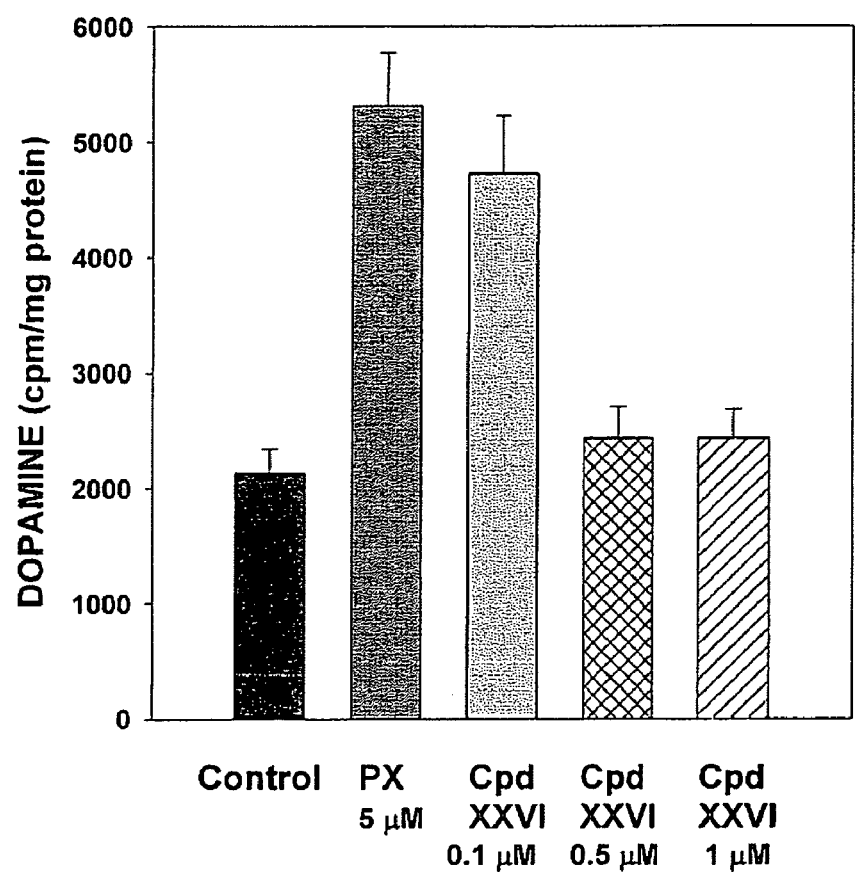
Fig. 7.8: Lipid-conjugates inhibit PX-induced dopamine release by PC12 cells.

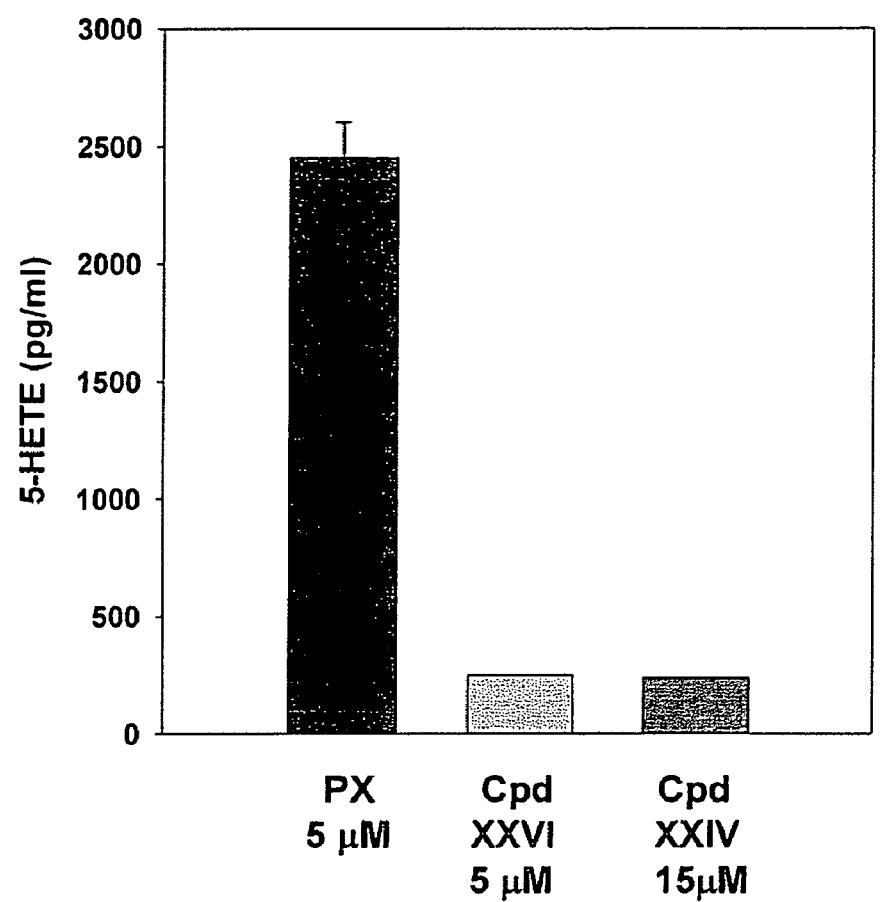
Fig. 7.9: Lipid-conjugates inhibit PX-induced production of 5-HETE by PC12 cells.

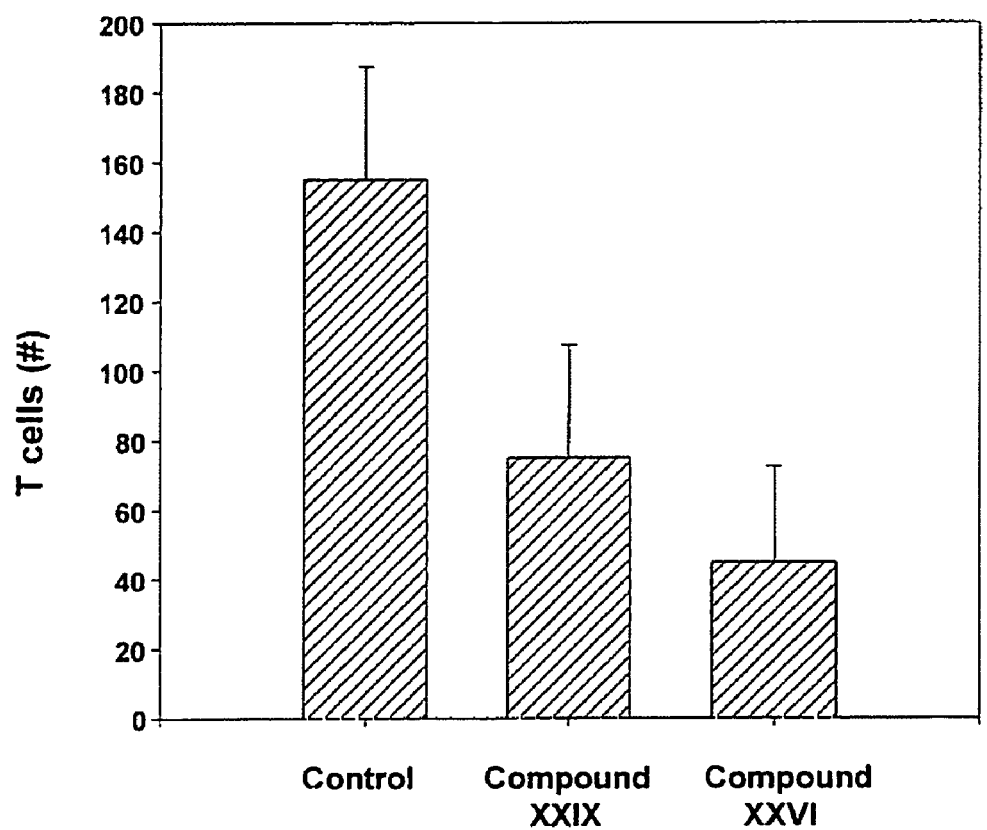
Fig. 7.10: Effect of Lipid-conjugates on T cell permeation through a monolayer of endothelial cells.

USE OF LIPID CONJUGATES IN THE TREATMENT OF INFECTION

CROSS REFERENCE TO RELATED APPLICATIONS

This application is a continuation-in-part of U.S. application Ser. No. 10/952,496 filed Sep. 29, 2004, now U.S. Pat. No. 7,393,938 and a continuation-in-part of U.S. application Ser. No. 10/627,981, filed Jul. 28, 2003, now U.S. Pat. No. 7,101,859 which are continuation-in-part applications of U.S. application Ser. No. 09/756,765, filed Jan. 10, 2001, now U.S. Pat. No. 7,034,006 which claims priority from U.S. Provisional Application Ser. No. 60/174,905, filed Jan. 10, 2000, and U.S. Provisional Application Ser. No. 60/174,907 filed Jan. 10, 2000, which are hereby incorporated by reference.

FIELD OF THE INVENTION

This invention provides compounds and methods of use thereof in suppressing, inhibiting, preventing, or treating a pathogenic effect on a cell, including, inter alia, infection with intracellular pathogens. Also provided are compounds and methods of use thereof in suppressing, inhibiting, preventing, or treating an infection in a subject.

BACKGROUND OF THE INVENTION

Lipid-conjugates are thought to inhibit the enzyme phospholipase A2 (PLA2, EC 3.1.1.4). Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Lipid-conjugates may offer a wider scope of protection of cells and organisms from injurious agents and pathogenic processes, including the prevention and treatment of microbial infections.

Microbial infections (e.g., infections by viral or bacterial species) account for significant morbidity and mortality throughout the world. Although significant resources have been dedicated to identifying compounds having antimicrobial properties, microbial infections continue to present a significant human health risk.

There are relatively few effective pharmaceutical compositions intended or adapted for antiviral, antifungal, or antiparasitic therapy. A major obstacle in the development of antiviral agents is the difficulty in distinguishing viral replicative mechanisms from host replicative processes. An additional limitation of existing antiviral drugs is that they have a narrow antiviral spectrum and are often ineffective against the latent virus.

There are a much larger number of existing antibacterial agents, which has led to a significant decrease in morbidity and mortality from infectious diseases in this century. This important public health contribution has been largely due to the widespread use of antibiotics that target specific nutrient, cell wall, DNA, RNA and protein biosynthetic pathways that are particular to pathogenic bacteria. However, in recent years the capacity to manage infectious diseases has been threatened by the emergence of bacterial strains that are no longer susceptible to currently available antimicrobial agents. The widespread use of available antibacterial agents has led to the development of increasing numbers of antibiotic resistant bacteria.

In fact, the usefulness of most existing antimicrobial treatments are limited by the development of multidrug resistance and the emergence of long-term toxicities. Other challenges include creating a drug that is broadly applicable in combating many different types of microbial infections, which is especially important in the treatment of immunocompromised individuals.

SUMMARY OF THE INVENTION

In one embodiment, the invention provides a method of suppressing, inhibiting, preventing, or treating a pathogenic effect on a cell, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In another embodiment, the invention provides a method of suppressing, inhibiting, preventing, or treating an infection in a subject, comprising the step of administering an effective amount of a lipid or phospholipid moiety bound to a physiologically acceptable monomer, dimer, oligomer, or polymer, and/or a pharmaceutically acceptable salt or a pharmaceutical product thereof to an infected subject.

BRIEF DESCRIPTION OF FIGURES

FIG. 1.1: Effect of Lipid-conjugates on HIV infectivity.

FIG. 2.1: Effect of Lipid-conjugates on injection of HeLa cells by *Chlamydia*.

FIG. 2.2: Effect of Lipid-conjugates on *Chlamydia*-induced apoptosis of HeLa cells.

FIG. 3.1: Inhibition of endothelin-1 (ET)-induced contraction of rat tracheal rings by Lipid-conjugates. A: Contraction of rat trachea by Endothelin-1. B: Effect of a Lipid-conjugate on ET-induced contraction of rat trachea.

FIG. 3.2: Effect of Lipid-conjugates on ET-1 induced contraction of rat trachea.

FIG. 3.3: Effect of Lipid-conjugates on Acetylcholine (AcCh)-induced contraction of isolated rat trachea rings.

FIG. 3.4: Effect of a Lipid-conjugate, administered subcutaneously, on early asthmatic reaction (EAR) induced by ovalbumin (OVA) inhalation.

FIG. 3.5: Effect of a Lipid-conjugate on $sPLA_2$ expression in lung of rats with OVA-induced asthma.

FIG. 3.6: Effect of a Lipid-conjugate on cysteinyl leukotriens ($LTC_4$, $LTD_4$ and $LTE_4$) level in the broncho-alveolar lavage (BAL) of OVA-induced asthmatic rats.

FIG. 3.7: Effect of Lipid-conjugate inhalation on early and late asthmatic reaction (EAR and LAR, respectively) in OVA-sensitized asthmatic rats.

FIG. 3.8: Effect of Lipid-conjugate inhalation on cysteinyl leukotriens (LTC4, LTD4 and LTE4) level in the BAL of OVA-sensitized asthmatic rats.

FIG. 3.9: Effect of Lipid-conjugate inhalation on NO production by macrophages collected from the BAL of OVA-sensitized asthmatic rats.

FIG. 3.10: Effect of Lipid-conjugate inhalation on structural change in airways (airway remodeling) of OVA-sensitized asthmatic rats.

FIG. 3.11: Effect of a Lipid-conjugate on the remodeling of asthmatic rat airway; histological morphometry.

FIG. 3.12: Effect of Lipid-conjugate inhalation on TNFα production by macrophages collected from the BAL of OVA-sensitized asthmatic rats.

FIG. 3.13: Amelioration of OVA-induced broncho-constriction by Lipid-conjugate inhalation before challenge.

FIG. 3.14: Amelioration of OVA-induced broncho-constriction by Lipid-conjugate inhalation after challenge.

FIG. 4.1 I-II: Effect of Lipid-conjugates on LPS-induced production of TNFα in human whole blood.

FIG. 4.2: Effect of a Lipid-conjugate on rat survival in LPS-induced endotoxinemia.

FIG. 4.3: Effect of a Lipid-conjugate on serum levels of TNF-α and IL-6 in septic rats.

FIG. 4.4: Effect of a Lipid-conjugate on TNF-α production after i.p. administration of LPS and simultaneous i.v. administration of a Lipid-conjugate.

FIG. 4.5: Effect of a Lipid-conjugate on serum cytokine levels in rats injected with LPS or LPS+LTA.

FIG. 4.6: Effect of a Lipid-conjugate on mRNA expression of IL-1, TNF-α and IL-6 genes in lung and kidney of rats with LPS-induced sepsis.

FIG. 4.7: Effect of a Lipid-conjugate on mRNA expression of $sPLA_2$-IIA and iNOS genes in kidney and lung of rats with LPS-induced sepsis.

FIG. 4.8: Effect of a Lipid-conjugate on ICAM-1 expression in lung and kidney of rats with LPS-induced sepsis.

FIG. 6.1: A Lipid-conjugate protects BGM cells from membrane lysis induced by combined action of hydrogen peroxide produced by glucose oxidase (GO) and exogenous phospholipase $A_2$ ($PLA_2$).

FIG. 6.2: A Lipid-conjugate protects BGM cells from glycosaminoglycan degradation by hydrogen peroxide produced by glucose oxidase (GO).

FIG. 6.3: A Lipid-conjugate protects LDL from copper-induced oxidation.

FIG. 7.1: Lipid-conjugates inhibit the secretion of $PGE_2$ from glial cells stimulated by LPS.

FIG. 7.2: Lipid-conjugates inhibit the secretion of $PGE_2$ from glial cells stimulated by pardaxin (PX).

FIG. 7.3: Lipid-conjugates inhibit the production of nitric oxide (NO) by LPS-stimulated rat glial cells.

FIG. 7.4: Lipid-conjugates inhibit the production of nitric oxide (NO) by PX-stimulated PC12 cells.

FIG. 7.5: Lipid-conjugates inhibit the secretion of LPS-stimulated $sPLA_2$ (expressed as fatty acid release) from glial cells.

FIG. 7.6: Lipid-conjugates inhibit PX-induced activation of $PLA_2$ (expressed as fatty acid release) in PC12 cells.

FIG. 7.7: Effect of a Lipid-conjugate on LPS-induced oleic acid (OA) release.

FIG. 7.8: Lipid-conjugates inhibit PX-induced dopamine release by PC12 cells.

FIG. 7.9: Lipid-conjugates inhibit PX-induced production of 5-HETE by PC12 cells.

FIG. 7.10: Effect of Lipid-conjugates on T-cell permeation through a monolayer of endothelial cells.

DETAILED DESCRIPTION OF THE INVENTION

Methods of Treating Disease Based on Phospholipid Conjugates

In one embodiment, the invention provides a method of suppressing, inhibiting, preventing, or treating a pathogenic effect on a cell, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In one embodiment, the compounds for use in the present invention (for e.g., a lipid or phospholipid moiety bound to a physiologically acceptable monomer, dimer, oligomer, or polymer) are referred to herein as "Lipid-conjugates".

In one embodiment, "suppressing, inhibiting, preventing, or treating" refers to delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics.

In one embodiment, symptoms are primary, while in another embodiment, symptoms are secondary. In one embodiment, "primary" refers to a symptom that is a direct result of infection with a pathogen, while in one embodiment, "secondary" refers to a symptom that is derived from or consequent to a primary cause. In another embodiment, "symptoms" may be any manifestation of a disease or pathological condition, comprising inflammation, swelling, fever, pain, bleeding, itching, runny nose, coughing, headache, migraine, difficulty breathing, weakness, fatigue, drowsiness, weight loss, nausea, vomiting, constipation, diarrhea, numbness, dizziness, blurry vision, muscle twitches, convulsions, etc., or a combination thereof.

In one embodiment, "treating" refers to both therapeutic treatment and prophylactic or preventative measures, wherein the object is to prevent or lessen the targeted pathologic condition or disorder as described hereinabove. Thus, in one embodiment, treating may include suppressing, inhibiting, preventing, treating, or a combination thereof.

In one embodiment, a pathogenic effect is apoptosis, necrosis, membrane blebbing/protrusion, cell death, permeabilized cell membrane, cell enlargement, dilated organelles, ribosome dissociation from endoplasmic reticulum, nuclear disintegration, chromatin condensation, pyknotic or fragmented nuclei, leakage of cellular contents, tissue inflammation, expression of apoptosis-specific proteins, cell shrinkage, formation of apoptotic bodies, expression of pathogen antigens, granularity, ragged edges, filmy appearance, cell rounding or a combination thereof. In another embodiment, a pathogenic effect is caused by infection with any of the pathogens described hereinbelow. In one embodiment, a pathogenic effect is a cytopathic effect.

Thus, in one embodiment of the present invention, the compounds for use in the present invention are directed towards the resolution of symptoms of a disease or disorder that result from a pathogenic infection as described hereinabove. In another embodiment, the compounds affect the pathogenesis underlying the pathogenic effect described hereinabove.

In one embodiment, a pathogenic effect on a cell could be a cell of any tissue, in one embodiment, a vertebrate cell, in another embodiment, a mammalian cell, and in another embodiment, a human cell. In one embodiment, a pathogen may infect a plurality of cell types, tissues or organs. In another embodiment, pathogens have preference for infecting specific cell types, tissues, or organs. It is to be understood that agents of the present invention may be efficacious in treating any cell type in which the pathogen may exert an effect. In one embodiment, a compound for use in the present invention may localize to or act on a specific cell type. In one embodiment, a compound for use in the present invention may be cytoprotective. In one embodiment a compound for use in the present invention may be inserted or partially inserted into a cell membrane. In another embodiment a compound for use in the present invention may be effective in treating a plurality of cell types.

In another embodiment, the cell exhibiting a pathogenic effect described hereinabove is present in a subject with a pathogenic infection.

In one embodiment, the invention provides a method of treating a subject suffering from a pathogenic effect, including, inter, alia, the step of administering to a subject an effective amount of a lipid or phospholipid moiety bonded to a physiologically acceptable monomer, dimer, oligomer, or polymer, thereby treating the subject suffering from a pathogenic effect.

In another embodiment, the invention provides a method of suppressing, inhibiting, preventing, or treating an infection in a subject comprising the step of administering to said subject an effective amount of a lipid or phospholipid moiety bound to a physiologically acceptable monomer, dimer, oligomer, or polymer, and/or a pharmaceutically acceptable salt or a pharmaceutical product thereof.

In another embodiment, the invention provides a method of treating a subject suffering from a pathogenic infection, comprising the step of administering to a subject any one of the compounds for use in the present invention, or any combination thereof, in an amount effective to treat the subject suffering from a pathogenic infection.

In one embodiment, the pathogenic effect is due to an infection of the cell described hereinabove by a pathogen. In one embodiment, the pathogen is a virus and in another embodiment, the pathogen is a bacterium. In one embodiment, the pathogenic effect is the result of a viral infection and in another embodiment, the pathogenic effect is the result of a bacterial infection. In another embodiment, the pathogenic effect is the result of an infection with influenza, HIV, poxvirus, chlamydia, or a combination thereof, as is described hereinbelow.

In another embodiment, the pathogenic effect is due to a cytopathic effect of a pathogen in a cell. In another embodiment, the pathogenic effect in the cell is due to a cell-to-cell spread of a pathogen. In another embodiment, the pathogenic effect is the result of obstructive respiratory disease, cytokine overproduction, sepsis, hemolysis, oxidative injury, central nervous system insult, conjunctivitis, or a combination thereof, as is described hereinbelow. In another embodiment, the pathogenic effect is the result of cancer. In another embodiment, the pathogenic effect is due to toxic products produced by the pathogen. In one embodiment, the toxic product may be worm eggs.

In one embodiment, the invention provides a method of treating a subject suffering from a viral infection, including, inter alia, the step of administering to a subject an effective amount of a lipid or phospholipid moiety bonded to a physiologically acceptable monomer, dimer, oligomer, or polymer, thereby treating the subject suffering from a viral infection.

In one embodiment, the invention provides a method of treating a subject suffering from a bacterial infection, including, inter alia, the step of administering to a subject an effective amount of a lipid or phospholipid moiety bonded to a physiologically acceptable monomer, dimer, oligomer, or polymer, thereby treating the subject suffering from a bacterial infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a viral infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a bacterial infection.

In another embodiment, the viral pathogenic effect, infection, or combination thereof is mediated by any one or more of the following pathogens: hepatitis B virus, hepatitis C virus, human immunodeficiency virus, human herpesviruses, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirs, poliovirus, human respiratory syncytial virus, retrovirus, human T-cell leukemia virus, rabies virus, mumps virus, malaria (*Plasmodium falciparum*), Bordetelia pertussis, Diptheria, Rickettsia prowazekii, Borrelia bergdorferi, Ebola virus. In one embodiment, the viral pathogenic effect, infection or combination thereof is mediated by Pichinde virus, while in another embodiment, it is mediated by Punta Toro virus.

In one embodiment, the pathogenic effect, infection or combination thereof is mediated by one or more of the following pathogens: Helminths, *Bacillus anthracis* (anthrax), *Clostridium botulinum, Yersinia pestis*, Variola major (smallpox) and other pox viruses, *Francisella tularensis* (tularemia), Arenaviruses, Lymphocytic choriomeningitis, Junin virus, Machupo virus, Guanarito virus, Lassa Fever, Bunyaviruses, Hantaviruses, Rift Valley Fever, Flaviruses, Dengue, Filoviruses, Ebola, Marburg, hemorrhagic fever viruses, Tickborne hemorrhagic fever viruses, Crimean-Congo Hemorrhagic fever virus, Tickbome encephalitis viruses, Yellow fever, Tuberculosis, Multi-drug resistant tuberculosis, Influenza, Rickettsias, Rabies virus, Severe acute respiratory syndrome-associated coronavirus (SARS), *Burkholderia pseudomallei, Coxiella burnetii* (Q fever), *Brucella* species (brucellosis), *Burkholderia mallei* (glanders), Ricin toxin (from *Ricinus communis*), Epsilon toxin of *Clostridium perfringens, Staphylococcus* enterotoxin B, Typhus fever (*Rickettsia prowazekii*), Diarrhieagenic *E. coli*, Pathogenic Vibrios, *Shigella* species, *Salmonella, Listeria monocytogenes, Campylobacter jejuni, Yersinia enterocolitica*), Caliciviruses, Hepatitis A, *Cryptosporidium parvum, Cyclospora cayatanensis, Giardia lamblia, Entamoeba histolytica, Toxoplasma*, Microsporidia, West Nile Virus, LaCrosse, California encephalitis, Western Equine Encephalitis, Eastern Equine Encephalitis, Venezuelan Equine Encephalitis, Japanese Encephalitis Virus, and Kyasanur Forest Virus.

In another embodiment, the pathogenic effect, infection, or combination thereof is mediated by one or more of the following microorganisms: *Actinobacillus pleuropneumoniae, Aeropyrum pernix, Agrobacterium tumeficians, Anopheles gambiae, Aquifex aeolicus, Arabidopsis thaliana, Archeglobus fulgidis, Bacillus anthracis, bacillus cereus, Baccilus halodurans, Bacillus subtilis, Bacteroides thetaiotaomicron, Bdellovibrio bacteriovorus, Bifidobacterium longum, Bordetella bronchiseptica, Bordetella pertussis, Borrelia burgdorferi, Bradyhizobium japonicum, Brucella melitensis, Burcella suis, Bruchnera aphidicola, Brugia malayi, Caenorhabditis elegans, Canipylobacter jejuni, Candidatus blochmanniafloridanus, Caulobacter crescentus, Chlorobium tepidum, Chromobacterium violaceum, Clostridium acetobutylicum, Clostridium perfringens, Clostridium tetani, Corynebacterium diphtheriae, Corynebacterium efficiens, Corynebacterium tetani, Corynebacterium burnetii, Danio* rerio, Dechloromonas aromatica, Deinococcus radiodurans, Drosophila melanogaster, Eimeria tenella, Eimeria acervulina, Entamoeba histolytica, Enterococcus faecalis, Escherichia coli, Fusobacterium nucleatum, Geobacter subrurreducens, Gloeobacter violaceus, Haemophilis ducreyi, Haemophilis influenzae, Halobacterium, Heliobacter hepaticus, Helicobacter pylori, Lactobacillus johnsonii, Lactobacillus plantorum, Lactococcus lactis, Leptospira interrogans serovar lai, Listeria innocua, Listeria monocytogenes, Mesorhizobium loti, Methanobacter thermoautrophicus, Methanocaldocossus jannaschii, Methanosareina mazei Goel, Methanopyrus kandleri, Methanosarcina acetivorans, Methanosareina mazei Goel Mycobacterium avium, Mycobacterium bovis, Mycobacterium leprae, Mycobacterium tuberculosis, Mycoplasma gallisepticum strain R, Mycoplasma genitalium, Mycoplasma penetrans, Mycoplasma pneumoniae, Mycoplasma pulmonis, Nanoarchaeum equitans, Neisseria meningitidis, Nitrosomonas europaea, Nostoe, Oceanobacillus iheyensis, Onion yellows phytoplasma, Oryzias latipes, Oryza sativa, Pateurella multocida, Photorhabdus luminescens, Pirellula, Plasmodium falciparum, Plasmodium vivax, Plasmodium yoelii, Porphyromonas gingivalis, Prochlorococcus marinus, Pseudomonas aeruginosa, Pseudomonas putida, Pseudomonas syringae, Pyrobaculum aerophilium, Pyrococcus abyssi, Pyrococcus furiosus, Pyrococcus horikoshii, Ralstonia solanacearum, Rhodopseudomonas palustris, Rickettsia conorii, Rickettsia prowazekii, Rickettsia rickettsii, Saccharomyces cerevisiae, Salmonella enterica, Salmonella typhimurium, Sarcocystis cruzi, Schistosoma mansoni, Schizosaccharomyces pombe, Shewanella oneidensis, Shigella flexneri, Sinorhizobium meliloti, Staphylococcus aureus, Staphylococcus epidermis, Streptococcus agalactiae, Streptococcus agalactiae, Streptococcus mutans, Streptococcus pneumoniae, Streptococcus pyogenes, Streptomyces avermitilis, Streptomyces coelicolor, Suffiblobus tokodaii, Synechocystis sp., Takifugu rubripes, Tetraodon fluviatilis, Theileria purva, Thermoanaerobacter tengcongensis, Thernzoplasma acidophilum, Thermoplasma voleanium, Thermosynechoccus elongatus, Aermotoga maritima, Toxoplasma gondii, Treponema denticola, Treponema pallidum, Tropheryma whipplei, Tryponosoma brucei Trypanosoma cruzi, Ureaplasma urealyticum, Vibrio cholerae, Vibro parahaemolyticus, Pbro vulnificus, Wigglesworthia brevipalpis, Wolbachia endosymbiont of Drosophilia melanogaster, W01inella succinogenes, Xanthomonas axonopodis pv. Citri, Xanthomonas campestris pv. Campestris, Xylella fastidiosa, or Yersinia pestis.

In one embodiment, the pathogenic effect, infection or combination thereof is mediated by a parasite. In one embodiment, the parasite is a worm. In one embodiment, the parasitic worm is a helminth, Acanthocephala, Clonorchis sinensis (the Chinese liver fluke), Dracunculiasis (Guinea Worm Disease), or Enterobius vermicularis (pinworm). In another embodiment, the parasite is a fish, which is, in one embodiment, a Candiru (Vampire fish of Brazil). In another embodiment, the parasite is a fungi, which is, in one embodiment, a Tinea (ringworm). In one embodiment, the parasite is a protist. In one embodiment, the protist parasite is a Plasmodium (malaria), Balantidium coli, or Giardia lamblia. In one embodiment, the parasite is Hirudinea (leech), Phthiraptera (lice), Siphonaptera (fleas), or Acarina (ticks).

In another embodiment, the parasite is an intracellular bacterial parasite. In one embodiment, the intracellular bacterial parasite is Rickettsias, while in another embodiment, it's Mycobacterium leprae. In one embodiment, the intracellular bacterial parasite is Rickettsia prowazekii, while in another embodiment, it's Rickettsia rickettsii (Rocky mountain spotted fever).

In one embodiment, the methods of the present invention may be used to treat a pathogenic infection acquired via zoonotic transmission. In one embodiment, the methods of the present invention may be used to treat pathogenic infections acquired from avian, swine, bovine, or bat. In another embodiment, the methods of the present invention may be used to treat Menangle, Hendra, Australian Bat Lyssavirus, Nipah, or Tioman. In another embodiment, the methods of the present invention may be used to diminish pathogen reservoirs in animal species. In another embodiment, the methods of the present invention may be used to treat a human infected with a pathogen.

HIV

In another embodiment, the viral pathogenic effect described hereinabove is mediated by Human Immunodeficiency Virus (HIV). In another embodiment, the infection described hereinabove is mediated by HIV.

In one embodiment, the methods of the present invention comprise treating secondary complications of HIV infection. In another embodiment, the methods comprise treating opportunistic infections, neoplasms, neurologic abnormalities, or progressive immunologic deterioration. In another embodiment, the methods comprise treating acquired immunodeficiency syndrome. In another embodiment, the methods comprise treating a decline in the number of CD4$^+$ T lymphocytes.

In another embodiment, methods comprise treating HIV transmitted by direct sexual contact, either homosexual or heterosexual; by blood or blood products; or from an infected mother to infant, either intrapartum, perinatally, or via breast milk.

In one embodiment, the methods of the present invention may be used to treat HIV or related infections that were acquired via zoonotic transmission. In one embodiment, the methods of the present invention may be used to treat simian immunodeficiency virus.

In one embodiment, methods of treating infection comprise treating Clade A, B, C, D, A/E, F, G, H, J, or K. In another embodiment, the viral pathogenic effect, infection or combination thereof is mediated by HIV-1, while in another embodiment, it's mediated by HIV-2. In one embodiment, it's mediated by the M group of HIV-1, in another embodiment, it's mediated by the O group of HIV-1, while in another embodiment, it's mediated by the N group of HIV-1. In one embodiment, it's mediated by the A clade (or subtype) of the M group of HIV-1, in another embodiment, it's mediated by the B clade of the M group of HIV-1, in another embodiment, it's mediated by the C clade of the M group of HIV-1, in another embodiment, it's mediated by the D clade of the M group of HIV-1, in another embodiment, it's mediated by the A/E clade of the M group of HIV-1, in another embodiment, it's mediated by the F clade of the M group of HIV-1, in another embodiment, it's mediated by the G clade of the M group of HIV-1, in another embodiment, it's mediated by the H clade of the M group of HIV-1, in another embodiment, it's mediated by the J clade of the M group of HIV-1, in another embodiment, it's mediated by the K clade of the M group of HIV-1, in another embodiment, it's mediated by the A/G/I clade of the M group of HIV-1, while in another embodiment, it's mediated by a circulating recombinant form (CRF) of any of the above clades.

In one embodiment, methods of treating infection comprise treating a macrophage-tropic strain of HIV, T cell-tropic strain of HIV, or any combination thereof. In one embodiment, the compounds for use in the present invention will treat infection mediated by a macrophage-tropic strain of HIV. In another embodiment, the compounds will treat infection mediated by a T cell-tropic strain of HIV. In another embodiment, the compounds will treat infection mediated by either a macrophage-tropic strain of HIV, a T cell-tropic, or both. In another embodiment, the mechanism of action of the compounds for use in the present invention differ based on the tropism of HIV.

In another embodiment, this invention provides a method of suppressing, inhibiting, preventing, or treating an HIV infection in a subject comprising the step of administering to said subject an effective amount of a lipid or phospholipid moiety bound to a physiologically acceptable monomer, dimer, oligomer, or polymer, and/or a pharmaceutically acceptable salt or a pharmaceutical product thereof. In one embodiment, the phospholipid moiety is phosphatidylethanolamine and the physiologically acceptable monomer, dimer, oligomer, or polymer is a glycosaminoglycan. In another embodiment, the phospholipid moiety is dipalmitoyl phosphatidylethanolamine and the physiologically acceptable monomer, dimer, oligomer, or polymer is heparin. In another embodiment, the phospholipid moiety is dipalmitoyl phosphatidylethanolamine and the physiologically acceptable monomer, dimer, oligomer, or polymer is chondroitin sulfate. In another embodiment, the phospholipid moiety is dipalmitoyl phosphatidylethanolamine and the physiologically acceptable monomer, dimer, oligomer, or polymer is hyaluronic acid. In another embodiment, the phospholipid moiety is dimyristoyl phosphatidylethanolamine and the physiologically acceptable monomer, dimer, oligomer, or polymer is hyaluronic acid.

In another embodiment, the invention provides a method of suppressing, inhibiting, preventing, or treating an HIV infection in a cell, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In one embodiment, the invention provides a method of treating a subject suffering from an HIV infection, including, in inter alia, the step of administering to a subject an effective amount of a lipid or phospholipid moiety bonded to a physiologically acceptable monomer, dimer, oligomer, or polymer, thereby treating the subject suffering from an HIV infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with an HIV infection.

In one embodiment, Lipid-conjugates of the present invention suppress, inhibit, prevent, or treat HIV infection. In another embodiment, Lipid-conjugates decrease HIV virus titer. This is exemplified in FIG. 1.1 and represents an embodiment of this invention. In another embodiment, Lipid-conjugates inhibit p24 production. This is exemplified in Tables 1.1-1.2 and represents an embodiment of this invention. In another embodiment, Lipid-conjugates inhibit fusion of HIV-infected cells to non-HIV-infected cells. This is exemplified in Tables 1.3-1.4 and represents an embodiment of this invention. In another embodiment, Lipid-conjugates decrease V3 antibody binding. This is exemplified in Table 1.5 and represents an embodiment of this invention. In one embodiment, Compound XXII (see compound descriptions hereinbelow) is useful to treat HIV infection. This is exemplified in Tables 1.1, 1.2, and 1.5 and represents an embodiment of this invention. In another embodiment, Compound XXV (see compound descriptions hereinbelow) is useful to treat HIV infection. This is exemplified in Tables 1.1, 1.2, and 1.5 and represents an embodiment of this invention. In another embodiment, Compound XXIII (see compound descriptions hereinbelow) is useful to treat HIV infection. This is exemplified in Tables 1.1-1.5 and represents an embodiment of this invention. In another embodiment, Compound XXIV (see compound descriptions hereinbelow) is useful to treat HIV infection. This is exemplified in Tables 1.1-1.5 and represents an embodiment of this invention.

Influenza

In one embodiment, the viral pathogenic effect described hereinabove is mediated by influenza virus: In another embodiment, the infection described hereinabove is mediated: by influenza virus.

Thus, in one embodiment, the methods of the present invention include the treatment of symptoms of infection by influenza virus comprising fever (usually high), headache, tiredness (can be extreme), cough, sore throat, runny or stuffy nose, body aches, diarrhea, vomiting, or a combination thereof.

In one embodiment, the methods of the present invention treat secondary complications related to influenza infection, which may comprise, inter alia, bacterial pneumonia, bronchitis, dehydration, sinus infections, and ear infections. In another embodiment, the methods of the present invention treat chronic health problems that are exacerbated in a subject with influenza infection which may comprise, inter alia, asthma.

In one embodiment, influenza viruses for treatment by the methods of the present invention may be of type A or type B. In one embodiment, the viral pathogenic effect, infection, or combination thereof is mediated by Influenza Type A virus, in another embodiment, it's mediated by Influenza Type B virus, while in another embodiment, it's mediated by Influenza Type C virus. In one embodiment, it's mediated by H1N1 strain of Influenza Type A, in another embodiment, it's mediated by H2N2 strain of Influenza Type A, in another embodiment, it's mediated by H3N2 strain of Influenza Type A, while in another embodiment, it's mediated by H5N1 strain of Influenza Type A. In one embodiment, it's mediated by any combination of strains of the subtypes listed hereinabove.

In one embodiment, the methods of the present invention may be used to treat influenza infections that were acquired via zoonotic transmission. In one embodiment, the methods of the present invention may be used to treat zoonotic avian influenza or zoonotic swine influenza.

In another embodiment, the invention provides a method of suppressing, inhibiting, preventing, or treating an influenza infection in a subject comprising the step of administering to said subject an effective amount of a lipid or phospholipid moiety bound to a physiologically acceptable monomer, dimer oligomer, or polymer, and/or a pharmaceutically acceptable salt or a pharmaceutical product thereof. In one embodiment, the phospholipid moiety is phosphatidylethanolamine and the physiologically acceptable monomer, dimer, oligomer, or polymer is a glycosaminoglycan. In another embodiment, the phospholipid moiety is dipalmitoyl phosphatidylethanolamine and the physiologically acceptable monomer, dimer, oligomer, or polymer is heparin. In another embodiment, the phospholipid moiety is dipalmitoyl phosphatidylethanolamine and the physiologically acceptable monomer, dimer, oligomer, or polymer is chondroitin sulfate. In another embodiment, the phospholipid moiety is dipalmitoyl phosphatidylethanolamine and the physiologically acceptable monomer, dimer, oligomer, or polymer is hyaluronic acid. In another embodiment, the phospholipid moiety is dimyristoyl phosphatidylethanolamine and the physiologically acceptable monomer, dimer, oligomer, or polymer is hyaluronic acid.

In another embodiment, the invention provides a method of suppressing, inhibiting, preventing, or, treating an influenza infection of a cell, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In one embodiment, the invention provides a method of treating a subject afflicted with an influenza infection, including, inter alia, the step of administering to a subject an effective amount of a lipid or phospholipid moiety bonded to a physiologically acceptable monomer, dimer, oligomer, or polymer, thereby treating the subject afflicted with an influenza infection.

In another embodiment, the invention provides a use of a lipid or phospholipid moiety bonded to a physiologically acceptable monomer, dimer, oligomer, or polymer, in the preparation of a pharmaceutical composition for treating a subject afflicted with an influenza infection.

In one embodiment, Lipid-conjugates of the present invention suppress, inhibit, prevent, or treat influenza infection. In another embodiment, Lipid-conjugates decrease morphological changes that result from cytotoxicity of influenza infection. This is exemplified in Example 1.4 and represents an embodiment of this invention. In another embodiment, Lipid-conjugates decrease cell membrane permeability as is demonstrated by a neutral red dye uptake assay. This is exemplified in Example 1.4 and represents an embodiment of this invention. In one embodiment, Compound XXIV (see compound descriptions hereinbelow) is useful to treat infection with influenza, in another embodiment, influenza Type A, while in another embodiment, influenza Type A, Strain H1N1. This is exemplified in Tables 1.7 and 1.9 and represents an embodiment of this invention.

Poxvirus

In one embodiment, the viral pathogenic effect described hereinabove is mediated by poxviridae, while in another embodiment, the viral pathogenic effect is mediated by chordopoxvirinae. In another embodiment, the infection described hereinabove is mediated by poxviridae while in another embodiment, the infection is mediated by chordopoxvirinae.

In one embodiment, a range of pox viruses cause febrile illnesses in man and animals with a prominent vesicular rash. In one embodiment, "pox virus", "poxvirus" and "Poxviridae" refer to the Poxyiridae family of viruses.

In one embodiment, methods of the present invention comprise treating secondary complications of infection, which may comprise progressive necrosis at the site of infection, skin disorders such as eczema, vesicular rash, neurological complications, conjunctivitis, or a combination thereof.

In one embodiment, methods of the present invention comprise treating variola major or variola minor. In another embodiment, the methods of the present invention comprise treating ordinary, modified, flat, and hermorrhagic types of variola major. In one embodiment, the methods of the present invention may be used to treat variola virus used as an agent of bioterrorism.

In another embodiment, the methods of the present invention may be used to treat secondary complications of variola infection comprising fever, malaise, head and body aches, vomiting, rash in the tongue and mouth, rash on the skin, pustule formation, scabbing, scarring, or a combination thereof.

In one embodiment, the methods of the present invention may be used to treat poxvirus infections that were acquired via zoonotic transmission. In one embodiment, the methods of the present invention may be used to treat Molluscum contagiosum, Cowpox, Monkey pox, pseudocowpox and orf. In one embodiment, the methods of the present invention may be used to treat ulcerative or non-ulcerating lesions (sometimes called "milkers nodules") on the hands of dairy workers or to treat a papulo-vesicular lesion on the hand, forearm or face of a subject.

In another embodiment, the viral pathogenic effect, infection or combination thereof is mediated by Vaccinia virus. In another embodiment, it's mediated by a poxvirus, while in another embodiment, it's mediated by a chordopoxvirinae. In another embodiment, it's mediated by Orf virus, Fowlpox virus, Sheep pox virus, Myxoma virus, Swinepox virus, Molluscum contagiosum virus, Yaba monkey tumor virus, *Melolontha melolontha* entomopoxvirus, *Amsacta moorei* entomopoxvirus, or *Chironomus luridus* entomopoxvirus.

In another embodiment, the invention provides a method of suppressing, inhibiting, preventing, or treating a vaccinia infection in a subject comprising the step of administering to said subject an effective amount of a lipid or phospholipid moiety bound to a physiologically acceptable monomer, dimer, oligomer, or polymer, and/or a pharmaceutically acceptable salt or a pharmaceutical product thereof. In one embodiment, the phospholipid moiety is phosphatidylethanolamine and the physiologically acceptable monomer, dimer, oligomer, or polymer is a glycosaminoglycan. In another embodiment, the phospholipid moiety is dipalmitoyl phosphatidylethanolamine and the physiologically acceptable monomer, dimer; oligomer, or polymer is heparin. In another embodiment, the phospholipid moiety is dipalmitoyl phosphatidylethanolamine and the physiologically acceptable monomer, dimer, oligomer, or polymer is chondroitin sulfate. In another embodiment, the phospholipid moiety is dipalmitoyl phosphatidylethanolamine and the physiologically acceptable monomer, dimer, oligomer, or polymer is hyaluronic acid. In another embodiment, the phospholipid moiety is dimyristoyl phosphatidylethanolamine and the physiologically acceptable monomer, dimer, oligomer, or polymer is hyaluronic acid.

In another embodiment, the invention provides a method of suppressing, inhibiting, preventing, or treating a vaccinia infection of a cell, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In another embodiment, the invention provides a method of suppressing, inhibiting, preventing, or treating a smallpox infection in a subject comprising the step of administering to said subject an effective amount of a lipid or phospholipid moiety bound to a physiologically acceptable monomer, dimer, oligomer, or polymer, and/or a pharmaceutically acceptable salt or a pharmaceutical product thereof. In one embodiment, the phospholipid moiety is phosphatidylethanolamine and the physiologically acceptable monomer, dimer, oligomer, or polymer is a glycosaminoglycan. In another embodiment, the phospholipid moiety is dipalmitoyl phosphatidylethanolamine and the physiologically acceptable monomer, dimer, oligomer, or polymer is heparin. In another embodiment, the phospholipid moiety is dipalmitoyl phosphatidylethanolamine and the physiologically acceptable monomer, dimer, oligomer, or polymer is chondroitin sulfate. In another embodiment, the phospholipid moiety is dipalmitoyl phosphatidylethanolamine and the physiologically acceptable monomer, dimer, oligomer, or polymer is hyaluronic acid. In another embodiment, the phospholipid moiety is dimyristoyl phosphatidylethanolamine and the physiologically acceptable monomer, dimer, oligomer, or polymer is hyaluronic acid.

In another embodiment, the invention provides a method of suppressing, inhibiting, preventing, or treating a smallpox infection of a cell, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In another embodiment, the invention provides a method of suppressing, inhibiting, preventing, or treating a poxvirus infection in a subject comprising the step of administering to said subject an effective amount of a lipid or phospholipid moiety bound to a physiologically acceptable monomer, dimer, oligomer, or polymer, and/or a pharmaceutically acceptable salt or a pharmaceutical product thereof. In one embodiment, the phospholipid moiety is phosphatidylethanolamine and the physiologically acceptable monomer, dimer, oligomer, or polymer is a glycosaminoglycan. In another embodiment, the phospholipid moiety is dipalmitoyl phosphatidylethanolamine and the physiologically acceptable monomer, dimer, oligomer, or polymer is heparin. In another embodiment, the phospholipid moiety is dipalmitoyl phosphatidylethanolamine and the physiologically acceptable monomer, dimer, oligomer, or polymer is chondroitin sulfate. In another embodiment, the phospholipid moiety is dipalmitoyl phosphatidylethanolamine and the physiologically acceptable monomer, dimer, oligomer, or polymer is hyaluronic acid. In another embodiment, the phospholipid moiety is dimyristoyl phosphatidylethanolamine and the physiologically acceptable monomer, dimer, oligomer, or polymer is hyaluronic acid.

In another embodiment, the invention provides a method of suppressing, inhibiting, preventing, or treating a poxvirus infection of a cell, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In another embodiment, the invention provides a method of suppressing, inhibiting, preventing, or treating a chordoppxvirinae infection in a subject comprising the step of administering to said subject an effective amount of a lipid or phospholipid moiety bound to a physiologically acceptable monomer, dimer, oligomer, or polymer, and/or a pharmaceutically acceptable salt or a pharmaceutical product thereof. In one embodiment, the phospholipid moiety is phosphatidylethanolamine and the physiologically acceptable monomer, dimer, oligomer, or polymer is a glycosaminoglycan. In another embodiment, the phospholipid moiety is dipalmitoyl phosphatidylethanolamine and the physiologically acceptable monomer, dimer, oligomer, or polymer is heparin. In another embodiment, the phospholipid moiety is dipalmitoyl phosphatidylethanolamine and the physiologically acceptable monomer, dimer, oligomer, or polymer is chondroitin sulfate. In another embodiment, the phospholipid moiety is dipalmitoyl phosphatidylethanolamine and the physiologically acceptable monomer, dimer, oligomer, or polymer is hyaluronic acid. In another embodiment, the phospholipid moiety is dimyristoyl phosphophatidylethanolamine and the physiologically acceptable monomer, dimer, oligomer, or polymer is hyaluronic acid.

In another embodiment, the invention provides a method of suppressing, inhibiting, preventing, of treating a chordopoxvirinae infection of a cell, comprising the step of contacting the cell with a compound comprising a lipid or phospholipid moiety bound to a physiologically acceptable monomer, dimer, oligomer, or polymer, and/or a pharmaceutically acceptable, salt or a pharmaceutical product thereof.

In one embodiment, the invention provides a method of treating a subject suffering from a vaccinia infection, including, inter alia, the step of administering to a subject an effective amount of a lipid or phospholipid moiety bonded to a physiologically acceptable monomer, dimer, oligomer, or polymer, thereby treating the subject suffering from a vaccinia infection.

In one embodiment, the invention provides a method of treating a subject suffering from a smallpox infection, including, inter alia, the step of administering to a subject an effective amount of a lipid or phospholipid moiety bonded to a physiologically acceptable monomer, dimer, oligomer, or polymer, thereby treating the subject suffering from a vaccinia infection.

In one embodiment, the invention provides a method of treating a subject suffering from a poxvirus infection, including, inter alia, the step of administering to a subject an effective amount of a lipid or phospholipid moiety bonded to a physiologically acceptable monomer, dimer, oligomer, or polymer, thereby treating the subject suffering from a poxvirus infection.

In one embodiment, the invention provides a method of treating a subject suffering from a chordopoxvirinae infection, including, inter alia, the step of administering to a subject an effective amount of a lipid or phospholipid moiety bonded to a physiologically acceptable monomer, dimer, oligomer, or polymer, thereby treating the subject suffering from a chordopoxvirinae infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a vaccinia infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a smallpox infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a poxvirus infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a chordopoxvirinae infection.

In one embodiment, Lipid-conjugates of the present invention suppress, inhibit, prevent, or treat vaccinia infection. In another embodiment, Lipid-conjugates decrease vaccinia virus titer. This is exemplified in Table 1.11 and represents an embodiment of this invention. In one embodiment, Compound XXII (see compound descriptions hereinbelow) is useful to treat vaccinia infection. This is exemplified in Table 1.11 and represents an embodiment of this invention. In another embodiment, Compound XXV (see compound descriptions hereinbelow) is useful to treat vaccinia infection. This is exemplified in Table 1.11 and represents an embodiment of this invention. In another embodiment, Compound XXIII (see compound descriptions hereinbelow) is useful to treat vaccinia infection. This is exemplified in Table 1.11 and represents an embodiment of this invention.

*Chlamydia*

In one embodiment, the bacterial pathogenic effect described hereinabove is mediated by *Chlamydia*. In another embodiment, the infection described hereinabove is mediated by *Chlamydia*.

In one embodiment, methods of the present invention treat sexually transmitted diseases (STDs), pneumonia, conjunctivitis, or a combination thereof due to *Chlamydia* infection.

In another embodiment, methods of the present invention treat chlamydia infection of genitals, cervix, urethra, rectum or throat. In one embodiment, the methods of the present invention may be used to treat *Chlamydia* infections infecting mucosal membranes, such as the cervix, rectum, urethra, throat, or conjunctiva. In another embodiment, methods of the present invention treat secondary complications of *Chlamydia* infection including inter alia, abnormal vaginal discharge, a burning sensation when urinating, lower abdominal pain, low back pain, nausea, fever, pain during intercourse, or bleeding between menstrual periods, penile discharge, or burning or itching around the opening of the penis. In another embodiment, methods of the present invention treat secondary complications of *Chlamydia* infection including pelvic inflammatory disease (PID). In another embodiment, methods of the present invention treat secondary complications of *Chlamydia* infection including chronic pelvic pain, infertility, or potentially fatal ectopic pregnancy in infected women. In another embodiment, methods of the present invention treat secondary complications of *Chlamydia* infection including pain, fever, or sterility in infected men.

In another embodiment, methods of the present invention treat arthritis that may be accompanied by skin lesions and inflammation of the eye and urethra (Reiter's syndrome). In one embodiment, methods of the present invention treat trachomoa or inclusion conjunctivitis resulting directly or indirectly from *Chlamydia* infection. In another embodiment, methods of the present invention treat pneumonia or bronchopulmonary infections resulting directly or indirectly from *Chlamydia* infection. In another embodiment, methods of the present invention treat *Lymphogranuloma venereum* due to *Chlamydia trachomatis* infection.

In one embodiment, the methods of the present invention may be used to treat *Chlamydia* infections that are acquired via zoonotic transmission, which may include inter alia, *Chlamydia psittaci* an avian form of *Chlamydia*. In one embodiment, *Chlamydia psittaci* is referred to as Psittacosis, Parrot Fever or chlamydiosis.

In one embodiment, the bacterial pathogenic effect, infection or combination thereof is mediated by *Chlamydia*. In one embodiment, the bacterial pathogenic effect, infection or combination thereof is mediated by *Chlamydia trachomatis*, in another embodiment by *Chlamydia muridarum* in another embodiment by *Chlamydophila caviae*, in another embodiment by *Chlamydia psittaci*, in another embodiment by *Chlamydia puerorum*, and in another embodiment by *Chlamydia pneumoniae*. In one embodiment, the bacterial pathogenic effect is mediated by any of *Chlamydia trachomatis* serovars (serologically variant strains). In one embodiment, it's mediated by Serovar A, in another embodiment by Serovar B, in another embodiment by Serovar Ba, in another embodiment by Serovar C, in another embodiment by Serovar D, in another embodiment by Serovar E, in another embodiment by Serovar F, in another embodiment by Serovar G, in another embodiment by Serovar H, in another embodiment by Serovar I, in another embodiment by Serovar J, in another embodiment by Serovar K, in another embodiment by Serovar L1, in another embodiment by Serovar L2, and in another embodiment by Serovar L3.

In another embodiment, the invention provides a method of suppressing, inhibiting, preventing, or treating a *Chlamydia* infection in a subject comprising the step of administering to said subject an effective amount of a lipid or phospholipid moiety bound to a physiologically acceptable monomer, dimer, oligomer; or polymer, and/or a pharmaceutically acceptable salt or a pharmaceutical product thereof. In one embodiment, the phospholipid moiety is phosphatidylethanolamine and the physiologically acceptable monomer, dimer, oligomer, or polymer is a glycosaminoglycan. In another embodiment, the phospholipid moiety is dipalmitoyl phosphatidylethanolamine and the physiologically acceptable monomer, dimer, oligomer, or polymer is heparin. In another embodiment, the phospholipid moiety is dipalmitoyl phosphatidylethanolamine and the physiologically acceptable monomer, dimer, oligomer, or polymer is chondroitin sulfate. In another embodiment, the phospholipid moiety is dipalmitoyl phosphatidylethanolamine and the physiologically acceptable monomer, dimer, oligomer, or polymer is hyaluronic acid. In another embodiment, the phospholipid is dimyristoyl phosphatidylethanolamine and the physiologically acceptable monomer, dimer, oligomer, or polymer is hyaluronic acid.

In another embodiment, the invention provides a method of suppressing, inhibiting, preventing, or treating a pathogenic effect on a cell due to *Chlamydia*, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof.

In one embodiment, the invention provides a method of treating a subject suffering from a *Chlamydia* infection, including, inter alia, the step of administering to a subject an effective amount of a lipid or phospholipid moiety bonded to a physiologically acceptable monomer, dimer, oligomer, or polymer, thereby treating the subject suffering from a *Chlamydia* infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a *Chlamydia* infection.

In one embodiment, Lipid-conjugates of the present invention suppress, inhibit, prevent, or treat *Chlamydia* infection. In another embodiment, Lipid-conjugates prevent infection by chlamydia virus. This is exemplified in FIG. 2.1 and represents an embodiment of this invention. In another embodiment, Lipid-conjugates prevent apoptosis induced by chlamydia virus. This is exemplified in FIG. 2.2 and represents an embodiment of this invention. In one embodiment, Compound XXII (see compound descriptions hereinbelow) is useful to treat chlamydia infection. This is exemplified in FIGS. 2.1-2.2 and represents an embodiment of this invention. In another embodiment, Compound XXIII (see compound descriptions hereinbelow) is useful to treat chlamydia infection. This is exemplified in FIGS. 2.1-2.2 and represents an embodiment of this invention. In another embodiment, Compound XXV (see compound descriptions hereinbelow) is useful to treat chlamydia infection. This is exemplified in FIGS. 2.1-2.3 and represents an embodiment of this invention. In another embodiment, Compound XXIV (see compound descriptions hereinbelow) is useful to treat chlamydia infection. This is exemplified in FIGS. 2.2-2.3 and represents an embodiment of this invention.

Other Pathogen-mediated Diseases and Conditions

Obstructive Respiratory Disease

In one embodiment, the methods of the present invention treat obstructive respiratory disease, which in one embodiment, can be caused or exacerbated by microbial infections. In one embodiment, obstructive respiratory disease is a disease of luminal passages in the lungs, which in one embodiment, is marked by dyspnea, tachypnea, or ausculatory or radiological signs of airway obstruction. In one embodiment, the methods of the present invention treat obstruction of air flow due to constriction of airway lumen smooth muscle, accumulation of infiltrates in and around the airway lumen, or a combination thereof.

In one embodiment, microbial-induced respiratory diseases may include influenza infection, which may, in one embodiment, exacerbate chronic asthma. In another embodiment, microbial-induced respiratory diseases may include *Chlamydia* infection, of which certain strains, in one embodiment target the respiratory tract. In one embodiment, microbial-induced respiratory diseases may include tuberculosis (TB), as is described hereinbelow.

In one embodiment, the invention provides a method of treating a subject suffering from obstructive respiratory disease, including, inter alia, the step of administering to a subject an effective amount of a lipid or phospholipid moiety bonded to a physiologically acceptable monomer, dimer, oligomer, or polymer, thereby treating the subject suffering from obstructive respiratory disease.

In one embodiment, the invention provides a use of a lipid or phospholipid moiety bonded to a physiologically acceptable monomer, dimer, oligomer, or polymer, in the, preparation of a pharmaceutical composition for treating a subject suffering from obstructive respiratory disease.

In one embodiment, obstructive respiratory disease is due to a pathogenic effect, while in another embodiment, it's due to a pathogenic infection. In another embodiment, it is due to a microbial infection, in another embodiment, it's due to a viral infection, while in another embodiment, it's due to a bacterial infection. In one embodiment, it's due to influenza, tuberculosis, schistosomiasis, chronic bronchitis, pneumonia, SARS, respiratory syncitial virus, Empyema Thoracis, whooping cough, or a combination thereof.

In one embodiment, the bacterial pathogenic effect described hereinabove is mediated by tuberculosis. In another embodiment, the infection described hereinabove is mediated by tuberculosis.

In one embodiment, the microbial-induced obstructive respiratory disease is tuberculosis (TB; *Mycobacterium tuberculosis*). In another embodiment, the methods of the present invention may be used to treat tuberculosis infections that are acquired via zoonotic transmission, which may include inter alia *Mycobacterium bovis*. In another embodiment, the invention provides a method of suppressing, inhibiting, preventing, or treating a pathogenic effect on a cell due to tuberculosis, comprising the step of contacting the cell with a compound comprising a lipid or phospholipid moiety bound to a physiologically acceptable monomer, dimer, oligomer, or polymer, and/or a pharmaceutically acceptable salt or a pharmaceutical product thereof. In another embodiment, the invention provides a method of suppressing, inhibiting, preventing, or treating a tuberculosis infection in a subject comprising the step of administering to said subject an effective amount of a lipid or phospholipid moiety bound to a physiologically acceptable monomer, dimer, oligomer, or polymer, and/or a pharmaceutically acceptable salt or a pharmaceutical product thereof.

In one embodiment, the invention provides a method of treating a subject suffering from a tuberculosis infection, including, inter alia, the step of administering to a subject an effective amount of a lipid or phospholipid moiety bonded to a physiologically acceptable monomer, dimer, oligomer, or polymer, thereby treating the subject suffering from a tuberculosis infection.

In one embodiment, the invention provides a use of a lipid or phospholipid moiety bonded to a physiologically acceptable monomer, dimer, oligomer, or polymer, in the preparation of a pharmaceutical composition for treating a subject afflicted with a tuberculosis infection.

Cytokine Overproduction

In one embodiment, the methods of the present invention treat cytokine overproduction, which in one embodiment, can be caused or exacerbated by microbial infections. In another embodiment, the methods of the present invention treat secondary complications including, inter alia, tissue damage. In one embodiment, cytokine overproduction is due to blood bourne bacteria (septicemia) or to the pulmonary condition known as acute (or adult) respiratory distress syndrome (ARDS). In one embodiment, the methods of the present invention prevent monocytic phagocytes and leukocytes from adhering to endothelial surfaces or undergoing a respiratory burst. In another embodiment, the methods prevent oxidant injury or release of chemokines such as Gro α, ENA-78, CX3X and MCP-1, leukotrienes, thromboxanes, prostaglandins, or a combination thereof. In another embodiment, the methods prevent the release of oxidants, mediators, or degradative enzymes, in another embodiment prevent endothelial cell damage or release of lysosomal enzymes by leukocytes. In one embodiment, the methods of the present invention treat vaginal bacterial infection in which cytokine overproduction plays a role.

In one embodiment, the invention provides a method for treating a subject with an infection marked by unchecked inflammation, inappropriate cytokine response, or a combination thereof, including inter alia, influenza, tuberculosis, schistosomiasis, chronic bronchitis, pneumonia, SARS, respiratory syncitial virus, Empyema Thoracis, whooping cough, etc.

In one embodiment, the invention provides a method for treating a subject requiring anti-TNF therapy, including, inter alia, the step of administering to a subject an effective amount of a lipid or phospholipid moiety bonded to a physiologically acceptable monomer, dimer, oligomer; or polymer, thereby treating the subject requiring an anti-TNF therapy. In one embodiment, the invention provides a use of a lipid or phospholipid moiety bonded to a physiologically acceptable monomer, dimer, oligomer, or polymer, in the preparation or a pharmaceutical composition for treating a subject requiring an anti-TNF therapy.

Sepsis

In one embodiment, the methods of the present invention treat sepsis, which in one embodiment, can be caused or exacerbated by microbial infections. In one embodiment, sepsis refers to sepsis, septicemia or septic shock. In one embodiment, sepsis syndrome and shock are triggered by the interactions of various microbial products in the blood, which in one embodiment are gram-negative endotoxins, with host mediator systems. In one embodiment, the methods of the present invention prevent activation of host mediators, including inter alia, cytokines, tumor necrosis factor-α (TNF), Gro α, ENA-78, CX3X and MCP-1, NFκβ transcription factor, lysosomal enzymes, oxidants from leukocytes, products of the metabolism of arachidonic acid, or a combination thereof.

In one embodiment, the invention provides a method of treating a subject suffering from sepsis, including, inter alia, the step of administering to a subject an effective amount of a lipid or phospholipid moiety bonded to a physiologically acceptable monomer, dimer, oligomer, or polymer, thereby treating the subject suffering from sepsis. In one embodiment, the invention provides a use of a lipid or phospholipid moiety bonded to a physiologically acceptable monomer, dimer, oligomer, or polymer, in the preparation of a pharmaceutical composition for treating a subject suffering from sepsis. In one embodiment, sepsis is due to a pathogenic effect. In another embodiment, it's due to a pathogenic infection, in another embodiment, a viral infection, in another embodiment, a bacterial infection. In one embodiment, the compounds for use in the present invention may protect against bacterial or viral induced septic shock.

Hemolysis

In one embodiment, the methods of the present invention treat hemolysis, which in one embodiment, can be caused or exacerbated by microbial infections. In one embodiment, hemolysis is red blood cell lysis, which in one embodiment may be an acquired disorder. In one embodiment, the methods of the present invention may be used to treat anemia, iron deficiency, or jaundice associated with hemolysis. In one embodiment, the methods of the present invention may be used to treat membrane anomalies, which in one embodiment, are due to infectious agents, including inter alia, viral, bacterial and parasitic etiologies. In one embodiment, the pathogen causing hemolysis is malaria, while in another embodiment, it's hemorrhagic fevers.

In one embodiment, the invention provides a method of treating a subject with hemolysis, including, inter alia, the step of administering to a subject an effective amount of a lipid or phospholipid moiety bonded to a physiologically acceptable monomer, dimer, oligomer, or polymer, thereby treating the subject with hemolysis. In one embodiment, the invention provides a use of a lipid or phospholipid moiety bonded to a physiologically acceptable monomer, dimer, oligomer, or polymer, in the preparation of a pharmaceutical composition for treating a subject with hemolysis. In one embodiment, hemolysis is due to a pathogenic effect. In another embodiment, it's due to a pathogenic infection, in another embodiment, a viral infection, in another embodiment, a bacterial infection. In one embodiment, the compounds for use in the present invention may protect against cytopathic effects due to infection or cell to cell spread.

Oxidative Injury

In one embodiment, the methods of the present invention treat oxidative injury, which in one embodiment, can be caused or exacerbated by microbial infections. In one embodiment, oxidative injury refers to the effect of peroxidation and free radical production on body tissues. In one embodiment, peroxide production is produced by the body in response to pathogenic infections, such as viral or bacterial infections. In one embodiment, free radicals are unpaired electrons that can damage cell proteins, DNA and lipids that may be formed as biological weapons against viruses, bacteria and cancer cells. In one embodiment, the methods of the present invention treat oxidative injury to membrane components or, in another embodiment, to blood proteins.

In one embodiment, the invention provides a method of treating a subject requiring anti-oxidant therapy, including, inter alia, the step of administering to a subject an effective amount of a lipid or phospholipid moiety bonded to a physiologically acceptable monomer, dimer, oligomer, or polymer, thereby treating the subject requiring an anti-oxidant therapy. In one embodiment, the invention provides a use of a lipid or phospholipid moiety bonded to a physiologically acceptable monomer, dimer, oligomer, or polymer, in the preparation of a pharmaceutical composition for treating a subject requiring an anti-oxidant therapy. In one embodiment, oxidative tissue damage is due to a pathogenic effect. In another embodiment, it's due to a pathogenic infection, in another embodiment, a viral infection, in another embodiment, a bacterial infection. In one embodiment, the compounds for use in the present invention may protect against tissue damage induced by viruses, bacteria or a combination thereof.

Central Nervous System Insult

In one embodiment, the methods of the present invention treat Central Nervous System Insult, which in one embodiment, can be caused or exacerbated by microbial infections. In one embodiment "Central Nervous System Insult" refers to neurological injury that may result from infection, ischemic stroke, trauma, cancer metastases, degenerative disease, or a combination thereof. In one embodiment, the methods of the present invention treat physiological responses to stress resulting from tissue injury. In one embodiment, the methods prevent the release of or treat the damage caused by chemical substances released by support tissue.

In one embodiment, central nervous system (CNS) tissue insult is due to a pathogenic effect. In another embodiment, it's due to a pathogenic infection, in another embodiment, a viral infection, in another embodiment, a bacterial infection. In one embodiment, CNS insult is due to viral meningitis, Encephalitis, Poliomyelitis, bacterial meningitis, subdural empyema, CNS helminthic infections or any combination thereof.

In one embodiment, the invention provides a method of treating a subject suffering from central nervous system tissue insult, including, inter alia, the step of administering to a subject an effective amount of a lipid or phospholipid moiety bonded to a physiologically acceptable monomer, dimer, oligomer, or polymer, thereby treating the subject suffering from a central nervous system insult. In one embodiment, the invention provides a use of a lipid or phospholipid moiety bonded to a physiologically acceptable monomer, dimer, oligomer, or polymer, in the preparation of a pharmaceutical composition for treating a subject suffering from central nervous system insult.

Conjunctivitis

In one embodiment, the methods of the present invention treat conjunctivitis, which in one embodiment, can be caused or exacerbated by microbial infections, which in one embodiment are viral and in another embodiment are bacterial. In one embodiment it is an infection of the conjunctiva (the outermost layer of the eye that covers the sclera).

In one embodiment, the methods of the present invention treat symptoms of viral conjunctivitis including inter alia conjunctival injection, tearing, serous discharge, edematous eyelids, pinpoint subconjunctival hemorrhages, pseudomembrane formation and palpable preauricular lymph nodes. In some embodiment, they treat conjunctival desiccation, which may cause scarring and symblepharon formation (adherence of the bulbar and palpebral conjunctivas), in one embodiment.

In one embodiment the methods of the present invention treat symptoms of conjunctivitis caused by epidemic keratoconjunctivitis (EKC) or pharyngoconjunctival fever (PCF). In one embodiment, symptoms of PCF comprise fever, sore throat and follicular conjunctivitis. In one embodiment, the pathogen causing PCF is adenovirus type 3, adenovirus type 4, or adenovirus type 7. In one embodiment, symptoms of EKC comprise bilateral, inferior, palpebral, follicular conjunctivitis, with epithelial and stromal keratitis or subepithelial corneal infiltrates. In one embodiment, the pathogen causing EKC is adenovirus type 8 or adenovirus type 19.

In one embodiment, the methods of the present invention treat symptoms of bacterial conjunctivitis, which, in one embodiment, is thick mucopurulent discharge, photophobia or discomfort. In one embodiment, the bacteria causing conjuctivitis, in one embodiment, is staphylococcus or streptococcus. In another embodiment, the pathogen is *Staphylococcus aureus, Haemophilus influenzae, Streptococcus pneumoniae, Pseudomonas aeruginosa, Neisseria gonorrhoeae* or *Corynebacterium diptheroides*. In one embodiment, the methods of the present invention treat penetration of an intact cornea.

In one embodiment, a subject is afflicted with conjunctivitis from a pathogenic source. In one embodiment, conjunctivitis is mediated by *Chlamydia trachomatis*, in another embodiment it's mediated by *Streptococcus pneumoniae*, in another embodiment it's mediated by *Haemophilus influenzae*, in another embodiment it's mediated by *Corynebacterium diptheroides*, in another embodiment it's mediated by *Pseudomonas aeruginosa*, while in another embodiment it's mediated by *Staphylococcus aureus*. In one embodiment, conjunctivitis is mediated by *Neisseria gonorrhoeae*, while in another embodiment, it's mediated by herpes simplex virus, while in another embodiment, while in another embodiment, it's mediated by an Adenovirus, while in another embodiment, it's mediated by an Enterovirus.

In one embodiment, the invention provides a method of treating a subject afflicted with conjunctivitis, including, inter alia, the step of administering to a subject an effective amount of a lipid or phospholipid moiety bonded to a physiologically acceptable monomer, dimer, oligomer, or polymer, thereby treating the subject afflicted with conjunctivitis. In one embodiment, the invention provides a use of a lipid or phospholipid moiety bonded to a physiologically acceptable monomer, dimer, oligomer, or polymer, in the preparation of a pharmaceutical composition for treating a subject afflicted with conjunctivitis.

Administration of the Lipid-conjugates in a diversity of animal and cell models of disease invoked remarkable, and unexpected, cytoprotective effects, which, as exemplified herein, are useful in the treatment of diseases related to pathogenic infection. Lipid-conjugates reduce HIV titre, inhibit p24 production, suppress cell fusion, block V3 antibody binding in a cell model of HIV infection; block cytopathic effects in a cell model of influenza infection; and prevent infection of cells by vaccinia virus (as exemplified in Example 1). Lipid-conjugates also reduced infection and apoptosis in a cell model of chlamydia infection (as exemplified in Example 2). The compounds for the use in the present invention also prevent smooth muscle airway constriction, reduce sPLA2 expression in rat lung, reduce cysteinyl leukotrienes, reduce NO production, prevent airway remodeling, and reduce tumor necrosis factor-α (TNF-α) in animal and cell models of obstructive-respiratory disease (as exemplified in Example-3). Lipid-conjugates also increased survival of septic rats, reduced TNF-α and IL-6 mRNA and protein levels, reduced sPLA2-IIA and iNOS mRNA, and reduced ICAM-1 protein in cell and animal models of sepsis (as exemplified in Example 4). Lipid-conjugates also stabilized red blood cell membranes in a cell model of hemolysis (as exemplified in Example 5). Lipid-conjugates are also effective in stabilizing biological membranes, preventing GAG degradation, and protecting against copper-induced oxidation in cell-models of oxidative injury (as exemplified in Example 6). Lipid-conjugates also inhibit NO production, PGE2, sPLA2, oleic acid, dopamine, and serotonin release from PC12 and glial cells in cell models of CNS injury (as exemplified in Example 7).

Thus, in one embodiment, the invention provides a treatment method that utilizes a lipid or phospholipid moiety bound to a physiologically acceptable monomer, dimer, oligomer, or polymer. These Lipid-conjugates display a wide-range combination of cytoprotective pharmacological activities. These compounds may in some embodiments, interfere with bacterial and viral spread and signs of infection, alleviate airway obstruction, attenuate oxidative damage to tissue proteins and cell membranes, reduce intracellular levels of chemokines and cytokines after exposure to bacterial endotoxins, and protect CNS cells by reducing release of neurotoxic agents.

In one embodiment of the present invention, the useful pharmacological properties of the Lipid-conjugates, some of which are described hereinabove, may be applied for clinical use, and disclosed herein as methods for the prevention or treatment of a disease. The biological basis of these methods may be readily demonstrated by standard cellular and animal models of disease, for example, as described in the Examples 1-7, hereinbelow.

In one embodiment, the pharmacological activities of Lipid-conjugates, including membrane stabilization, anti-inflammation, anti-oxidant action, and attenuation of chemokine levels, may contribute to a Lipid-conjugate-treated cell's resistance to pathogenic infection, such as HIV, influenza, vaccinia, smallpox, poxvirus, chordopoxvirinae, and *Chlamydia* infection. In one embodiment, cell membrane stabilization may ameliorate or prevent tissue injury arising in the course of a pathological disease state. In another embodiment, anti-oxidant action may limit oxidative damage to cell and blood components arising in tile course of a pathological disease state. In another embodiment, attenuation of chemokines levels may attenuate physiological reactions to stress that arise in the course of a pathological disease state.

In one embodiment, the present invention provides for use of a lipid moiety bonded to a physiologically acceptable monomer, dimer, oligomer, or polymer, in the preparation of a pharmaceutical composition for treating a subject afflicted with a pathogenic infection, which in one embodiment is a viral infection, and in another embodiment, a bacterial infection. In another embodiment, the use of the compounds is for treating symptoms or secondary complications related to the pathogenic infection.

In one embodiment, the methods of the present invention include a composition comprising the compounds as described and may be formulated for administration by topical, oral, nasal, aerosol, intravenous, intraocular, intra-arterial, subcutaneous, or suppository routes as will be described hereinbelow.

In one embodiment of the invention, the Lipid-conjugates described herein can be used to treat disease, through amelioration, or prevention, of tissue injury arising in the course of pathological disease states by stabilizing cell membranes; limiting oxidative damage to cell and blood components; or attenuating physiological reactions to stress, as expressed in elevated chemokine levels.

The medicinal properties of the compounds for use in the present invention are readily exemplified using animal models of particular diseases of interest. The patients to whom the lipid or phospholipid conjugates should be administered are those that are experiencing symptoms of disease or who are at risk of contracting the disease or experiencing a recurrent episode or exacerbation of the disease. Thus, the lipid or phospholipid conjugates of the present invention may be used to treat an individual with a disease or disorder or to prevent an individual from contracting a disease or developing a disorder.

The combination of lipids, such as, but not limited to phosphatidylethanolamine and phosphatidylserine with additional monomer or polymer moieties is thus a practical route to the production of new drugs for medical purposes, provided that the resultant chemical composition displays the desired range of pharmacological properties. In one embodiment, the Lipid-conjugates of this invention possess a combination of multiple and potent pharmacological effects in addition to the ability to inhibit the extracellular form of the enzyme phospholipase A2. While the pharmacological activity of the Lipid-conjugates described-herein may be due in part to the nature of the lipid moiety, the multiple and diverse combination of pharmacological properties observed for the Lipid-conjugates emerges from the ability of the compound structure to act essentially as several different drugs in one chemical entity.

In the cases described herein, the diversity of biological activities and the effectiveness in disease exhibited by the compounds for use in the present invention far exceed the properties anticipated by use of the starting materials themselves, when administered alone or in combination. However, the phospholipid conjugate compounds, alone or in combination, are valuable when used in the methods of treating diseases and conditions specifically described herein.

In one embodiment, methods of the present invention involve treating a subject by inter alia controlling the expression, production, and activity of phospholipases such as PLA2; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxidants, oxygen radicals and nitric oxide; protection of cells, tissues, and plasma lipoproteins from damaging agents, such as reactive oxygen species (ROS) and phospholipases; controlling the expression, production, and activity of cytokines, chemokines and interleukins; anti-oxidant therapy; anti-endotoxin therapy or any combination thereof.

In one embodiment of the invention, the term "controlling" refers to inhibiting the production and action of the above mentioned factors in order to maintain their activity at the normal basal level and suppress their activation in pathological conditions.

In one embodiment of the invention, invention is characterized by tie presence of damaging agents, which comprise, inter alia, phospholipases, reactive oxygen species (ROS), free radicals, lysophospholipids, fatty acids or derivatives thereof, hydrogen peroxides, phospholipids, oxidants, cationic proteins, streptolysins, proteases, hemolysins, or sialidases.

Dosages and Routes of Administration

As used herein, the term "pharmaceutically acceptable" refers to any formulation which is safe, and provides the appropriate delivery for the desired route of administration of an effective amount of at least one compound for use in the present invention. As such, all of the above-described formulations of the present invention are hereby referred to as "pharmaceutically acceptable." This term refers to the use of buffered formulations as well, wherein the pH is maintained at a particular desired value, ranging from pH 4.0 to pH 9.0, in accordance with the stability of the compounds and route of administration.

In one embodiment, a Lipid-conjugate used in the methods of this invention may be administered alone or within a composition comprising a Lipid-conjugate. In another embodiment, compositions comprising Lipid-conjugates in admixture with conventional excipients, i.e. pharmaceutically acceptable organic or inorganic carrier substances suitable for parenteral, enteral (e.g., oral) or topical application which do not deleteriously react with the active compounds may be used. Suitable pharmaceutically acceptable carriers include but are not limited to water; salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents e.g., vitamins.

In one embodiment, the therapeutic composition of the instant invention comprises a Lipid-conjugate and additional compounds effective in preventing or treating pathogenic infections. In one embodiment, the additional compounds comprise nucleotide analogs, interferons, or immunoglobulins. In another embodiment, the nucleotide analogs comprise acyclovir, ganciclovir, or ribavirin and interferons comprise alpha-, beta-, or gamma-interferons. In one embodiment, any one of the abovementioned additional compounds is administered with one or more Lipid-conjugates to treat a viral infection, which in one embodiment is influenza, in another embodiment, it's HIV, in another embodiment, it's poxvirus, in another embodiment, it's smallpox, while in another embodiment, it's vaccinia. In another embodiment, the additional compounds comprise nucleoside reverse transcriptase inhibitors, non-nucleoside reverse transcriptase inhibitors, protease inhibitors, or fusion and attachment inhibitors. In one embodiment, any one of the abovementioned additional compounds is administered with one or more Lipid-conjugates to treat a viral infection, which is in one embodiment HIV. In another embodiment, the additional compounds comprise Zidovudine, Didanosine, Zalcitabine, Stavudine, Lamivudine, Abacavir, Tenofovir, Nevirapine, Delavirdine, Efavirenz, Saquinavir, Ritonavir, Indinavir, Nelfinavir, Amprenavir, Lopinavir, Atazanavir, Fosamprenavir, or Enfuvirtide. In one embodiment, any one of the abovementioned additional compounds is administered with one or more of the Lipid-conjugates to treat a viral infection, which is in one embodiment HIV.

In another embodiment, the additional compounds comprise Lactam Antibiotics, Aminoglycosides, Macrolides, Lincomycin, Clindamycin, Tetracyclines, Quinolones, Polypeptides, Sulfonamides, Trimethoprim-Sulfamethoxazole, or antimicrobial Chemoprophylaxis. In another embodiment, the additional compound is Erythromycin. In one embodiment, any one of the abovementioned additional compounds is administered with one or more of the Lipid-conjugates to treat a bacterial infection, which is in one embodiment chlamydia. In another embodiment, the additional compounds comprise Rifampicin, Pyrazinamid, Isoniazid, or Ethambutol. In one embodiment, any one of the abovementioned additional compounds is administered with one or more of the Lipid-conjugates to treat a bacterial infection, which is in one embodiment tuberculosis.

In another embodiment, the additional compounds comprise albendazole, mebendazole, pyrantel pamoate, thiabendazole, chloroquine, mefloquine, quinine, atovaquone-proguanil, quinidine, pyrimethamine, doxycycline, or a combination thereof. In one embodiment, any one of the abovementioned additional compounds is administered with one or more of the Lipid-conjugates to treat a parasitic infection.

In another embodiment, the additional compounds comprise analgesics, cytokines, growth factors, or a combination thereof. Compositions of the present invention may comprise any one of the compounds listed hereinabove or any combination thereof for use in the methods of this invention.

While the examples provided herein describe use of the phospholipid conjugates in subcutaneous, intraperitoneal or topical administration, the success described affords good evidence to suppose that other routes of administration, or combinations with other pharmaceutical preparations, would be at least as successful. In one embodiment, the route of administration may be parenteral, enteral, or a combination thereof. In another embodiment, the route may be subcutaneous, intraperitoneal, intravenous, intra-arterial, topical, transdermal, intradermal, vaginal, rectal, intraocular, conjunctival, inhalation, nasal aspiration (spray), sublingual, oral, or a combination thereof. In one embodiment, the dosage regimen will be determined by skilled clinicians, based on factors such as exact nature of the condition being treated, the severity of the condition, the age and general physical condition of the patient, etc.

For parenteral application, particularly suitable are injectable, sterile solutions, preferably oily or aqueous solutions, as well as suspensions, emulsions, or implants, including suppositories and enemas Ampoules are convenient unit dosages. Such a suppository may comprise any agent described herein, and, in one embodiment, may be used to treat Chlamydia.

For application by inhalation, particularly for treatment of airway obstruction or congestion, solutions or suspensions of the compounds mixed and aerosolized or nebulized in the presence of the appropriate carrier suitable. Such an aerosol may comprise any agent described herein and, in one embodiment, may be used to treat diseases or conditions caused by airborne pathogens, which may be in one embodiment influenza or tuberculosis.

For topical application, particularly for the treatment of skin diseases such as contact dermatitis or psoriasis, admixture of the compounds with conventional creams, lotions, or delayed release patches is acceptable. Such a cream or lotion may comprise any agent described herein, and, in one embodiment, may be used to treat Chlamydia. In another embodiment, compounds for use in the present invention may be used to coat condoms, or any intravaginal or intraanal device. According to this embodiment, a compound of the invention may act as a lubricant, prevent infection by pathogens, such as HIV, or a combination thereof.

For enteral application, particularly suitable are tablets, dragees, liquids, drops, or capsules. A syrup, elixir, or the like can be used when a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, in one embodiment, the route of administration may be directed to an organ or system that is affected by the pathogenic infection. For example, compounds may be administered in aerosol form to treat infections by airborne pathogens. In another embodiment, the route of administration may be directed to a different organ or system than the one that is affected by the pathogenic infection. For example, compounds may be administered parenterally to treat infections by airborne pathogens.

Thus, the present invention provides for the use of Lipid-conjugates in various dosage forms suitable for administration using any of the routes listed hereinabove.

In general, the doses utilized for the above described purposes will vary, but will be in an effective amount to exert the desired anti-disease effect. As used herein, the term "pharmaceutically effective amount" refers to an amount of a compound of formulae A and I-XXI as described hereinbelow, which will produce the desired alleviation in symptoms or signs of disease in a patient. The doses utilized for any of the above-described purposes will generally be from 1 to about 1000 milligrams per kilogram of body weight (mg/kg), administered one to four times per day, or by continuous IV infusion. When the compositions are dosed topically, they will generally be in a concentration range of from 0.1 to about 10% w/v, administered 1-4 times per day.

In one embodiment of the invention, the concentrations of the compounds will depend on various factors, including the nature of the condition to be treated, the condition of the patient, the route of administration and the individual tolerability of the compositions.

It will be appreciated that the actual preferred amounts of active compound in a specific case will vary according to the specific compound being utilized, the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compounds of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may administered in a staggered fashion. In one embodiment, the staggered fashion may be dictated by the stage or phase of the disease.

In one embodiment, the present invention offers methods for the treatment of disease based upon administration of lipids covalently conjugated through their polar head group to a physiologically acceptable chemical moiety, which may be of high or low molecular weight.

The present invention has been illustrated in terms of the anti-disease activity of Lipid-conjugates and methods of their use as pharmaceutical compositions in the treatment of disease. The following sections present some examples of the therapeutic Lipid-conjugate compounds for use in the present invention and their chemical preparation.

Compounds

In one embodiment, the compounds for use in the present invention comprise a lipid or phospholipid moiety bound to a physiologically acceptable monomer, dimer, oligomer, or polymer. In one embodiment, the lipid compounds (Lipid-conjugates) for use in the present invention are described by the general formula:

[phosphatidylethanolamine-Y]n-X
[phosphatidylserine-Y]n-X
[phosphatidylcholine-Y]n-X
[phosphatidylinositol-Y]n-X
[phosphatidylglycerol-Y]n-X
[phosphatidic acid-Y]n-X
[lyso-phospholipid-Y]n-X
[diacyl-glycerol-Y]n-X
[monoacyl-glycerol-Y]n-X
[sphingomyelin-Y]n-X
[sphingosine-Y]n-X
[ceramide-Y]n-X wherein Y is either nothing or a spacer group ranging in length from 2 to 30 atoms; and X is a physiologically acceptable monomer, dimer, oligomer or polymer; and n is the number of lipid molecules bound to a molecule of X, wherein n is a number from 1 to 1000.

In one embodiment, the invention provides low-molecular weight Lipid-conjugates, previously undisclosed and unknown to possess pharmacological activity, of the general formula described hereinabove. In another embodiment, wherein the general formula described hereinabove describes low-molecular weight Lipid-conjugates, X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid.

In one embodiment of this invention, X is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment of this invention, n is a number from 1 to 1000. In another embodiment, n is a number from 1 to 500. In another embodiment, n is a number from 1 to 100. In another embodiment, n is a number from 2 to 100. In another embodiment, n is a number from 2 to 200. In another embodiment, n is a number from 3 to 300. In another embodiment, n is a number from 10 to 400. In another embodiment, n is a number from 50 to 500. In another embodiment, n is a number from 100 to 300. In another embodiment, n is a number from 300 to 500. In another embodiment, n is a number from 500 to 800. In another embodiment, n is a number from 500 to 1000.

In one embodiment, the set of compounds comprising phosphatidylethanolamine covalently bound to a physiologically acceptable monomer or polymer, is referred to herein as the PE-conjugates. In another embodiment, related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the Lipid-conjugates and the structural similarities shared by these compounds.

In another embodiment, the lipid or phospholipid moiety is phosphatidic acid, an acyl glycerol, monoacylglycerol, diacylglycerol, triacylglycerol, sphingosine, sphingomyelin, chondroitin-4-sulfate, chondroitin-6-sulfate, ceramide, phosphatidylethanolamine, phosphatidylserine, phosphatidylcholine, phosphatidylinositol, or phosphatidylglycerol, or an ether or alkyl phospholipid derivative thereof.

Other Lipid-conjugate derivatives relevant to this invention are Lipid-conjugates wherein at least one of the fatty acid groups of the lipid moieties at position C1 or C2 of the glycerol backbone are substituted by a long chain alkyl group attached by either is ether or alkyl bonds, rather than ester linkages.

As defined by the structural formulae provided herein for the Lipid-conjugates, these compounds may contain between one to one thousand lipid moieties bound to a single physiologically acceptable polymer molecule.

In the methods, according to embodiments of the invention, the Lipid-conjugates administered to the subject are comprised from at least one lipid moiety covalently bound through an atom of the polar head group to a monomeric or polymeric moiety (referred to herein as the conjugated moiety) of either low or high molecular weight. When desired, an optional bridging moiety can be used to link the Lipid-conjugates moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondroitin-sulfate, dermatan, keratan sulfate, or a higher molecular weight peptide or oligopeptide, a polysaccharide, polyglycan, protein, glycosaminoglycan, or a glycoprotein mixture. The composition of phospholipid-conjugates of high molecular weight, and associated analogues, are the subject of U.S. Pat. No. 5,064,817.

In one embodiment of the invention, when the conjugated carrier moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain Lipid-conjugate products with either high or low ratios of lipid residues per polymer, as desired.

In one embodiment, the term "moiety" means a chemical entity otherwise corresponding to a chemical compound, which has a valence satisfied by a covalent bond.

In one embodiment, examples of polymers which can be employed as the conjugated moiety for producing Lipid-conjugates for use in the methods of this invention may be physiologically acceptable polymers, including water-dispersible or -soluble polymers of various molecular weights and diverse chemical types, mainly natural and synthetic polymers, such as glycosaminoglycans, hyaluronic acids, heparin, heparin, sulfates, chondroitin sulfates, chondroitin-6-sulfates, chondroitin-4-sulfates, keratins, keratin sulfates, dermatins, dermatan sulfates, dextrans, plasma expanders, including polygeline ("Haemaccel", degraded gelatin polypeptide cross-linked via urea bridges, produced by "Behring"), "hydroxyethylstarch" (Hetastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g. polyethyleneglycols, polycarboxyethyleneglycols, polycarboxylated polyethyleneglycols), polyvinnylpyrrolidones, polysaccharides, alginates, assimilable gums (e.g., xanthan gum), peptides, injectable blood proteins (e.g., serum albumin), cyclodextrin, and derivatives thereof.

In one embodiment, examples of monomers, dimers, and oligomers which can be employed as the conjugated moiety for producing Lipid-conjugates for use in the methods of the invention may be mono- or disaccharides, trisaccharides, oligopeptides, carboxylic acids, dicarboxylic acids, fatty acids, dicarboxylic fatty acids, salicylates, slicyclic acids, acetyl salicylic acids, aspirins, lactobionic acids, maltoses, amino acids, glycines, glutaric acids, succinic acids, dodecanoic acids, didodecanoic acids, bile acids, cholic acids, cholesterylhemisuccinates, and di- and trisaccharide unit monomers of glycosaminoglycans including heparins, heparan sulfates, hyaluronic acids, chondroitins, chondroitin sulfates, chondroitin-6-sulfates, chondroitin-4-sulfates, dermatins, dermatan sulfates, keratins, keratan sulfates, or dextrans.

In some cases, according to embodiments of the invention, the monomer or polymer chosen for preparation of the Lipid-conjugate may in itself have select biological properties. For example, both heparin and hyaluronic acid are materials with known physiological functions. In the present invention, however, the Lipid-conjugates formed from these substances as starting materials display a new and wider set of pharmaceutical activities than would be predicted from administration of either heparin or hyaluronic acid which have not been bound by covalent linkage to a phospholipid. It can be shown, by standard comparative experiments as described below, that phosphatidylethanolamine (PE) linked to hyaluronic acid (Compound XXII), to heparin (Compound XXIV), to chondroitin sulfate A (Compound XXV), to carboxymethylcellulose (Compound XXVI), to Polygeline (haemaccel) (Compound XXVII), or to hydroxyethylstarch (Compound XXVIII), are far superior in terms of potency and range of useful pharmaceutical activity to the free conjugates (the polymers above and the like). In fact, these latter substances are, in general, not considered useful in methods for treatment of most of the diseases described herein, including the treatment of pathogenic infections. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone.

The biologically active Lipid-conjugates described herein can have a wide range of molecular weight, e.g., above 50,000 (up to a few hundred thousands) when it is desirable to retain the Lipid conjugate in the vascular system and below 50,000 when targeting to extravascular systems is desirable. The sole limitation on the molecular weight and the chemical structure of the conjugated moiety is that it does not result in a Lipid-conjugate devoid of the desired biological activity, or lead to chemical or physiological instability to the extent that the Lipid-conjugate is rendered useless as a drug in the method of use described herein.

In one embodiment, the compound according to the invention is represented by the structure of the general formula (A):

(A)

wherein
  L is a lipid or a phospholipid;
  Z is either nothing, ethanolamine, serine, inositol, choline, or glycerol;
  Y is either nothing or a spacer group ranging in length from 2 to 30 atoms;
  X is a physiologically acceptable monomer, dimer, oligomer, or polymer; and
  n is a number from 1 to 1000;
  wherein any bond between L, Z, Y and X is either an amide or an esteric bond.

In one embodiment, X is a glycosaminoglycan.

In one embodiment, L is phosphatidyl, Z is ethanolamine, wherein L and Z are chemically bonded resulting in phosphatidylethanolamine, Y is nothing, and X is hyaluronic acid, wherein any bond between the phosphatidylethanolamine and the hyaluronic acid is an amide bond. In one embodiment, the phosphatidylethanolamine moiety is dipalmitoyl phosphatidylethanolamine. In another embodiment, the phosphatidylethanolamine moiety is dimyristoyl phosphatidylethanolamine.

In another embodiment, L is phosphatidyl, Z is ethanolamine, wherein L and Z are chemically bonded resulting in phosphatidylethanolamine, Y is nothing, and X is chondroitin sulfate, wherein any bond between the phosphatidylethanolamine and the chondroitin sulfate is an amide bond. In one embodiments the phosphatidylethanolamine moiety is dipalmitoyl-phosphatidyl-ethanolamine. In another embodiment, the phosphatidylethanolamine moiety is dimyristoyl-phosphatidyl-ethanolamine.

In another embodiment, L is phosphatidyl, Z is ethanolamine, wherein L and Z are chemically bonded resulting in phosphatidylethanolamine, Y is nothing, and X is heparin, wherein any bond between the phosphatidylethanolamine and the heparin is an amide bond. In one embodiment, the phosphatidylethanolamine moiety is dipalmitoyl-phosphatidyl-ethanolamine. In another embodiment, the phosphatidylethanolamine moiety is dimyristoyl-phosphatidyl-ethanolamine.

In another embodiment, L is phosphatidyl, Z is ethanolamine, wherein L and Z are chemically bonded resulting in phosphatidylethanolamine, Y is nothing, and X is polygeline, wherein any bond between the phosphatidylethanolamine and the polygeline is an amide bond. In one embodiment, the phosphatidylethanolamine moiety is dipalmitoyl-phosphatidyl-ethanolamine. In another embodiment, the phosphatidylethanolamine moiety is dimyristoyl-phosphatidyl-ethanolamine.

In another embodiment, the compound according to the invention is represented by the structure of the general formula (I):

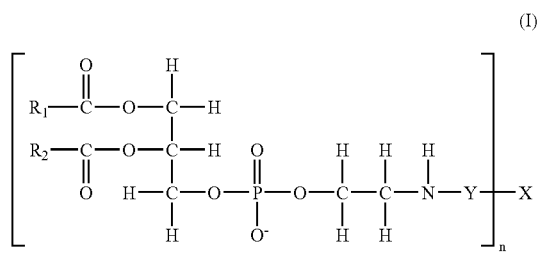

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is either a physiologically acceptable monomer, dimer, oligomer or a physiologically acceptable polymer; and
n is a number from 1 to 1,000;
wherein if Y is nothing the phosphatidylethanolamine is directly linked to X via an amide bond and if Y is a spacer, the spacer is directly linked to X via an amide or an esteric bond and to the phosphatidylethanolamine via an amide bond.

Preferred compounds for use in the methods of tie invention comprise one of the following as the conjugated moiety X acetate, butyrate, glutarate, succinate, dodecanoate, didodecanoate, maltose, lactobionic acid, dextran, alginate, aspirin, cholate, cholesterylhemisuccinate, carboxymethylcellulose, heparin, hyaluronic acid, polygeline (haemaccel), polyethyleneglycol, and polycarboxylated polyethylene glycol The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. According to the present invention, a most preferred PE moiety is dipalmitoyl-phosphatidyl-ethanolamine. In another preferred embodiment of the present invention, the PE moiety is dimyristoyl-phosphatidyl-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphatidylglycerol (PG), as well as derivatives thereof comprising either phospholipids, lysophospholipids, phosphatidyic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group; For PC, PI, and PG conjugates, the phospholipid is linked to-the conjugated monomer or polymer moiety through either the nitrogen or one of the oxygen atoms of the polar head group, either directly or via a spacer group.

In another embodiment, the compound according to the invention is represented by the structure of the general formula (II):

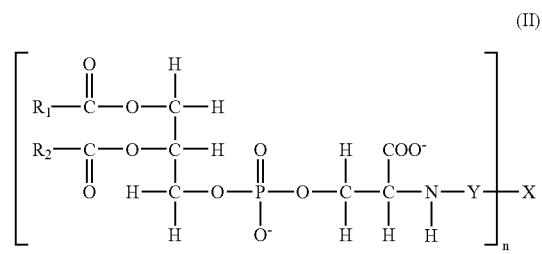

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a physiologically acceptable monomer, dimer, oligomer or polymer; and
n is a number from 1 to 1000;
wherein if Y is nothing, the phosphatidylserine is directly linked to X via an amide bond and if Y is a spacer, the spacer is directly linked to X via an amide or an esteric bond and to the phosphatidylserine via an amide bond.

In one embodiment, the phosphatidylserine may be bonded to Y, or to X if Y is nothing, via the COO⁻ moiety of the phosphatidylserine.

In another embodiment, the compound according to the invention is represented by the structure of the general formula (III):

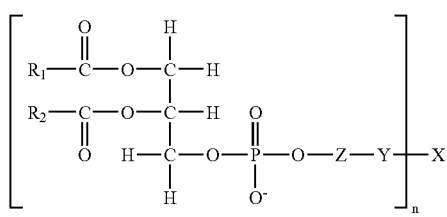

(III)

wherein
R$_1$ is a linear, saturated, mono-unsaturated, or poly-unsaturated, alkyl chain ranging in length from 2 to 30 carbon atoms;
R$_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between the phosphatidyl, Z, Y and X is either an amide or an esteric bond.

In another embodiment, the compound according to the invention is represented by the structure of the general formula (IV):

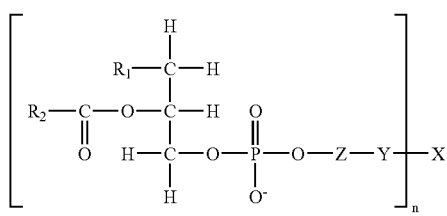

(IV)

wherein
R$_1$ is either hydrogen or a linear, saturated, mono-unsaturated, or poly-unsaturated, alkyl chain ranging in length from 2 to 30 carbon atoms;
R$_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between the phospholipid, Z, Y and X is either an amide or an esteric bond.

In another embodiment, the compound according to the invention is represented by the structure of the general formula (V):

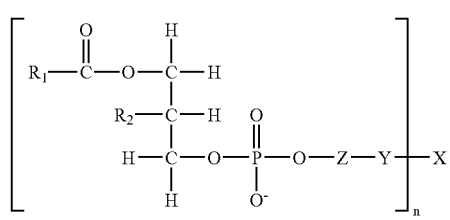

(V)

wherein
R$_1$ is a linear, saturated, mono-unsaturated, or poly-unsaturated, alkyl chain ranging in length from 2 to 30 carbon atoms;
R$_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between the phospholipid, Z, Y and X is either an amide or an esteric bond.

In another embodiment, the compound according to the invention is represented by the structure of the general formula (VI):

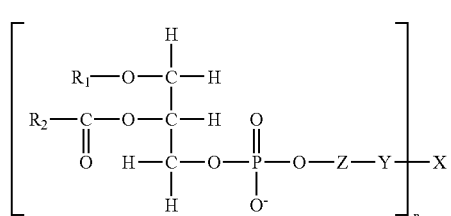

(VI)

wherein
R$_1$ is either hydrogen or a linear, saturated, mono-unsaturated, or poly-unsaturated, alkyl chain ranging in length from 2 to 30 carbon atoms;
R$_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between the phospholipid, Z, Y and X is either an amide or an esteric bond.

In another embodiment, the compound according to the invention is represented by the structure of the general formula (VII):

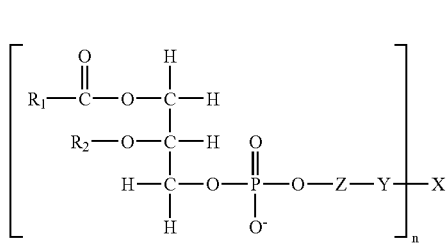

(VII)

wherein
- R₁ is a linear, saturated, mono-unsaturated, or poly-unsaturated, alkyl chain ranging in length from 2 to 30 carbon atoms;
- R₂ is either hydrogen or a linear, saturated, mono-unsaturated, or poly-unsaturated, alkyl chain ranging in length from 2 to 30 carbon atoms;
- Z is either nothing inositol, choline, or glycerol;
- Y is either nothing or a spacer group ranging in length from 2 to 30 atoms;
- X is a physiologically acceptable monomer, dimer, oligomer, or polymer; and
- n is a number from 1 to 1000;
- wherein any bond between the phospholipid, Z, Y and X is either an amide or an esteric bond.

In one embodiment of the invention, phosphatidylcholine (PC), phosphatidylinositol (PI), phosphatidic acid (PA), wherein Z is nothing, and phosphatidylglycerol (PG) conjugates are herein defined as compounds of the general formula (III).

In another embodiment, the compound according to the invention is represented by the structure of the general formula (VIII):

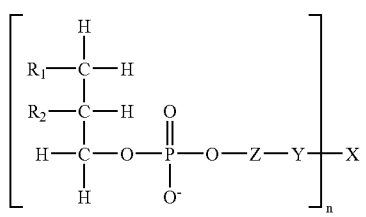

(VIII)

wherein
- R₁ is a linear, saturated, mono-unsaturated, or poly-unsaturated, alkyl chain ranging in length from 2 to 30 carbon atoms;
- R₂ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer; and
- n is a number from 1 to 1000;
- wherein any bond between the phospholipid, Z, Y and X is either an amide or an esteric bond.

In another embodiment, the compound according to the invention is represented by the structure of the general formula (IX):

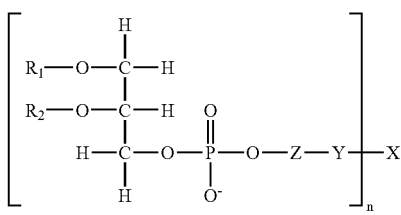

(IX)

wherein
- R₁ is either hydrogen or a linear, saturated, mono-unsaturated, or poly-unsaturated, alkyl chain ranging in length from 2 to 30 carbon atoms;
- R₂ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer; and
- n is a number from 1 to 1000;
- wherein any bond between the phospholipid, Z, Y and X is either an amide or an esteric bond.

In another embodiment, the compound according to the invention is represented by the structure of the general formula (IXa):

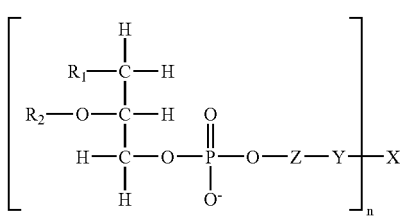

(IXa)

wherein
- R₁ is either hydrogen or a linear, saturated, mono-unsaturated, or poly-unsaturated, alkyl chain ranging in length from 2 to 30 carbon atoms;
- R₂ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer, and
- n is a number from 1 to 1000;
- wherein any bond between the phospholipid, Z, Y and X is either an amide or an esteric bond.

In another embodiment, the compound according to the invention is represented by the structure of the general formula (IXb):

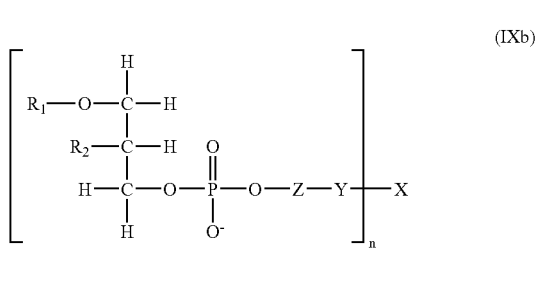

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer; and
- n is a number from 1 to 1000;
- wherein any bond between the phospholipid, Z, Y and X is either an amide or an esteric bond.

In another embodiment, the compound according to the invention is represented by the structure of the general formula (X):

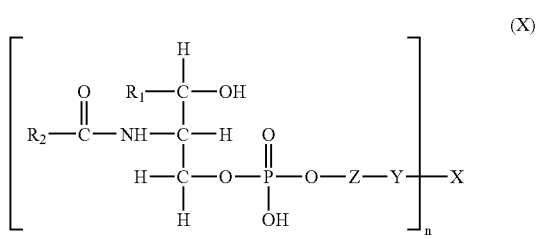

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer; and
- n is a number from 1 to 1000;
- wherein any bond between the ceramide phosphoryl, Z, Y and X is either an amide or an esteric bond.

In another embodiment, the compound according to the invention is represented by the structure of the general formula (XI):

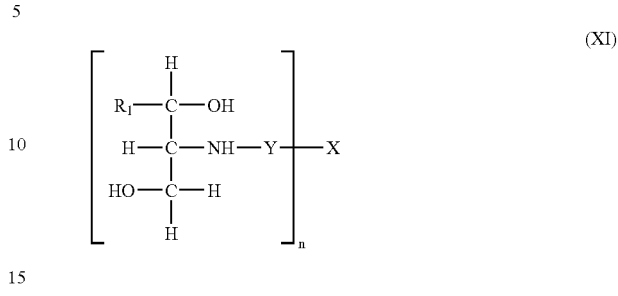

wherein
- $R_1$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer; and
- n is a number from 1 to 1000;
- wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound according to the invention is represented by the structure of the general formula (XII):

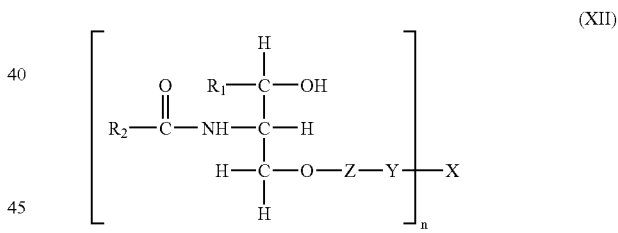

wherein
- $R_1$ is a linear, saturated, mono-unsaturated, or poly-unsaturated, alkyl chain ranging in length from 2 to 30 carbon atoms;
- $R_2$ is a lineal, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the ceramide, Z, Y and X is either an amide or an esteric bond.

In another embodiment, the compound according to the invention is represented by the structure of the general formula (XIII):

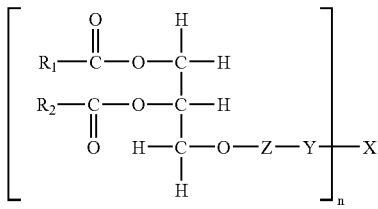

(XIII)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated; or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the diglyceryl, Z, Y and X is either an amide or an esteric bond.

In another embodiment, the compound according to the invention is represented by the structure of the general formula (XIV):

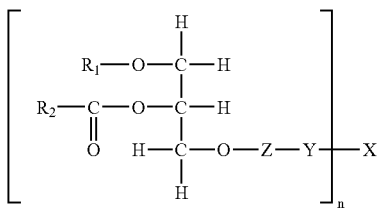

(XIV)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the glycerolipid, Z, Y and X is either an amide or an esteric bond.

In another embodiment, the compound according to the invention is represented by the structure of the general formula (XV):

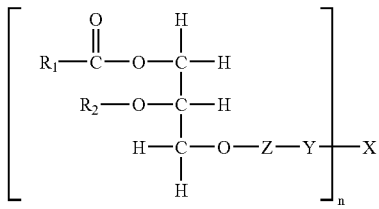

(XV)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the glycerolipid, Z, Y and X is either an amide or an esteric bond.

In another embodiment, the compound according to the invention is represented by the structure of the general formula (XVI):

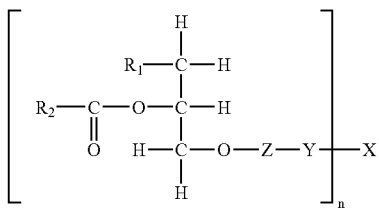

(XVI)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the lipid, Z, Y and X is either an amide or an esteric bond.

In another embodiment, the compound according to the invention is represented by the structure of the general formula (XVII):

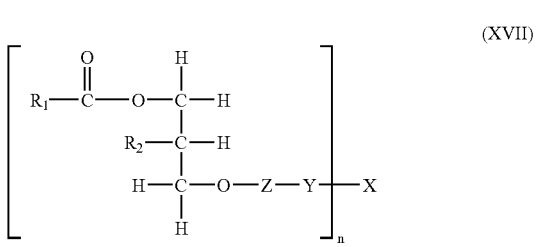

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the lipid, Z, Y and X is either an amide or an esteric bond.

In another embodiment, the compound according to the invention is represented by the structure of the general formula (XVIII):

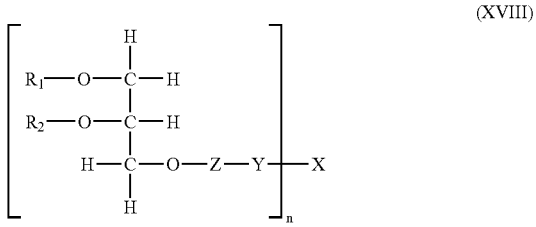

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the lipid, Z, Y and X is either an amide or an esteric bond.

In another embodiment, the compound according to the invention is represented by the structure of the general formula (XIX):

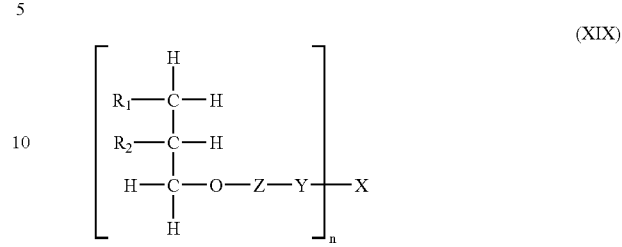

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the lipid, Z, Y and X is either an amide or an esteric bond.

In another embodiment, the compound according to the invention is represented by the structure of the general formula (XX):

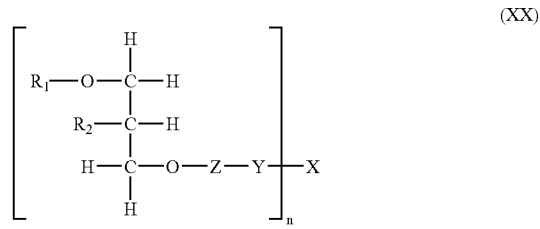

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the lipid, Z, Y and X is either an amide or an esteric bond.

In another embodiment, the compound according to the invention is represented by the structure of the general formula (XXI):

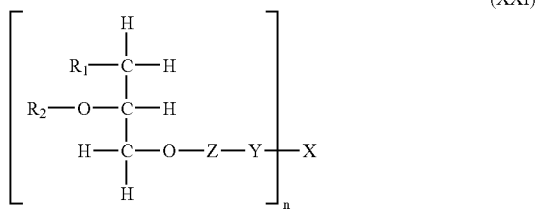

wherein
- R₁ is either hydrogen or a linear, saturated, mono-unsaturated, or poly-unsaturated, alkyl chain ranging in length from 2 to 30 carbon atoms;
- R₂ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer; and
- n is a number from 1 to 1000;
- wherein any bond between the lipid, Z, Y and X is either an amide or an esteric bond.

For any or all of the compounds represented by the structures of the general formulae: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), and (XXII) hereinabove: In one embodiment, X is a glycosaminoglycan.

In one embodiment of the invention, the glycosaminoglycan may be, inter alia, hyaluronic acid, heparin, heparan sulfate, chondroitin sulfate, keratin, keratan sulfate, dermatan sulfate or a derivative thereof.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, in is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In another embodiment, the chondroitin sulfate may be, inter alia, chondroitin-6-sulfate, chondroitin-4-sulfate or a derivative thereof.

In one embodiment of the invention Y is nothing. Non limiting examples of suitable divalent groups forming the optional bridging group (spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NHCO-alkylene-NH—, an amino acid, cycloalkylene, wherein alkylene in each instance, is straight or branched chain and contains 2 or more, preferably 2 to 30 atoms in the chain, —(—O—CH(CH₃)CH₂—)$_x$— wherein x is an integer of 1 or more.

According to embodiments of the invention, in addition to the traditional phospholipid structure, related derivatives for use in this invention are phospholipids modified at the C1 or C2 position to contain an ether or alkyl bond instead of an ester bond. In one embodiment of the invention, the alkyl phospholipid derivatives and ether phospholipid derivatives are exemplified herein.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, tile structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In one embodiment, the compound according to the invention is phosphatidylethanolamine bound to aspirin. In one embodiment, the compound according to the invention is phosphatidylethanolamine bound to glutarate.

In some embodiments, the compounds for use are as listed in Table 1 below.

TABLE 1

| Phospholipid | Spacer | Polymer (m.w.) | Compound |
|---|---|---|---|
| PE | None | Hyaluronic acid (2-2000 kDa) | XXII |
| Dimyristoyl-PE | None | Hyaluronic acid | XXIII |
| PE | None | Heparin (0.5-110 kDa) | XXIV |
| PE | None | Chondroitin sulfate A | XXV |
| PE | None | Carboxymethylcellulose (20-500 kDa) | XXVI |
| PE | Dicarboxylic acid + Diamine | Polygeline (haemaccel) (4-40 kDa) | XXVII |
| PE | None | Hydroxyethylstarch | XXVIII |
| PE | Dicarboxylic acid + Diamine | Dextran (1-2,000 kDa) | XXIX |
| PE | None | Aspirin | XXX |
| PE | Carboxyl amino group | Hyaluronic acid (2-2000 kDa) | XXXI |
| PE | Dicarboxyl group | Hyaluronic acid (2-2000 kDa) | XXXII |
| PE | Dipalmitoic acid | Hyaluronic acid (2-2000 kDa) | XXXIII |
| PE | Carboxyl amino group | Heparin (0.5-110 kDa) | XXXIV |
| PE | Dicarboxyl group | Heparin (0.5-110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20-500 kDa) | XXXVIII |
| PE | Dicarboxyl group | Carboxymethylcellulose (20-500 kDa) | XXXIX |

TABLE 1-continued

| Phospholipid | Spacer | Polymer (m.w.) | Compound |
|---|---|---|---|
| PE | None | Polygeline (haemaccel) (4-40 kDa) | XL |
| PE | Carboxyl amino group | Polygeline (haemaccel) (4-40 kDa) | XLI |
| PE | Dicarboxyl group | Polygeline (haemaccel) (4-40 kDa) | XLII |
| PE | Carboxyl amino group | Hydroxyethylstarch | XLIII |
| PE | Dicarboxyl group | Hydroxyethylstarch | XLIV |
| PE | None | Dextran (1-2,000 kDa) | XLV |
| PE | Carboxyl amino group | Dextran (1-2,000 kDa) | XLVI |
| PE | Dicarboxyl group | Dextran (1-2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2-2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl-hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |

In one embodiment of the invention, the compounds administered are Compound XXII, Compound XXIII, Compound XXIV, Compound XXV, Compound XXVI, Compound XXVII, Compound XXVIII, Compound XXIX and Compound XXX, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of tile polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy, as shown in the section below.

In one embodiment of this invention, low molecular weight phosphatidylethanolamine (PE)-conjugates are defined hereinabove as the compounds of formula (I) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In one embodiment of this invention, low molecular weight phosphatidylserine (PS)-conjugates are defined hereinabove as the compounds of formula (II) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In one embodiment of this invention, Phosphatidylcholine (PC), Phosphatidylinositol (PI), and Phosphatidylglycerol (PG) conjugates are hereinabove defined as the compounds of formula (III) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

Examples of suitable divalent groups forming the optional bridging group Y are straight- or branched-chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In another embodiment, related low molecular weight derivatives for use in this invention are exemplified hereinabove by the general formulae (X), (XI) and (XII) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In another embodiment, related low molecular weight-derivatives for use in this invention are exemplified hereinabove by the general formulae (XIII) wherein:

$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid; and n is the number of lipid moiety molecules bound to a molecule of X wherein n is a number from 1 to 1000.

In one embodiment of the invention, x is covalently conjugated to a lipid. In another embodiment, x is covalently conjugated to a lipid via an amide bond. In another embodiment, x is covalently conjugated to a lipid via an esteric bond. In another embodiment, the lipid is phosphatidylethanolamine. In another embodiment, the GAG may be, inter alia, chondroitin sulfate. In another embodiment, the GAG may be, inter alia, heparin. In another embodiment, the GAG may be, inter alia, hyaluronic acid. In another embodiment, the conjugate is biodegradable.

In one embodiment, the invention provides glycosaminoglycan (GAG) compounds covalently conjugated to a lipid to obtain a compound having preferred therapeutic properties. In another embodiment, the GAG compound is covalently conjugated to a lipid via an amide bond. In another embodiment, the GAG compound is covalently conjugated to a lipid via an esteric bond. In another embodiment, the lipid may be, inter alia, phosphatidylethanolamine. In another embodiment, the GAG may be, inter alia, chondroitin sulfate. In another embodiment, the GAG may be, inter alia, heparin. In another embodiment, the GAG may be, inter alia, hyaluronic acid. In another embodiment, the conjugate is biodegradable.

Cell surface GAGs play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAGs protect cells from bacterial, viral and parasitic infection, and their stripping exposes the cell to interaction and subsequent internalization of the microorganism. Enrichment of cell surface GAGs would thus assist in protection of the cell from injurious processes. Thus, in one embodiment of the invention, PLA2 inhibitors are conjugated to GAGs or GAG-mimicking molecules. In another embodiment, these Lipid-conjugates provide wide-range protection from diverse injurious processes, and are effective in amelioration of diseases that requires cell protection from injurious biochemical mediators.

In another embodiment, a GAG-mimicking molecule may be, inter alia, a negatively charged molecule. In another embodiment, a GAG-mimicking molecule may be, inter alia, a salicylate derivative. In another embodiment, a GAG-mimicking molecule may be, in inter alia, a dicarboxylic acid.

In another embodiment, the invention provides a pharmaceutical composition for treating a subject suffering from a pathogenic effect, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a viral infection, including a lipid or phospholipid moiety bonded to a physiologically acceptable monomer, dimer; oligomer, or polymer; and a pharmaceutically acceptable carrier or excipient.

In another embodiment, the invention provides a pharmaceutical composition for treating a subject suffering from an HIV infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from an influenza infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a poxvirus infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a chordopoxvirinae infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a vaccinia infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a smallpox infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a bacterial infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a *Chlamydia* infection, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a pathogenic effect, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof.

In another embodiment, the invention provides a pharmaceutical composition for treating a subject suffering from a viral infection, including any one of the compounds for use in the present invention or any combination thereof, and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from an HIV infection, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from an influenza infection, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from a poxvirus infection, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from a chordopoxvirinae infection, including any one of the compounds for use in the present invention or any combination thereof; and a pharmaceutically acceptable carrier or excipient. In another embodiment, the compounds for use in the present invention include, inter alia, the compounds represented by the structures of the general formulae: as described hereinbelow (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from a vaccinia infection, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from a smallpox infection, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from a bacterial infection, including any one of tile compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

In another embodiment, the invention provides a pharmaceutical composition for treating a subject suffering from a *Chlamydia* infection, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or any combination thereof.

Preparation of Compounds for Use in the Present Invention

The preparation of some high molecular weight Lipid-conjugates is the subject of U.S. Pat. No. 5,064,817, which is incorporated herein by reference. These synthetic methods are considered to be applicable as well to the preparation of low molecular weight Lipid-conjugates, i.e. Lipid-conjugates comprising monomers and dimers as the conjugated moiety, with appropriate modifications in the procedure as would be readily evident to one skilled in the art. The preparation of some low molecular weight Lipid-conjugates may be conducted using methods well known in the art or as described in U.S. patent application Ser. No. 10/952,496, which is incorporated herein by reference.

Without further elaboration, it is believed that one skilled in the art can, using the preceding description, utilize the present invention to its fullest extent. The following preferred specific embodiments are, therefore, to be construed as merely illustrative, and not limiting the remainder of the disclosure in any way whatsoever.

EXAMPLES

The abbreviations used in the examples below are:
PE=phosphatidyl-ethanolamine
HA=hyaluronic acid
Cpd=Compound
Compound XXII=dipalmitoyl-PE conjugated to HA
Compound XXIII=dimyristoyl-phosphatidyl-ethanolamine linked to HA
Compound XXIV=PE conjugated to heparin
CSA=chondroitin sulfate A
Compound XXV=PE conjugated to CSA
CMC=carboxymethyl cellulose
Compound XXVI=PE conjugated to CMC
Compound XXVII=PE conjugated to Polygeline (haemaccel)

The compounds used in the examples below were prepared as described in U.S. patent application Ser. No. 10/952,496, which is incorporated herein by reference.

Example 1

Viral Infection

The Lipid-conjugates are effective in the prophylaxis and treatment of viral infection, particularly infections due to the human immunodeficiency virus (HIV), human influenza virus and vaccinia virus. This is demonstrated for HIV in Experiments 1.1-1.3 below, for human influenza virus in Experiment 1.4-1.5, and for vaccinia in Experiment 1.6 below Viral infection is the cause of a number of human and animal diseases throughout the world. The process of viral infection comprises several stages, including attachment, penetration, uncoating, replication, maturation, release and reinfection. In order to assess the ability of Lipid-conjugates to prevent viral infection, human cell lines were incubated with a preparation of a viral agent, and the ability of the virus to infect cells is compared in the presence and absence of Lipid-conjugate.

Experiment 1.1: To demonstrate that the Lipid-conjugates are capable of preventing HIV infection of target cells, whole blood units were mixed with HIV and a Lipid-conjugate (50 µM Compound XXIV, 30 µM Compound XXII) for 30 min. The cells were then spun and the supernatant was examined for HIV infectivity on HT4-1022 cells as described by Margolis-Nunno et al. (Transfusion, 36, 743-750, 1996). FIG. 1.1 demonstrates the ability of Lipid-conjugates to prevent HIV infection of cells.

Experiment 1.2: Inhibition of HIV-1$_{IIIB}$ Infection

Tables 1.1-1.2 demonstrate the capacity of the Lipid-conjugates to inhibit HIV replication, as expressed by the production of the nucleocapsid p24 antigen, which is produced in the host cell upon its infection by HIV virus. $^{31}$MT-2 cells ($10^4$) in 96-well plates were infected with a dose of HIV-1 sufficient to accomplish a multiplicity of infection of 0.0045 in 200 µl of RPMI 1640 medium supplemented with 10% (v/v) fetal bovine serum (FBS), in the absence (control) and presence of the indicated Lipid-conjugate. After 1 h, half of the culture medium was changed and replaced by fresh medium (with/without Lipid-conjugate) and after 24 h, the second half of the culture medium was changed and replaced by fresh medium (with/without Lipid-conjugate). On the fourth day after incubation at 37° C., 100 µl of culture supernatants were collected from each well and an equal volume of fresh medium was added to the wells. The collected supernatants were mixed with an equal volume of 5% (v/v) Triton X-100 and assayed for p24 antigen using an ELISA kit from Coulter Immunology (Hialeah, Fla.).

TABLE 1.1

Inhibition of p24 production

| Compound | IC$_{50}$ (mean ± SD) µg/ml | IC$_{90}$ (mean ± SD) µg/ml |
| --- | --- | --- |
| Compound XXII | 207.0 ± 18.0 | 384.3 ± 79.3 |
| Compound XXIII | 118.0 ± 16.8 | 296.3 ± 104.0 |
| Compound XXIV | 10.0 ± 2.3 | 19.3 ± 4.5 |
| Compound XXV | 72.5 ± 8.0 | 106.0 ± 10.3 |
| Compound XXVII | 375.8 ± 119.5 | >500 |

TABLE 1.2

Inhibition of p24 production

| Compound | IC$_{50}$ (µM) | IC$_{90}$ (µM) |
| --- | --- | --- |
| Compound XXIII | 1.77 | 4.44 |
| Compound XXII | 3.11 | 5.76 |
| Compound XXIV | 0.70 | 1.35 |
| Compound XXV | 1.45 | 2.12 |

Experiment 1.3 demonstrates the ability of Lipid-conjugates to inhibit fusion between HIV-1-infected and HIV-uninfected cells. In this assay, HIV-1$_{IIIB}$-infected H9 cells were labeled with BCECF (2',7'-bis(2-carboxyethyl)-5-6-carboxy-fluorescein-acetoxymethyl-ester, Molecular Probes, Eugene, Oreg.) according to the manufacturer's instructions. BCECF-labeled H9/HIV-1 IIIB cells ($10^4$) were mixed with $1\times10^5$ uninfected MT-2 cells. After incubation in a 96-well plate at 37° C. for 2 h, the fused and unfused labeled cells were counted under an inverted fluorescence microscope at ×160 magnification. At least 200 BCECF-labeled cells were counted and the proportion of fused cells was determined Fusion tests were carried out in the presence and absence of graded quantities of the tested Lipid-conjugates. Data are presented as the IC$_{50}$ and IC$_{90}$ of the lipid conjugates tested (Table 1.3). The IC$_{50}$ represents the concentration of a drug that is required to achieve 50% inhibition. Similarly, the IC$_{90}$ represents the concentration of a drug that is required to achieve 90% inhibition.

TABLE 1.3

Inhibition of fusion between HIV-infected and uninfected cells.

| Compound | IC$_{50}$ (mean ± SD) µg/ml | IC$_{90}$ (mean ± SD) µg/ml |
| --- | --- | --- |
| Compound XXII | >500 | >500 |
| Compound XXIII | 122.8 ± 14.8 | 219.8 ± 10.6 |
| Compound XXIV | 7.9 ± 1.3 | 15.3 ± 3.9 |
| Compound XXV | >500 | >500 |
| Compound XXVII | >500 | >500 |

In another experiment, whole blood units were mixed with HIV and Lipid-conjugates (between 30 µM and 50 µM) for 30 min. Cells were spun, and supernatant was examined for HIV infectivity on HT4-1022 cells (Table 1.4).

TABLE 1.4

Inhibition of fusion between HIV-infected and uninfected cells.

| Compound | IC$_{50}$ (µM) | IC$_{90}$ (µM) |
| --- | --- | --- |
| Compound XXII | >7.5 | >7.5 |
| Compound XXIII | 1.83 | 3.30 |
| Compound XXIV | 0.55 | 1.07 |
| Compound XXV | >10 | >10 |

Table 1.5 further demonstrates the ability of Lipid-conjugates to inhibit HIV infection. V3 antibody binding is an assay that uses an antibody that binds to the V3 (third variable) domain of the human immunodeficiency virus type 1 (HIV-1) envelope glycoprotein gp120. Anti-V3 domain antibodies may provide an indicator of the presence and amount of HIV. V3 antibody binding was determined by standard ELISA.

TABLE 1.5

Effect of Lipid-conjugates on V3 antibody binding

| Compound | IC$_{50}$ (µM) |
| --- | --- |
| Compound XXII | 45 |
| Compound XXIII | 3 |
| Compound XXIV | 140 |
| Compound XXV | 0.2 |

These experiments demonstrate that administration of Lipid-conjugates is an effective therapy in the treatment HIV, including prevention of infection, replication and fusion.

Experiment 1.4: The effect of Lipid-conjugate treatment on human influenza virus infection in vitro.

Virus and cell lines. Each virus was obtained from the source described in Table 1.6. Kidney cell lines were obtained from American Type Culture Collection (ATCC). The cells were grown in minimal essential medium (Gibco-BRL, Gaithersburg, Md.) supplemented with 0.1% NaHCO$_3$ and 5 to 9% fetal bovine serum (HyClone Laboratories, Logan, Utah). When performing antiviral assays, serum was reduced to 2% and 50 µg gentamicin (Sigma Chemical Company, St. Louis, Mo.) per ml was added to the medium

TABLE 1.6

Description of viruses used in a screen of some Lipid-conjugates

| Virus | Strain | Source | Cell line |
|---|---|---|---|
| Influenza type A | A/New Caledonia/ 20/99 (H1N1) | Center for Disease Control and Prevention [CDC] | Madin Darby canine kidney (MDCK) cells |
|  | A/Panama/ 2007/99 (H3N2) | CDC | Madin Darby canine kidney (MDCK) cells |
| Influenza type B | B/Hong Kong/330/02 | CDC | Madin Darby canine kidney (MDCK) cells |
| Pichinde virus | An 4763 | Dr. J. D. Gangemi, Univ. of South Carolina School of Medicine, Columbia, SC | African green monkey kidney (BS-C-1) cells |
| Punta Toro virus | Adames | U.S. Army Medical Research Institute for Infectious Diseases, Fort Detrick, Frederick, MD | Rhesus monkey kidney (LLC-MK2) cells |
| Respiratory syncytial virus | A2 | ATCC | African green monkey kidney (MA-104) cells |

1. Inhibition of Viral Cytopathic Effect (CPE)

A. Visual Observation

A viral CPE assay was performed as described (Barnard DL et al. Antivir Chem Chemother. 2001 July; 12(4):241-250).

Compounds were evaluated using four log10 dilutions of each test compound (e.g., 1000, 100, 10, 1 µg/ml) (Tables 1.7 and 1.8) with an additional concentration of 2000 µg/ml for some experiments (Tables 1.9 and 1.10). Viruses (Influenza type A Strain H1N1, Influenza type A Strain H3N2, Influenza type B, Pichinde virus, Punta Toro virus, and Respiratory syncytial virus) were used at a multiplicity of infection (MOI) of 0.001 to 0.010. The MOIs used were virus dependent and chosen for each strain such that 100% of the cells in the virus controls showed cytopathic effects (CPE) within 5 to 7 days. Cell were grown to an 18 h monolayer (80-100% confluent) in 96-well tissue culture plates and were incubated with various concentrations of each compound as described above. Within 5 minutes of compound incubation, a volume of virus equal to that of the compound was added to the cells. The plates were then sealed and incubated at 37° C. for approximately 72 to 120 hr until the cells in the virus control wells showed complete viral CPE as observed by light microscopy.

Each concentration of drug was assayed for virus inhibition in triplicate. Three wells were set aside as uninfected, untreated cell controls per test and three wells per test compound receive untreated, virus-infected cells and represented positive controls for virus replication. Ribavirin, used as a positive control drug, was evaluated in parallel with compounds for each virus.

The 50% effective concentrations ($EC_{50}$) were calculated by regression analysis of the means of the CPE ratings as compared to untreated, uninfected controls for each concentration. Cells were rated based on changes in enlargement, granularity, ragged edges, filmy appearance, rounding, detachment from the surface of the well, and other changes. Morphological changes results from cytotoxicity of a compound were graded on a scale of 0-5; 0=no toxicity, 1=partial toxicity-slight, 2=partial toxicity, 3=partial toxicity-heavy, 4=partial toxicity-very heavy, and 5=complete cytotoxicity, based on the degree of cytotoxicity observed. The CPE results were then quantified spectrophotometrically by neutral red (NR) uptake assay (see below).

B. Increase in Neutral Red (NR) Dye Uptake

A Neutral Red Dye Uptake assay was performed as described previously (McManus, N H, Appl. Environment. Microbiol. 31:35-38, 1976) to verify the inhibitory activity and cytotoxicity that was observed in the CPE inhibition assay. Briefly, medium was removed from each well of a plate scored for CPE from a CPE inhibition assay, 0.034% NR in Sörenson's citrate buffer (pH 4.0) was added to each well of the plate and the plate incubated for 2 h at 37° C. in the dark. The NR solution was removed from the wells. After rinsing and aspirating to dryness, the remaining dye was extracted for 30 min, at room temperature in the dark, from the cells using absolute ethanol buffered with Sörenson's citrate buffer. The percentage of NR uptake, indicating viable cells, was read on a microplate autoreader (Bio-Tek EL 1309; Bio-Tek Instruments, Wilnooski, Vt., USA) at dual wavelengths of 405 and 540 nm. The difference between the two readings were calculated to eliminate background. Absorbance values were expressed as percentages of untreated controls, and EC50 values were calculated as described above.

2. Cytotoxicity Assay

A. Visual Observation

Uninfected cells were treated with each concentration of test compound in duplicate and run in parallel with the infected, treated wells in the CPE inhibition tests described above. The toxicity control cells (uninfected and treated) were examined under a light microscope for changes in cell appearance compared to control cells (uninfected, untreated) on the same plate as described above. The 50% cell inhibitory (cytotoxic) concentrations ($IC_{50}$) were calculated by regression analysis.

B. Neutral Red Uptake

The toxicity control cells (uninfected and treated) described in the previous section were further examined for neutral red dye uptake compared to control cells (uninfected, untreated) on the same plate. Neutral red was added to the toxicity control wells and the degree of color intensity was determined spectrophotometrically as described above. A neutral red IC50 (NR IC50) was subsequently determined. Absorbance values were expressed as percentages of uninfected, untreated controls, and $IC_{50}$ values were calculated as described above.

3. Data Analysis

Each test compound's antiviral activity was expressed as a selectivity index (SI), which is the $IC_{50}$ divided by the $EC_{50}$. Generally, an SI of 10 or greater is indicative of positive antiviral activity, although other factors, such as a low SI for the positive control, are also taken into consideration.

Tables 1.7 and 1.8 demonstrate the capacity of the Lipid-conjugates evaluated at low concentration to prevent infection of target cells by influenza virus.

Nine compounds were evaluated for in vitro antiviral testing against influenza A (H1N1 strain) virus, influenza A (H3N2 strain) virus, influenza B virus, respiratory syncitial virus (RSV), Punta Toro virus, and Pichinde virus using various kidney cell lines described in Table 1.6. Two series of Lipid-conjugate dosages were used as described in the methods hereinabove.

Using a lower range of doses, Compound XXIV had significant anti-viral activity against influenza A (H1N1 strain) virus (Table 1.7). The EC50 vs this virus was 5 µg/ml by visual assay and 2.5 µg/ml by neutral red assay, with an IC50 (cytotoxicity)>100 µg/ml. Against the influenza A (H3N2 strain) virus, the EC50 was 35 µg/ml by visual assay and 45 µg/ml by neutral red assay with the same IC50 as above. Compound XXIV was also efficacious vs RSV, with an EC50 of 4 µg/ml using visual assay only, but was not active by neutral red assay. Compound XXIV did not display a virus inhibitory effect against Punta Toro virus at the concentrations tested.

Compound XXV was less active, with EC50 values vs the influenza A (H1N1 strain) virus of 50 µg/ml by visual assay and 35 µg/ml by neutral red assay and an IC50>100 µg/ml (Table 1.8). This compound did not demonstrate a virus inhibitory effect against influenza A (H3N2 strain), influenza B, or RSV at the concentrations tested. Compound XXV did not display a virus inhibitory effect against Punta Toro virus.

TABLE 1.7

Antiviral activity of Compound XXIV (dipalmitoyl-phosphatidyl-ethanolamine conjugated to heparin) at low concentrations

| Virus | $EC_{50}$ (µg/ml) | SI ($IC_{50}/EC_{50}$) |
|---|---|---|
| Visual Observation Assay | | |
| Punta Toro A | >100 | 0 |
| Respiratory Syncytial A | 4 | 25 |
| Influenza A (H1N1 strain) | 5 | 20 |
| Influenza A (H3N2 strain) | 35 | 2.9 |
| Neutral Red Uptake Assay | | |
| Punta Toro A | >100 | 0 |
| Respiratory Syncytial A | >100 | 0 |
| Influenza A (H1N1 strain) | 2.5 | 40 |
| Influenza A (H3N2 strain) | 45 | 2.2 |

SI—selectivity index. Generally, an SI ≧ 10 is indicative of positive antiviral activity, although other factors such as a low SI for the positive control are also taken into consideration.
$IC_{50}$ for Compound XXIV was >100 µg/ml for all viruses.

TABLE 1.8

Antiviral activity of Compound XXV (dipalmitoyl-phosphatidyl-ethanolamine (PE) conjugated to chondroitin-sulfate A) at low concentrations

| Virus | $EC_{50}$ (µg/ml) | SI ($IC_{50}/EC_{50}$) |
|---|---|---|
| Visual Observation Assay | | |
| Punta Toro A | >100 | 0 |
| Influenza A (H1N1 strain) | 50 | 2 |
| Neutral Red Uptake Assay | | |
| Punta Toro A | >100 | 0 |
| Influenza A (H1N1 strain) | 35 | 2.9 |

SI—selectivity index.
$IC_{50}$ for Compound XXV was >100 µg/ml for all viruses.

Using higher concentrations of Lipid-conjugates, the results demonstrate a strong effect of Compound XXIV (100) against infection with Influenza A virus H1N1 strain (Tables 1.9 and 1.10). In addition, Compound XXIII (170) and Compound XXIII (80) showed antiviral activity against the H3N2 strain of Influenza A virus in the visual test but not the neutral red assay (Table 1.10).

TABLE 1.9

Antiviral activity of Compound XXIV (dipalmitoyl-phosphatidyl-ethanolamine conjugated to heparin; MK-610) at high concentration

| Virus | $IC_{50}$ (µg/ml) | $EC_{50}$ (µg/ml) | SI ($IC_{50}/EC_{50}$) |
|---|---|---|---|
| Visual Observation Assay | | | |
| Influenza A (H1N1 strain) | 35 | 400 | 11 |
| Influenza A (H3N2 strain) | 100 | 200 | 2 |
| Influenza B | 90 | 350 | 3.9 |
| Neutral Red Uptake Assay | | | |
| Influenza A (H1N1 strain) | 64 | 1000 | 15.6 |
| Influenza A (H3N2 strain) | 110 | 900 | 8.2 |
| Influenza B | 220 | 450 | 2 |

TABLE 1.10

Antiviral activity of Lipid-Conjugates against Influenza A (H1N1 and H3N2 strains) and Influenza B viruses at high concentration.

| Compound (phosphate content) | Influenza A (H1N1 strain) | | Influenza A (H3N2 strain) | | Influenza B | |
|---|---|---|---|---|---|---|
| Name | Visual | NR | Visual | NR | Visual | NR |
| Ribavirin | 22 | 25 | 56 | 36 | 22 | 19 |
| Compound XXIV (100) | 11 | 15.6 | 2 | 8.2 | 3.9 | 2 |
| Compound XXII (170) | 3.6 | 0 | 25 | 0 | 10 | 0 |
| Compound XXV (60) | 2.5 | 0 | 0 | 0 | 0 | 0 |
| Compound XXIII (80) | 0 | 0 | 10 | 6.5 | 0 | 0 |
| Compound XXV (230) | 0 | 0 | 6.7 | 7.2 | 0 | 0 |
| Compound XXII (85) | 0 | 0 | 2.5 | 0 | 0 | 0 |
| Compound XXIV (50) | 0 | 0 | 0 | 0 | 0 | 0 |
| Compound XXII (40) | 0 | 0 | 0 | 0 | 0 | 0 |
| Compound XXV (100) | 0 | 0 | 0 | 0 | 0 | 0 |

SI—selectivity index ($IC_{50}/EC_{50}$);
Visual = Visual Observation Assay;
NR = Neutral Red Uptake Assay Experiment 1.5 demonstrates the effect of Lipid-conjugate treatment on human influenza virus infection in vivo. We use young adult (18-21 g) female BALB/c mice infected intranasally with either influenza A/NWS/33 (H1N1), A/PR8/34 (H1N1), A/New Caledonia/20/99 (H1N1), A/Victoria/3/75 (H3N2), A/Port Chalmers/1/73 (H3N$_2$), B/Hong Kong/5/72, B/Lee/40, B/Sichuan/379/99, or A/Duck/MN/1525/81 (H5N1) virus at sufficient dose to render death in approximately 90% of the mice, with the mean day to death being 6-10 days. The animals are monitored for arterial oxygen saturation levels using a pulse oximeter on days 3 through 11 (the infection usually induces major declines in these levels by about day 9-10 due to lung consolidation). We also sacrifice mice on days 1, 3, 6, and 9 for assay of lung score, lung weight increase, and lung virus titer. We usually use 22 infected mice for each dosage of test compound, and 35 infected mice treated with placebo. Three uninfected mice are included as toxicity controls, these are treated in parallel to the above, and weight loss or gain is determined during the period of treatment. A group of normal controls are also run in parallel to ascertain their weight gain during the study as well as the normal arterial oxygen saturation levels. Some of these animals are also killed to determine normal lung parameters.

If the test compound is considered to be an immunomodulator, we would inject mice with the compound intraperitoneally every other day for a total of 4 treatments beginning 24 h prior to virus exposure. If the material is considered to be antiviral, a twice daily for 5 days treatment schedule is recommended, with therapy beginning 4 h pre-virus exposure. We generally try to select three dosages varying 2-fold or ½ log10 from each other, with the high dose being approximately the maximum tolerated dose.

Ribavirin is usually included at a single dose as a known positive control.

Experiment 1.6 demonstrates the effect of Lipid-conjugate treatment on vaccinia virus infection in vitro.

BS-C-1 cell monolayers ($3 \times 10^6$ cells), in 3 cm diameter plastic dishes, were infected with a dilution of a crude stock of vaccinia virus (WR strain), to give a m.o.i. of 1 PFU per 10 cells. After adsorption for 1 hr, the cells were washed and 2 ml of Dulbecco's MEM, supplemented with 2% fetal calf serum, containing 1:10 dilution of the compound to be tested, were added. The cultures were incubated for 2 days at 37° C. and then harvested. Control infected cultures that were not treated with the compounds, were harvested at 0 time and at 48 hr. The virus titer in all cultures was determined, after three cycles of freezing and thawing, by plaque assay in BS-C-1 cells.

Table 1.11 demonstrates the capacity of the Lipid-conjugates to prevent infection of target cells by vaccinia virus. Compounds XXII, XXIII, and XXV inhibited viral infection in culture by 62-99%.

TABLE 1.11

Antiviral activity of Lipid-Conjugates against Vaccinia virus

| Time (PFU/culture) (hr) | Compound tested | Virus titer | % inhibition |
|---|---|---|---|
| 0 | — | less than $10^4$ | |
| 48 | — | $8.6 \times 10^7$ | 0% |
| 48 | Compound XXII-40* | $3.3 \times 10^6$ | 96.2% |
| 48 | Compound XXII-80* | $2.3 \times 10^7$ | 73.3% |
| 48 | Compound XXIII | $7.7 \times 10^4$ | 99.9% |
| 48 | Compound XXV | $3.2 \times 10^7$ | 62.8% |

*The number expresses the amount of nmoles lipid conjugated to 1 mg of polymer

These experiments demonstrate that administration of Lipid-conjugates is effective therapy in the prevention and treatment of viral infection, including HIV, influenza and vaccinia viruses.

Example 2

Treatment of *Chlamydia* Infection

Intracellular bacterial parasites are one of the most prevalent forms of sexually transmitted disease and are frequently intractable to conventional antibiotic therapy. Infection of the female genital tract with chlamydia species is a salient example Experiment 2.1 demonstrates the ability of Lipid-conjugate treatment to prevent infection of HeLa cells by *Chlamydia*. Human cervical adenocarcinoma cell line, HeLa 229 (ATCC, Manassas, Calif.), were cultured and incubated with the phospholipid conjugates (20 micromolar) for 30 min, then incubated with *Chlamydia psittaci* (an avian form of *Chlamydia trachomatis*) (guinea pig inclusion conjunctivitis serologically variant strains (servovars)) for 24 hr. Infected cells were detected by cytofluorometry (FACS) using FITC-conjugated anti-*Chlamydia* antibody (FIG. 2.1A).

FIG. 2.1B depicts the dose response of the Lipid-conjugates' inhibitory effect on infection of HeLa cells by *Chlamydia*. HeLa cells were treated with the Lipid-conjugates at the indicated concentration, and infected with *Chlamydia* as described above.

Experiment 2.2 demonstrates the ability of Lipid-conjugates to inhibit *Chlamydia*-induced cell apoptosis. HeLa cells were treated with Lipid-conjugates and infected with *Chlamydia psittaci* as in Experiment 2.1. For determination of apoptosis, detergent-permeabilized cells were stained with propidium iodide, and their fluorescence was measured by cytofluorometry (FIG. 2.2).

The Lipid-conjugates are effective in the prophylaxis and treatment of infection with intracellular bacterial parasites, particularly infections due to chlamydial species. Taken together, the data presented here demonstrate the Lipid-conjugate capacity to ameliorate bacterial toxicity.

Example 3

Obstructive Respiratory Disease

In asthma, the impeded airflow is due to airway obstruction which is the result of constriction and obstruction of luminal vessels of the lungs. In order to determine the effect of Lipid-conjugates on obstructive respiratory disease, contraction of smooth muscle preparations isolated from airways was induced in the presence and absence of Lipid-conjugates. This is a widely-accepted experimental system to investigate airway constriction.

A muscle preparation (tracheal rings) was isolated from rats (Experiments 3.1-3.3) and from guinea pigs (Experiments 3.4-3.5). Muscle contraction was measured by attachment of the muscle to a pressure transducer, which works much like a spring. Administration of asthmatogenic substances such as endothelin-1 (ET) and acetylcholine (AcCh) induces muscle contraction. Endothelins are released upon vascular endothelial injury, and they activate macrophages and act as strong chemo-attractants for circulating monocytes. Endothelins affect vascular smooth muscle fibroblast proliferation; help regulate vascular, airway, and intestinal smooth muscle tone; increase the activity of bone alkaline phosphatase; stimulate release of atrial natriuretic peptide (ANP) from atrial cardiocytes; inhibit the release of renin from glomeruli and modulate norepinephrine at sympathetic nerve termini. Opposing vasomotor effects are regulated through the binding of distinct endothelin receptors for vasoconstriction and vasodilation. Endothelins have been linked to atherosclerosis and various cardiovascular disease states. ET-1 is important in congestive heart failure, renal failure, pulmonary hypertension, hyperlipidemia and metastatic prostate cancer. On the other hand, AcCh is one of the three main receptors on the bronchi of the lungs, which are basically tubes with muscular walls. Stimulation of bronchial AcCh receptor induces muscle contraction and decreased airflow through the bronchi. Thus, ET and AcCh were used to experimentally induce muscle contraction in the lungs as a model of obstructive respiratory disorders.

Experiment 3.1: Effect of post-treatment of rat tracheal rings with Compound XXII on endothelin-1 (ET)-induced contraction. Isolated rat tracheal rings (in a linear array) were bathed in Krebs-Hanselet buffer (pH=7.4), and linked to a tension transducer. ET-1 was added to a final concentration as indicated, and the tracheal ring contraction was determined by the change in the force applied to the tension transducer (FIG. 3.1A). Subsequently, the highest ET concentration was used in testing the Lipid-conjugates to inhibit smooth muscle contraction (FIG. 3.1B). Rat tracheal rings were incubated with 0-3.5 μM of Compound XXII for 1 hr; ET-1 was then added to a final concentration of 1 μM, and ring contraction was determined as in Experiment 3.1A. Data are presented as mean±S.D. of four separate experiments (4 rats).

Experiment 3.2: Effect of pretreatment of rat tracheal rings with Compound XXII and HA on ET-1 induced contraction. Rat tracheal rings were incubated with either 3 μM Compound XXII or hyaluronic acid (HA) for 1 hr. ET-1 was then added to a final concentration of 1 μM (empty bars) or 10 μM (full bars) and the tracheal ring contraction was determined as in Experiment 3.1 (FIG. 3.2).

Experiment 3.3: Effect of pretreatment of rat tracheal rings with Compound XXII and HA on AcCh-induced contraction. The experiment was performed as in Experiment 3.2, except that the tracheal ring contraction was induced by 10 μM AcCh, as shown in FIG. 3.3.

Experiment 3.4: Guinea pig tracheal rings (in a linear array), immersed in a ringer bath, were connected to an apparatus measuring the length of the ring chain. Compound XXIV or Compound XXVI was added to the bath 1 h prior to the stimulation of contraction by either a snake venom PLA2 (Crotalus atrox type II) enzyme, histamine or endothelin-1 as indicated (Table 3.1). Human airways have both Histamine (H)-1 and H2 receptors. H1 receptors, which mediate bronchoconstriction, predominate. Histamine application in experimental models produces signs and symptoms of asthma, such as narrowing of the airways, mucus secretion, wheezing, and coughing.

TABLE 3.1

Inhibition of Tracheal Ring Contraction by Compound XXVI and Compound XXIV

| Stimulant | Lipid-conjugate | % Inhibition |
|---|---|---|
| Phospholipase (0.5 μ/ml) (crotalus atrox type II) | Compound XXVI (10 μM) | 100 ± 0.3 |
| Histamine (20 μM) | Compound XXVI (10 μM) | 69 ± 0.1 |
| Histamine (20 μM) | Compound XXIV (15 μM) | 56 ± 0.05 |
| Endothelin-1 (100 nM) | Compound XXVI (10 μM) | 92 ± 1.1 |

Experiment 3.5: Guinea pig tracheal rings were incubated with or without Compound XXVI for 30 minutes prior to stimulation. The medium was collected after 30 minutes, and $PGE_2$ and $TXB_2$ levels were determined by radioimmunoassay (Table 3.2). $PGE_2$ and $TXB_2$ are metabolites of arachidonic acid produced during inflammatory response.

TABLE 3.2

Inhibition of Tracheal Tissue $PGE_2$ and $TBX_2$ Production by Compound XXVI

| Stimulant | $PGE_2$ (ng/ml) | $TXB_2$ (ng/ml) |
|---|---|---|
| Histamine (40 μM) | 5.1 | 5.6 |
| Histamine (40 μM) + Compound XXVI (10 μM) | n.d. | 1.75 |

(n.d. = below limit of detection.)

Another widely-accepted test of anti-asthma drug action is to study asthma in vivo in an animal model. Asthma is present in animals which have been sensitized to an antigen, and can be monitored for exacerbation and recovery from asthmatic breathing using a body plethysmography. Experiments 3.6-3.8 demonstrate the ability of Lipid-conjugates to exert their pharmacological effect in live animals. The following procedures were applied in these experiments:

Subjects: Inbred Brown Norway male rats (4 weeks old) obtained from Harlan, USA, were used in this study. The Hebrew University Animal Welfare Committee approved all protocols.

Induction of asthma: Asthma was induced in rats by sensitization with ovalbumin (OVA, Sigma—Rehovot, Israel) according to a previously described protocol (Offer et al. *Am J. Physiol Lung Cellular and Molecular Physiology* 288: L523-L529, 2005): On day 0, rats received a single subcutaneous injection of 1 mg OVA+aluminum-hydroxide (200 mg/ml in 0.9% NaCl) (Sigma—Rehovot, Israel) and an intraperitoneal injection of 1 ml containing $6 \times 10^9$ heat-killed Bordetella Pertussis bacteria (Pasteur Marieux, France). Repeated bronchial allergen challenge was performed from day 14 every other day for 1 month by inhalation of OVA (1 mg/ml in 0.9% Normal Saline) for 5 minutes each time in a 20 L box connected to an ultrasonic nebulizer (LS 230 System Villeneuve Sur Lot, France).

Treatments: Rats were divided into 4 treatment groups: 1. No sensitization and no treatment, used as control (Naïve). 2. Sensitization+challenge with OVA and placebo treatment with 1 ml saline before each challenge, used as positive control (OVA) 3. Sensitization+challenge with OVA and treatment with Lipid-conjugate (Compound XXII), either by subcutaneous (SC) injection or inhalation, before every challenge (OVA/Compound XXII). 4. Sensitization+challenge with OVA and treatment with SC injection of dexamethasone 300 μg before each challenge (OVA/Dx) (only in select experiments).

One of two modes of Compound XXII treatments were employed: 1. The rats received an SC injection of 1 ml saline containing 15 mg Compound XXII (to obtain about 1 mg/ml body fluid=20 μM). 2. The rats, placed unrestrained in a 20 liter box connected to an ultrasonic nebulizer, inhaled Compound XXII as follows: 5 ml of 1 mg/ml Compound XXII was aerosolized into the 20 L cage, thus diluting Compound XXII to 0.25 μg/ml aerosol. The rat respiratory rate was 120 breaths/min, with a tidal volume of about 1 ml, thus reaching ventilation of 120 ml/minute. If all of the Compound XXII inhaled in 5 min was absorbed (600 ml), the maximal Compound XXII absorbed was 150 μg.

In mode 1, all groups (5 rats in each) were treated and challenged as described above on day 14, 16, 18 and 20, and pulmonary function (Penh) was assessed on day 20 before and 5 min after challenge (EAR).

In mode 2, each group (10 rats in each) were treated and challenged from day 14, every other day, until day 45. Pulmonary function (Penh) was assessed on day 20 before and 5 min and 8 h after challenge, corresponding to early and late asthmatic reaction (EAR and LAR, respectively).

Assessment of broncho-constriction: Unrestrained conscious rats were placed in a whole-body plethysmograph (Buxco Electronics Inc., Troy, N.Y., USA) connected to a pneumotach (EMKA Technologies, Type 0000) at one end, and to a 10 ml bottle at the other end. The pneumotach was connected to a preamplifier (model MAX2270, Buxco Electronics). Analogue signals from the amplifier were converted to a digital signal by an AD card (LPM-16 National Instruments, Austin, Tex., USA). Broncho-constriction measures were expressed as the enhanced pause (Penh). Penh=(PEF/PIF)*((Te−Tr)/Tr), where PEF=Peak Expiratory Flow, PIF=Peak Inspiratory Flow, Te=Expiratory Time, Tr=Relaxation Time=time of the pressure decay to 36% of total box pressure during expiration.

Broncho-alveolor lavage (BAL): On day 45, the rats were sacrificed by bleeding through the abdominal aorta under anaesthesia with intra-peritoneal injection of sodium pentobarbital (100 mg/kg). The rats were tracheotomized and incannulated through the trachea. Bronco-alveolar lavage (BAL) was collected by repeated washing of the lungs with 5 ml saline to a total of 50 ml.

Assessment of airway pathology: Subsequent to collection of BAL, lungs were removed and inflated with 4% buffered formaldehyde under pressure of 20 cm $H_2O$. The lungs were sliced longitudinally and embedded in paraffin. Three μm histological sections were cut and stained with hematoxylin and eosin for assessments of interstitial and peri-bronchial inflammation and airway smooth muscle thickening. Other slides were stained with Tri-chrome for assessment of sub-epithelial fibrosis (basal membrane) and with PAS for epithelial cell mucus metaplasia.

Histological morphometry of airway structural changes was performed using the "ImageJ" computer program (NIH Bethesda USA) on 3 randomly selected slides from each mouse. Quantification of peribronchial cellular infiltrate in airway tissue was achieved by counting the numbers of these cells in the 50 μm region beneath the epithelium of the airway in hematoxylin and eosin stained sections. Cells were expressed as number per millimeter of airway basal lamina length, which was measured by tracing the basal lamina in calibrated digital images (Kuhn III, C et al. *Am. J. Respir. Cell Mol. Biol.* 2000; 22(3):289-295). Morphometric analysis of ASM and the basal membrane mass as indices of their thickening were performed as previously described (Panettieri R A Jr et al. *Am. J. Physiol. Lung Cell. Mol. Physiol.* 1998; 274: L417-L424). Briefly, measurements of the airway were obtained by tracing the digitalized images of interest. The outlines of the airway structures were subsequently measured. All airways were evaluated for the following morphometric dimensions: length of the airway basement membrane of the epithelium (Lbm) and area of the ASM in the eosin hematoxylin stained slides and the blue stain of the basal membrane of the Tri-chrome stained slides. ASM cells or the basal membrane thickening were normalized to the square of the Lbm (in $\mu m^2$) to correct for differences in airway size. Only large (>2,000 μm Lbm) and medium size airways (1,000-2,000 μm Lbm) were selected as it was shown that the most significant pathological changes occur in these airways.

Protein expression of sPLA2 in lung tissue: Proteins were identified in homogenized lung tissue (100 μg protein) using standard Western blot. A specific polyclonal antibody against Anti-sPLA2 antibody (Santa Cruz) was diluted 1:500 (v/v) in TBST buffer+0.1% BSA. The immune reaction was detected by enhanced chemiluminescence (ECL).

Cysteinyl Leukotriene (CysLT): CysLT levels were measured in BAL using a kit for direct enzyme immunoassay (EIA), according to manufacturer's instructions (Amersham Pharmacia Biotech U.K.). The specificity of the kit was 100% for $LTC_4$, 100% for $LTD_4$, and 70% for $LTE_4$. Result range was between 0 and 48 pg.

Cell culture: Cells were isolated from the BAL and suspended in DMEM medium supplemented with 10% fetal calf serum ARCS) and plated in a 96-well plate at 106 cells/well. The cells were incubated for 2 hours in 37° C., then non-adherent cells were removed by washing with PBS. The adherent cells were re-suspended in DMEM supplemented with 10% FCS at 106 cells/well and incubated for 48 hours. The culture medium was then collected and assayed for determination of biochemical markers.

Nitric Oxide (NO) production: NO production by the BAL cultured macrophages was determined by measuring their level in the culture medium using the photometric method of Griess (Green, L. C., Wagner, D. A., Glogowski, J., Skipper, P. L., Wishnok, J. S., and Tannenbaum, S. R. 1982. Analysis of nitrate, nitrite, and [15N]nitrate in biological fluids. *Anal Biochem.* 126:131-138).

TNFα production: TNFα production by the BAL cultured macrophages was determined in the culture medium using radio-immunoassay (RIA) kits (Amersham-Pharamcia, UK).

Statistical Analysis: All data are expressed as mean±SEM. One way ANOVA was used to compare treatment groups. Pair-wise comparisons were performed by the Tukey-Kramer HSD test (p=0.05). Where necessary, data were log transformed before analysis to stabilized variances. In all analyses P<0.05 was considered statistically significant.

Statistics: Statistical analysis was performed using statistical software (GB-STAT, Dynamic Microsystem, Silver Spring, Md., USA. Analysis of variance (ANOVA) was used to assess difference of the results of the treatment groups A Tukey test was used to compare between each one of the treatment groups. A value of p<0.05 was considered as a significant difference.

Experiment 3.6: SC administration of Lipid-conjugates considerably ameliorates OVA-induced broncho-constriction (FIG. 3.4). Bronchoconstriction was induced in OVA-sensitized rats by inhalation of OVA, and expressed by the difference in Penh measured before and 5 min after allergen challenge. Data are presented as mean±SEM for 10 rats. Statistical significance: a−P<0.01 between columns marked "a"; b, c−P<0.05 between columns marked "b" and "c", respectively SC administration of Lipid-conjugates also reduced the expression of secretory phospholiapse (FIG. 3.5). The figure depicts Western blot and corresponding densitometry of $sPLA_2$ in lung homogenates of rats with naïve, OVA-induced asthma, and OVA-induced asthma treated with Compound XXII. For densitometric analysis, the density values for each enzyme were normalized to Naïve values. Lipid-conjugates also prevented the production of the broncho-constricting lipid mediators cysteinyl leukotrienes (FIG. 3.6). Broncho-alveolar lavage (BAL) was collected upon sacrifice and CysLT levels were determined by EIA, as described in Methods. Data are presented as mean±SEM for 10 rats. Statistical significance: a, b−P<0.01. There was no significant difference between OVA/Compound XXII-treated and Naive rats.

Experiment 3.7: Treatment of asthmatic rats with Lipid-conjugates administered by aerosol protects the rats from sensitization to OVA. Lipid-conjugates markedly reduced OVA-induced broncho-constriction in both the early and late asthmatic reaction (FIG. 3.7). Bronchoconstriction, expressed as the percent change of Penh, was induced in OVA-sensitized rats by inhalation of OVA, and measured before allergen challenge, and 5 min and 8 h after allergen challenge. Data are presented as mean±SEM for 10 rats. Two experiments were performed for early asthmatic reation (EAR). 5 rats were included in each group in the first experiment. The same experiment was repeated with 10 rats in each group, which were further used for determination of late asthmatic reation (LAR). A combined statistical test for EAR yielded p<0.01 between Asthmatic (OVA/OVA) and Compound XXII-treated (OVA/OVA+Compound XXII). There was no significant difference between the Compound XXII-treated and the Naïve or Dx-treated groups. For LAR, p<0.01 between Asthmatic and Compound XXII-treated and no significant difference between the Compound XXII-treated and the Naïve or Dx-treated groups.

Lipid-conjugates administered in aerosol form also inhibited the production of CysLT in OVA-sensitized rats (FIG. 3.8). Broncho-alveolar lavage (BAL) was collected upon sacrifice of rats, and CysLT levels were determined by EIA. Data are presented as mean±SEM for 10 rats. P<0.01 between Asthmatic and Compound XXII-treated rats, and no significant difference between Compound XXII-treated and Naïve rats.

Lipid-conjugates administered in aerosol form also inhibited the production of nitric oxide (NO), a characteristic constrictor of smooth muscle cells (FIG. 3.9). Macrophages, collected from the BAL of the different groups, were cultured without further treatment with Compound XXII or Dx, and NO production was determined as described in Methods. Data are presented as mean±SEM for 10 rats. NO level was reduced compared to asthmatic and naïve rats by both Compound XXII, p<0.001 and p<0.001 respectively and by Dx p<0.001 and p<0.001, respectively.

These treatments also prevented asthma-associated inflammation, as expressed by prevention of inflammatory cell infiltration and airway remodeling (FIG. 3.10-3.11). Rats were subjected to OVA inhalation every other day for 30 days. Rats were administered aerosolized Compound XXII for 5 min before every allergen inhalation The rats were sacrificed on Day 45. A—Staining with hematoxylin eosin for detection of inflammatory cell infiltration and changes in smooth muscle cell (ASM) thickness. B—Staining of connective tissue (collagen) with Mason-Trichrom, for detection of changes in basal membrane thickness. C—Staining with Periodic Acid Schiff (PAS) for detection of mucus metaplasia of respiratory epithelial cells. 1, 2, 3 and 4 depict tissues of Naïve, Asthmatic, Compound XXII-treated and Dx-treated rats, respectively.

Lipid-conjugates further prevent production of TNFα by lung macrophages (FIG. 3.12). Macrophages, collected from the BAL of the different groups, were cultured without further treatment with Compound XXII or Dx, and TNFµ production was determined as described. Data are presented as mean±SEM for 10 rats. p<0.001 between Asthmatic and Compound XXII-treated rats. There were no significant differences between Compound XXII-treated, Naive and Dx-treated rats.

Experiment 3.8: Treatment of Asthmatic rats with Lipid-conjugates administered by aerosol sensitized to OVA. Compound XXII is effective in preventing allergen-induced broncho-constriction in already asthmatic subjects when inhaled before allergen (OVA) challenge (FIG. 3.13). OVA-sensitized asthmatic rats inhaled nebulized Compound XXII (1 mg/ml) for 5 minutes, or nebulized normal saline. 30 minutes later, all groups were challenged by inhalation of OVA (1 mg/ml) for 5 minutes. Penh was measured before the treatments (baseline), and 5 minutes after each inhalation. Data are presented as mean±SEM for 5 rats. *, **, P<0.05). Lipid-conjugates also reverse broncho-constriction (induce broncho-dilation) when inhaled after allergen challenge (FIG. 3.14) OVA-sensitized asthmatic rats challenged by inhalation of OVA (1 mg/ml) for 5 minutes. Thirty minutes later, they were treated by inhalation of nebulized Compound XXII (1 mg/ml) or with normal saline for 5 minutes. Penh was measured before challenge (baseline), and after challenge and treatment. Data are presented as mean±SEM for 5 rats. *, P<0.05.

These experiments demonstrate that the Lipid-conjugates may be used for the treatment of obstructive respiratory disease, alleviating airway narrowing by a plurality of mechanisms, including inhibition of contraction and reduction of airway obstructing infiltrates. Additional support for the utility of the Lipid-conjugates in treating obstructive respiratory disease is provided by the results of Experiments 7.1-7.3 in U.S. application Ser. No. 10/627,981, incorporated herein by reference, demonstrating that the Lipid-conjugates are effective in inhibiting smooth muscle cell proliferation, which is a major cause of morbidity in chronic asthma. Anti-inflammatory effects of Lipid-conjugates may be useful in treating lung infections accompanied by excessive, uncontrolled inflammation such as influenza, tuberculosis, schistosomiasis, chronic bronchitis, pneumonia, SARS, respiratory syncitial virus, Empyema Thoracis, whooping cough, and other respiratory infectious disease.

Example 4

Sepsis

Sepsis is characterized by enhanced levels of cytokines such as Tumor necrosis factor (TNFα) and interleukin (IL)-1, IL-6 and IL-8, and endothelial cell adhesion molecules, such as ICAM-1 and E-Selectin. These molecules are involved in the pathogenesis of septic shock, and are released both locally and systemically to produce noxious and irreversible effects on tissue integrity and systemic hemodynamics. Exposure of cells to the bacterial lipopolysaccharide (LPS) and Lipoteichoic acid (LTA) immunogens comprises a commonly-used model system for assaying the response of these agents to septicemic conditions. It should be noted that bacterial LPS has both endotoxic and immunogenic components. LPS toxicity is associated with the lipid component (Lipid A) and immunogenicity is associated with the polysaccharide components.

Experiment 4.1 demonstrates the ability of the Lipid-conjugates to inhibit elaboration of TNF-α in human tissue. Fresh heparinized (12.5 U/ml) human venous blood from healthy blood donors was diluted 1:3 with RPMI-1640 medium supplemented with 200 mM glutamine, 200 U/ml penicillin and 200 U/ml streptomycin. Fractions (300 µl) of 1:3 diluted blood were distributed in 24 well Multidisk plates (Nunclon). Blood samples were pre-incubated (30 min at 37° C.) in a humidified atmosphere of 6% $CO_2$ with 100 µl of compound or solvent before being stimulated by the addition of 100 µl of lipopolysaccharide E. coli 026:B6 (LPS) at a final concentration of 100 ng/ml. After a 6 h incubation, the 24 well plates were spun down (20,000 rpm) and assayed for cytokine content by ELISA. The various Compound XXIIs differed in their phosphate content (FIGS. 4.1-I and 4.1-II).

Experiment 4.2 demonstrates the capacity of Lipid-conjugates to ameliorate sepsis in an in vivo rat model. Endotoxins administered to animals produce cardiovascular and multiorgan disorders that are similar to clinical sepsis. Thus, in the present study, a rat model was developed to test possible Lipid-conjugate effects on mediator production and mortality in endotoxin-induced Sepsis. Rats were intraperitoneally (i.p.) or intravenously (i.v.) injected with a Lipid-conjugate (Compound XXII, 100 mg/kg) dissolved in sterile saline or with sterile saline alone as placebo. After 3 hours, all rats received LPS (15 mg/kg i.p.; *Escherichia coli* 111:B44 LPS, Sigma, Deisenhofen, Germany). In rats that were pretreated with Compound XXII, LPS was injected together with a second dose of Compound XXII (50 mg/kg). The effect of Compound XXII on LPS injected rats was observed over a time period of 48 hours. As show in FIG. 4.2, treatment with Compound XXII markedly reduced the mortality rate among septic rats.

Experiment 4.3 demonstrates the ability of Lipid-conjugates to suppress LPS-induced increases of cytokines TNF-α and IL-6 in serum Rats were administered 100 mg/kg i.p. Compound XXII 3 h prior to an i.p. injection of LPS (7.5 mg/kg). Blood samples were collected 1, 6, 12, and 24 hours after LPS injection to assess cytokine concentrations (FIG. 4.3A). In another experiment, rats were pretreated with a priming dose of Lipid-conjugates (Compound XXII or Compound XXV) 0, 3, 6, or 12 hours before LPS administration or did not receive Lipid-conjugates. Thereafter, the animals received LPS (7.5 mg/kg) i.p. alone or together with Compound XXII (150 mg/kg) or Compound XXV (50 mg/kg). Blood samples were collected after LPS injection. A group of rats that was not treated with Lipid-conjugates or LPS served as negative controls (FIG. 4.3B). All cytokines were measured in separated serum by ELISA Immunoassays (R&D Systems GmbH, Wiesbaden, Germany) according to the instructions of the manufacturer. FIG. 4.3 demonstrates that cytokine levels in the serum of septic rats are markedly reduced by treatment with Lipid-conjugates.

In Experiment 4.4, Compound XXII was given i.v. at the same time as LPS was given i.p. As demonstrated in FIG. 4.4, endotoxin-induced cytokine production was suppressed equally well by co-administration of i.v. Compound XXII with LPS as with pretreatment with i.p. Compound XXII.

In Experiment 4.5, sepsis was induced by LPS (gram-positive endotoxin, 5 mg/kg) and lipoteichoic acid (LTA, gram-negative endotoxin, 5 mg/kg; *Staph. aureus* LTA, Sigma, Germany). FIG. 4.5 demonstrates that 150 mg/kg Compound XXII is effective in suppressing cytokine production induced by 5 mg/kg i.p. LPS as well as by a combined treatment with 5 mg/kg i.p. LPS and 5 mg/kg i.p. LTA 1 and 6 hours after LPS or LPS+LTA treatment.

Experiment 4.6 demonstrates that Lipid-conjugates inhibit endotoxin-induced cytokine mRNA expression. For RNase protection assay (RPA), rat lung and kidney were removed from Lipid-conjugate-treated or untreated rats 24 hours after induction of sepsis for total RNA isolation using Trizol reagent (Gibco BRL, Eggenstein, Germany). The concentration of RNA in each sample was assessed spectrophotometrically. To evaluate specific RNA levels in rat lung and kidney, a multiprobe RPA kit was used (riboQuant, PharMingen, Heidelberg, Germany) according to manufacturer's instructions. Briefly, a set of $^{32}$P-labeled RNA probes synthesized from DNA templates using T7 polymerase was hybridized with 7 μg of total RNA, after which free probes and single-stranded RNA were digested with RNase. Undigested probes and digested samples were loaded on to a 5% denaturing polyacrylamide gel, dried and exposed to a Kodak X-apart film. The expression of each specific mRNA was related to two housekeeping genes, glyceraldehyde-3-phosphate dehydrogenase (GAPDH) and L32, to exclude differences in the amount of RNA that was hybridized. The following templates for rat cytokines-were used in the present study: IL-1-α, IL-1β, IL-2, IL-3, IL-4, IL-5, IL-6, IL-10, TNF-α, TNF-β, IFN-γ, L32 and GAPDH. As shown in FIG. 4.6, treatment with Lipid-conjugate inhibited endotoxin-induced cytokine gene expression. This supports the findings of FIG. 4.3, which demonstrates a decrease in IL-6 protein.

Experiment 4.7 demonstrates the effect of Lipid-conjugates on the RNA expression of iNOS and secretory PLA$_2$ Type II (sPLA$_2$II) in the kidney and lung of rats with LPS-induced sepsis. RNA expression was measures using Polymerase Chain Reaction (PCR). Total RNA isolated from rat lung and kidney was subjected to DNAse digestion (Gibco BRL, Eggenstein, Germany) to remove possible contaminations of genomic DNA. 1 μg of total RNA was reverse-transcribed to cDNA using SuperScript TM II Preamplification System (Gibco BRL, Eggenstein, Germany), essentially as recommended by the manufacturer's instructions PCR amplification of 0.5 μl cDNA was performed in a total volume of 25 μl containing 19.6 pmol of each primer, 5 mM dNTPs, 2.5 U Taq Polymerase, 10 mM Tris HCl, 7.5 mM KCl, 1.5 mM MgCl$_2$. PCR reactions were initiated at 94° C. for 3 min, followed by varying cycles of amplification, each consisting of denaturation at 94° C. for 1 min, annealing at 60° C. for iNOS and 65° C. for sPLA$_2$-IIA and primer extension 72° C. for 2 min. At the end of the amplification cycles, the products were incubated for 10 min at 72° C. In each set of PCR reactions, two control reactions were included. In one control reaction, reverse transcriptase was omitted, while in the other control reaction, cDNA was omitted. PCR products were separated on a 1% agarose gel. FIG. 4.7 demonstrates the ability of Lipid-conjugates to suppress the endotoxin-induced gene expression of sPLA$_2$ IIA and iNOS.

Experiment 4.8 demonstrates Lipid-conjugate inhibition of adhesion molecule expression: For immunohistochemical determination of ICAM-1 expression in rat tissue, cryostat sections of pulmonal and renal tissue were analyzed by an indirect immunoperoxidase technique. Briefly, ethanol-fixed sections were incubated with primary antibody against ICAM-1 for 1 hour, washed and incubated with peroxidase-conjugated secondary rat IgG antibody for 30 min. The reaction was developed with ABC solution Vectastain (Wertheim, Germany) and terminated by washing with TBS. Sections were counterstained with hematoxylin-eosin, dehydrated and analyzed. FIG. 4.8 demonstrates the inhibitory effect of the Lipid-conjugates on endotoxin-induced adhesion molecule expression in septic rat tissue.

The results presented in FIGS. 4.1-4.8 demonstrate the capacity of Lipid-conjugates to ameliorate the endotoxin-induced mortality among septic rats (FIG. 4.2); reduce arachidonic acid release induced by hydrogen peroxide and PLA2 (FIG. 4.1); reduce the blood level of the cytokines TNFα and IL-6 when induced by LPS given is either i.p. (FIG. 4.3), or i.v. (FIG. 4.4), and by LPS+LTA (FIG. 4.5);

suppress the mRNA expression of TNFα, IL-1 and IL-6 (FIG. 4.6), and of secretory phospholipase $A_2$ ($sPLA_2$-IIA) and the inducible nitric oxide synthase (iNOS) in the lung and kidney of the septic rats (FIG. 4.7); and suppress the expression of the adhesion molecule ICAM-1 in lung and kidney of the septic rats (FIG. 4.8). Additional support for Lipid-conjugate protection from bacterial toxicity is provided in U.S. application Ser. No. 10/627,981, incorporated herein by reference. These results clearly demonstrate the therapeutic capacity of the Lipid-conjugates in the treatment of sepsis, bacteremia-induced shock, septic shock, or septicemia. Further, the efficacy of Lipid-conjugates in protecting against septic shock may contribute to their usefulness in treating pathogenic baterial infections.

Example 5

Hemolysis

Hemolysis, the breakdown of red blood cells (RBC), may be either a primary disease in itself, or a syndrome associated with another disease or physiological insult. In order to determine the effect of Lipid-conjugates on hemolysis, red blood cells were incubated in the presence of known membrane destabilizing agents and the release of hemoglobulin into the extracellular medium was detected.

Experiment 5.1 demonstrates that the Lipid-conjugates serve to maintain the stability of human red blood cells exposed to membrane-destroying agents. Human RBC were washed in saline and suspended in Hanks buffer (pH 7.4). Hemolysis was induced in the absence or presence of 10 μM Lipid-conjugates by treatment with either 5 U/ml streptolysin O (SLO), 25 U/ml streptolysin S (SLS), or 5 μg/ml lysophosphatidylcholine (lyso-PC) for 20 min. The cell membranes were spun and the hemoglobin content in the supernatant was determined by measuring the O.D. at 540 nm (Table 5.1).

TABLE 5.1

Prevention of Hemolysis by Compound XXII,
Compound XXVI and Compound XXIV

| Lipid-conjugate | HEMOLYSIS (O.D. AT 540 nm) | | |
| --- | --- | --- | --- |
| | SLO | SLS | Lyso-PC |
| None | 1.000 | 1.000 | 1.000 |
| HA | 1.000 | 1.000 | 1.875 |
| Compound XXII-30* | 0.650 | 0.750 | 0.335 |
| Compound XXII-60* | 0.012 | 0.005 | 0.017 |
| Compound XXII-110* | 0.005 | 0.002 | 0.012 |
| Compound XXIV | 0.002 | 1.100 | 0.002 |
| Compound XXVI-60* | 0.012 | 0.005 | 0.002 |
| Compound XXVI-110* | 0.002 | | 0.002 |

*The number expresses the amount of nmoles lipid conjugated to 1 mg of polymer.

These experiments demonstrate that the Lipid-conjugates are effective therapy in the treatment of hemolysis and of value as preservatives in blood product storage. Thus Lipid-conjugates are demonstrated to have utility in maintaining hematocrit and in blood-banking. Further, the efficacy of Lipid-conjugates in protecting against membrane destabilization may contribute to their usefulness in treating infections. For example, Lipid-conjugates may protect against cytopathic effects due to infection or cell to cell spread.

Example 6

Anti-Oxidant Therapy

The noxious effect of peroxide flee radicals on living tissue is known as oxidative damage. When cell membranes are the targets for this damaging process, membrane dysfunction and instability result. Oxidative damage to blood proteins, particularly blood lipid proteins, results in their over-accumulation in cells lining the vasculature, thus contributing to atherogenesis. In fact, oxidative cell damage is a major mechanism attributed to the process of aging or senescence.

In order to determine the effect of Lipid-conjugates on oxidative damage to proteins or cell membranes, tissue was exposed to hydrogen peroxide ($H_2O_2$) produced by (a) the enzyme glucose oxidase (GO) in the absence or presence of additional membrane destabilizing agents such as $PLA_2$ or (b) by exposure to divalent cations, such as copper.

Experiments 6.1-6.3 demonstrate the ability of Lipid-conjugates to preserve cells from oxidative damage, as judged by the cells' retention of both arachidonic acid and of low molecular weight intracellular substances.

Experiment 6.1: Confluent BGM (green monkey kidney epithelial) cells were labeled with $^3$H-arachidonic acid. The cells were treated with Compound XXVI for 30 min prior to treatment with GO and $PLA_2$ (0.5 U/ml) (FIG. 6.1).

Experiment 6.2: BGM cells were labeled with $^{35}SO_4$ overnight. The cells were washed with DMEM (containing 10 mg/ml BSA) 4 times with PBS. The cells were then incubated in DMEM supplemented with GO (an $H_2O_2$ generator) for 90 min, and the culture medium was collected and counted for $^{35}$S radioactivity. For, treatment with Compound XXVI, cells were incubated with 3 or 10 μM Compound XXVI for 30 min prior to introduction of GO. Data are presented as mean±SEM for 5 replications. *p<0.005; p<0.001 (FIG. 6.2**).

Experiment 6.3 demonstrates the ability of Lipid-conjugates to inhibit the oxidation of blood lipoprotein. Low density lipoprotein (LDL; 0.1 μM) and or hydroperoxides (LOOH) were incubated in the absence and presence of various concentrations of Compound XXII or HA at 37° C. At time zero, 5 μM $CuCl_2$ was added to the dispersions, and the mixtures were continuously monitored for oxidation products at 245 nm (FIG. 63). The absorbance at 245 (OD units) is depicted as a function of time (Shnitzer et al., Free Radical Biol Med 24; 1294-1303, 1998).

Additional support for the anti-oxidant capacity of the Lipid-conjugates is provided by Experiment 7.4 in U.S. application Ser. No. 10/627,981, incorporated herein by reference, showing the inhibitory effect of Lipid-conjugates on ischemia/reperfusion-induced activation of white cells.

These experiments demonstrate that administration of Lipid-conjugates is an is effective therapy to prevent tissue damage induced by oxidative stress (associated with free radical and hydrogen peroxide production) by a plurality of mechanisms, including inhibiting the oxidation of lipoprotein, inhibiting arachidonic acid release, and preserving the integrity of cell membranes (inhibiting GAG degradation), including red blood cell membranes, as described below. The efficacy of Lipid-conjugates in protecting against tissue damage induced by oxidative stress may contribute to their usefulness in treating pathogenic infections.

Example 7

Central Nervous System (CNS) Insult

Infection, ischemic stroke, trauma, cancer metastases, and degenerative disease exemplify physiological insults in which brain tissue injury may be severe and irreversible. Tissue injury typically evokes a myriad of physiological responses to stress, which in the central nervous system take the form of chemical substances released by support tissue. However, an excess of one or more of these potentially neurotoxic "wound" chemicals may serve to further disrupt the healing process and contribute to the brain tissue damage. Commonly accepted models for assessing the neuroprotective ability of a new drug employ preparations of brain matrix cells (e.g., glial cells), neurotransmitter-releasing cells (e.g., PC12 cells), and migratory blood cells (macrophages and lymphocytes) which are typically recruited to the sites of damaged brain tissue. Tissue injury in the CNS is frequently compounded by local disruption of the blood brain barrier and subsequent passage of migratory blood cells which may exacerbate the effects of the original insult and lead to more extensive tissue damage.

In response to substances associated with stress and impending injury, such as the immunogen lipopolysaccharide (LPS), the cytokine TNFα or the neurotoxin pardaxin, cells of the central nervous system activate a myriad of wound-response substances, such as $sPLA_2$, prostaglandin ($PGE_2$), thromboxane ($TXB_2$), 5-HETE, oxygen radicals, nitric oxide, or dopamine. When expressed in excess, these substances are either themselves neurotoxic or indicative of cotemporal neurotoxicity, thus their suppression is a frequently chosen target for developing neuroprotective drugs.

Experiments 7.1-7.2 demonstrate Lipid-conjugate inhibition of prostaglandin ($PGE_2$) release.

Experiment 7.1: Glial cell media was replaced with fresh media prior to all experiments, supplemented with 10 µg/ml LPS. Lipid-conjugates were added 30 minutes before exposure to LPS. The tissue cultures were further incubated at 37° C. for 24 h. Then the medium was collected and the cells were incubated in fresh medium containing LPS and Lipid-conjugate. After an additional 24 h, supernatants were taken for determination of $PGE_2$ content by ELISA (FIG. 7.1).

Experiment 7.2: Rat adrenal pheochromocytoma (PC12) cells were incubated with the indicated Lipid-conjugate and then washed and then stimulated with pardaxin (PX) for 30 minutes. The amount of $PGE_2$ released to the medium was determined by ELISA (FIG. 7.2).

Experiments 7.3 and 7.4 demonstrate suppression of nitric oxide production by the Lipid-conjugates. Glial cell media was replaced with fresh media, supplemented with 10 µg/ml LPS. Lipid-conjugates were added 30 minutes before exposure to LPS. The tissue cultures were further incubated at 37° C. for 24-48 h. Supernatants were taken after 24 h for determination of NO by calorimetric measurement using the Griess reagent (FIG. 73). Alternately, primary mouse peritoneal macrophages were treated with Lipid-conjugates at the indicated concentration for 30 minutes (FIG. 7.4). Then LPS (1 µg/ml) was added to the culture either directly or after washing of the Lipid-conjugates. Nitric oxide was determined by the Griess calorimetric method.

Experiment 7.5 demonstrates Lipid-conjugate-induced inhibition of soluble phospholipase $A_2$ ($sPLA_2$) release from glial cells (FIG. 7.5). Glial cell media was replaced with fresh media, supplemented with 10 µg/ml LPS. Lipid-conjugates were added 30 minutes before exposure to LPS. The tissue cultures were further incubated at 37° C. for 24-48 h. Culture medium samples were taken after 24 h for determination of $PLA_2$ activity by the hydrolysis of radioactively labeled *E. coli* membranes. The radioactive free fatty acid released in this reaction was counted in a radioactivity scintillation counter.

Experiments 7.6-7.7 demonstrate the ability of the Lipid-conjugates to suppress is the activation of endogenous phospholipase $A_2$, measured as fatty acid release. PC12 cells were metabolically labeled with $^3H$-arachidonic acid (AA) or $^3H$-oleic acid for at least 6 h, then washed and incubated with Lipid-conjugate as indicated for 30 minutes. The cells were then washed, stimulated with PX for 30 minutes and the amount of $^3H$-fatty acid released to the medium was determined in a scintillation counter (FIG. 7.6). For release of oleic acid from macrophages, murine $P388D_1$ cells were metabolically labeled with radioactive oleic acid, and the release of radioactive oleic acid was determined in the presence (full circles) and absence (empty circles) of LPS following pretreatment with the indicated concentration of the Lipid-conjugate, as shown in FIG. 7.7.

Experiment 7.8 demonstrates the ability of Lipid-conjugates to suppress dopamine (DOPA) release. PC12 cells (at confluence) were loaded with radioactive DOPA for 4 h, then washed in the presence of an antioxidant. The cells were then incubated with the indicated Lipid-conjugate for 30 min, then washed and stimulated with PX for 15 min. The amount of labeled DOPA released to the culture medium was determined in a scintillation counter (FIG. 7.8).

Experiment 7.9 demonstrates Lipid-conjugate suppression of 5-HETE release. PC12 cells, under identical conditions to those in Experiment 7.8, were incubated with the indicated Lipid-conjugate, followed by PX stimulation. The amount of 5-HETE released was determined by ELISA (FIG. 7.9).

Experiment 7.10 demonstrates the potency of Lipid-conjugates in inhibiting cell permeation through endothelial cell barrier. Using the T cell transendothelial migration assay (FIG. 7.10), primary pig brain endothelial cells (PBEC) were plated onto a collagen-coated filter, separating between the upper and lower chambers. Human peripheral blood T cells were prepared as described in Cabanas and Hogg (1993, PNAS 90: 5838-5842). The T cells were maintained in recombinant human IL-2 for up to 12 days prior to use. Approximately $10^5$ T-cells were added to the upper chamber of the Transwells above the confluent PBEC monolayer and incubated at 37° C. for 5 h. Compounds for testing were also added on the PBEC monolayer at the same time as the T cells. Electrical resistance values were measured over this period at hourly intervals. At 5 hours the Transwells were briefly rinsed in warm medium and fixed in paraformaldehyde. The number of T cells which had migrated to the underside of the filter (i.e., through the PBEC monolayer) was counted as described.

These experiments demonstrate that the Lipid-conjugates are potent neuroprotective agents and effective against neurotoxic agents. Lipid-conjugates can prevent tissue damage following physiological insult to the central nervous system and are thus useful when administered as therapy for the treatment of brain injury in settings such as infection, stroke, tumor, trauma, and degenerative disease. Additional support for the efficacy of administering Lipid-conjugates as neuroprotective agents is found in the results of Experiment 7.4 in U.S. application Ser. No. 10/627,981, incorporated herein by reference, demonstrating the efficacy of administering Lipid-conjugates for the treatment of ischemia/reperfusion injury. The efficacy of Lipid-conjugates in protecting against tissue injury in the CNS by decreasing inflammatory activators may contribute to their usefulness in treating or altering symptoms of CNS infectious disorders, such as viral meningitis, Encephalitis, Poliomyelitis, bacterial meningitis, subdural empyema, and CNS helminthic infections.

Example 8

Toxicity Tests

Toxicity is a measure to the degree to which a compound or substance is deleterious to an organism Toxicological effects are generally dose-dependent. A therapeutic compound that is non-toxic, even at high doses, would have an advantage over other compounds.

In Experiment 8, the Lipid-conjugates Compound XXII, Compound XXIV, Compound XXV and Compound XXVI were evaluated for toxicity. Toxicity was evaluated in mice (3/group) one week after a single i.p. dose of 1000, 500 or 200 mg/kg of Lipid-conjugates. Mortality rate, body weight, blood count (red and white cells), hematocrit, and internal organ histology after sacrifice were assessed. These parameters were compared in Lipid-conjugate-treated and in control, untreated mice. Treatment with Lipid-conjugates did not alter the parameters described above, with the exception of Compound XXV, which induced hemorrhage.

Tables 8.1 and 8.2 depict the non-toxicity of Compound XXII as demonstrated in acute (Table 8.1) and long-term (Table 8.2) toxicity tests.

TABLE 8.1

Results of acute (7 day) toxicity test

| Dose of Compound XXI | Body weight (g) | | RBC × $10^6$ | WBC × $10^3$ | Hematocrit % |
|---|---|---|---|---|---|
| (mg/kg body weight) | Start | Final | | | |
| 0 (control) | 21.9 ± 0.2 | 22.6 ± 0.3 | 10.7 ± 0.4 | 9.3 ± 0.3 | 45.0 ± 0.5 |
| 250 | 22.1 ± 0.4 | 23.1 ± 0.6 | 11.4 ± 0.1 | 7.7 ± 0.2 | 43.3 ± 0.7 |
| 500 | 21.4 ± 0.3 | 22.3 ± 0.4 | 11.5 ± 0.3 | 8.1 ± 1.3 | 44.7 ± 2.3 |
| 1000 | 21.7 ± 0.2 | 22.1 ± 0.2 | 10.9 ± 0.4 | 7.4 ± 0.6 | 40.3 ± 0.7 |

RBC = red blood cells;
WBC = white blood cells.
Data are presented as mean ± SEM.

For the long-term toxicity test a group of 6 mice received an i.p injection of 100 mg Lipid-conjugate (Compound XXII)/kg body weight 3 times a week for 30 weeks (e.g., 180 mg total to a mouse weighing 20 g). Toxicity was evaluated as for Table 8.1. The results of the long-term toxicity test are depicted in Table 8.2. There were no incidents of mortality and no significant changes in body weight, red or white blood cell count, or hematocrit induced by this treatment compared to control, untreated mice.

TABLE 8.2

Results of long-term (30 weeks) toxicity test

| Dose of Compound XXII (mg/kg body weight, 3 times/week for 30 weeks) | Body weight (g) Final | RBC × $10^6$ | WBC × $10^3$ | Hematocrit % |
|---|---|---|---|---|
| 0 (control) | 39.5 ± 3.1 | 10.9 ± 0.8 | 9.3 ± 0.6 | 45.0 ± 0.8 |
| 100 | 39.0 ± 2.7 | 11.7 ± 0.7 | 8.1 ± 15 | 43.4 ± 4.9 |

Thus, the Lipid-conjugates have very low toxicity, as indicated in short and long-term toxicity tests.

It will be appreciated by persons skilled in the art that the present invention is not limited by what has been particularly shown and described herein above and that numerous modifications, all of which fall within the scope of the present invention, exist. Rather, the scope of the invention is defined by the claims which follow:

What we claim is:

1. A method of suppressing, inhibiting, or treating an infection in a subject comprising the step of administering to said subject an effective amount of a lipid conjugate compound, or its pharmaceutically acceptable salt or pharmaceutical product thereof, wherein said compound is represented by the structure of the general formula (I):

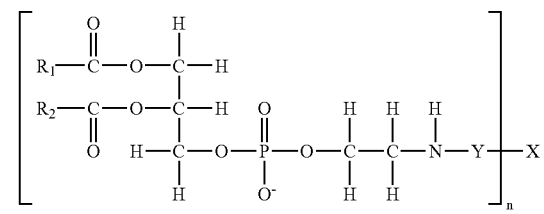

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is either a physiologically acceptable monomer, dimer, oligomer or a physiologically acceptable polymer, wherein X is a glycosaminoglycan; and
- n is a number from 1 to 1,000;
- wherein if Y is nothing the phosphatidylethanolamine is directly linked to X via an amide bond and if Y is a spacer, said spacer is directly linked to X via an amide or an esteric bond and to said phosphatidylethanolamine via an amide bond.

2. The method according to claim 1, wherein said $R_1$ and $R_2$ are myristic acid moieties.

3. The method according to claim 1, wherein said glycosaminoglycan is chondroitin sulfate.

4. The method according to claim 3, wherein said chondroitin sulfate is chondroitin-6-sulfate, chondroitin-4-sulfate or a derivative thereof.

5. The method according to claim 1, wherein said glycosaminoglycan is heparin.

6. The method according to claim 1, wherein said physiologically acceptable polymer is hyaluronic acid.

7. The method according to claim 1, wherein said infection is viral.

8. The method according to claim 7, wherein said infection is mediated by influenza virus.

9. The method according to claim 7, wherein said infection is mediated by Human Immunodeficiency Virus (HIV).

10. The method according to claim 7, wherein said infection is mediated by a poxvirus.

11. The method according to claim 1, wherein said infection is bacterial.

12. The method according to claim 11, wherein said infection is mediated by *Chlamydia*.

* * * * *